United States Patent
Kammerer

(10) Patent No.: US 7,131,943 B2
(45) Date of Patent: Nov. 7, 2006

(54) SURGICAL INSTRUMENT AND METHOD FOR TREATING ORGAN PROLAPSE CONDITIONS

(75) Inventor: Gene W. Kammerer, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/359,406

(22) Filed: Feb. 6, 2003

(65) Prior Publication Data

US 2003/0176762 A1 Sep. 18, 2003

Related U.S. Application Data

(63) Continuation-in-part of application No. 10/191,572, filed on Jul. 9, 2002, which is a continuation of application No. 09/873,571, filed on Jun. 4, 2001, which is a continuation-in-part of application No. 09/521,801, filed on Mar. 9, 2000, now Pat. No. 6,273,852.

(60) Provisional application No. 60/356,697, filed on Feb. 14, 2002.

(51) Int. Cl.
*A61F 2/00* (2006.01)
(52) U.S. Cl. ............................ 600/30; 600/37
(58) Field of Classification Search ............ 600/29–32; 128/897–898, DIG. 25; 606/119, 148, 222–225, 606/37
See application file for complete search history.

(56) References Cited

U.S. PATENT DOCUMENTS

| | | | |
|---|---|---|---|
| 3,182,662 A | 5/1965 | Shirodkar | |
| 3,212,502 A | 10/1965 | Myers | |
| 3,311,110 A | 3/1967 | Singerman | |
| 3,372,695 A | 3/1968 | Beliveau et al. | |
| 3,472,232 A | 10/1969 | Earl | |
| 3,608,095 A | 9/1971 | Barry | |
| 3,763,860 A | 10/1973 | Clarke | |
| 3,858,783 A | 1/1975 | Kapitanov et al. | |
| 3,924,633 A | 12/1975 | Cook et al. | |
| 4,037,603 A | 7/1977 | Wendorff | |
| 4,128,100 A | 12/1978 | Wendorff | |
| 4,235,238 A | 11/1980 | Ogiu et al. | |
| 4,392,495 A | 7/1983 | Bayers | |
| 4,441,497 A | 4/1984 | Paudler | |
| 4,509,516 A | 4/1985 | Richmond | |

(Continued)

FOREIGN PATENT DOCUMENTS

AU 278089 B 6/1965

(Continued)

OTHER PUBLICATIONS

Petros, P. E. Papa, "Vault Prolapse II: Restoration of Dynamic Vaginal Supports by Infracoccygeal Sacropexy, an Axial Day-Case Vaginal Procedure", International Urogynecol Journal (2001) vol. 12, pp. 296-303, Springer-Verlag London Ltd.

(Continued)

*Primary Examiner*—John P. Lacyk

(57) ABSTRACT

A mesh, a surgical kit including a mesh, and a method for using the same to restore a prolapsed organ within a patient's pelvic cavity are provided. The surgical kit includes a mesh for supporting the organ including a support sheet portion to be positioned beneath the organ, and first and second front attachment strips extending from a proximal region of the mesh and first and second rear attachment strips extending form a distal region of the mesh. The kit also includes a first guide needle for penetrating tissue to create a passageway through which the attachment strips can be pulled, and coupling means for coupling the ends of the mesh to the attachment strips.

17 Claims, 56 Drawing Sheets

U.S. PATENT DOCUMENTS

| | | | |
|---|---|---|---|
| 4,549,545 A | 10/1985 | Levy | |
| 4,946,467 A | 8/1990 | Ohi et al. | |
| 5,013,292 A | 5/1991 | Lemay | |
| 5,032,508 A | 7/1991 | Naughton et al. | |
| 5,080,667 A | 1/1992 | Chen et al. | |
| 5,112,344 A | 5/1992 | Petros | |
| 5,180,385 A | 1/1993 | Sontag | |
| 5,250,033 A | 10/1993 | Evans et al. | |
| 5,281,237 A | 1/1994 | Gimpelson | |
| 5,337,736 A | 8/1994 | Reddy | |
| 5,362,294 A | 11/1994 | Seitzinger | |
| 5,368,595 A | 11/1994 | Lewis | |
| 5,368,756 A | 11/1994 | Vogel et al. | |
| 5,382,257 A | 1/1995 | Lewis et al. | |
| 5,383,904 A | 1/1995 | Totakura et al. | |
| 5,403,328 A | 4/1995 | Shallman | |
| 5,441,508 A | 8/1995 | Gazielly et al. | |
| 5,450,860 A | 9/1995 | O'Connor | |
| 5,507,796 A | 4/1996 | Hasson | |
| 5,582,188 A | 12/1996 | Benderev et al. | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,741,299 A | 4/1998 | Rudt | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,899,909 A | 5/1999 | Claren et al. | |
| 5,899,999 A | 5/1999 | De Bonet | |
| 5,934,283 A | 8/1999 | Willem et al. | |
| 5,935,122 A | 8/1999 | Fourkas et al. | |
| 5,945,122 A | 8/1999 | Abra et al. | |
| 5,997,554 A | 12/1999 | Thompson | |
| 6,010,447 A | 1/2000 | Kardjian | |
| 6,030,393 A | 2/2000 | Corlew | |
| 6,042,534 A | 3/2000 | Gellman et al. | |
| 6,050,937 A | 4/2000 | Benderev | |
| 6,110,101 A | 8/2000 | Tihon et al. | |
| 6,117,067 A | 9/2000 | Gil-Vernet | |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,334,446 B1 | 1/2002 | Beyar | |
| 6,382,214 B1 | 5/2002 | Raz et al. | |
| 6,406,423 B1 | 6/2002 | Scetbon | |
| 6,475,139 B1 | 11/2002 | Miller | |
| 6,491,703 B1 | 12/2002 | Ulmsten | |
| 6,605,097 B1 | 8/2003 | Lehe et al. | |
| 6,612,977 B1 | 9/2003 | Staskin et al. | |
| 6,691,711 B1 | 2/2004 | Raz et al. | |
| 2001/0018549 A1 | 8/2001 | Scetnpm | |
| 2001/0049467 A1 | 12/2001 | Lehe et al. | |
| 2002/0028980 A1 | 3/2002 | Thierfelder et al. | |
| 2002/0058959 A1 | 5/2002 | Gellmen | |
| 2002/0077526 A1 | 6/2002 | Kammerer et al. | |
| 2002/0091373 A1 | 7/2002 | Berger | |
| 2002/0188169 A1 | 12/2002 | Kammerer et al. | |
| 2003/0004395 A1 | 1/2003 | Therin | |
| 2003/0023138 A1 | 1/2003 | Luscombe | |
| 2003/0149440 A1 | 8/2003 | Kammerer et al. | |
| 2003/0176762 A1 | 9/2003 | Kammerer | |
| 2003/0195388 A1 | 10/2003 | Thierfelder et al. | |
| 2003/0220538 A1 | 11/2003 | Jacquetin | |
| 2004/0039453 A1 | 2/2004 | Anderson et al. | |

FOREIGN PATENT DOCUMENTS

| | | |
|---|---|---|
| AU | 441561 B | 1/1972 |
| DE | 3223153 C1 | 8/1983 |
| DE | 42 20 283 A1 | 12/1993 |
| DE | 4334419 A1 | 4/1995 |
| EP | 0 598 976 A2 | 6/1994 |
| EP | 0 668 056 A1 | 8/1995 |
| EP | 0 774 240 A1 | 5/1997 |
| EP | 0941712 A1 | 9/1999 |
| EP | 1025811 A | 8/2000 |
| GB | 378288 A | 8/1932 |
| SE | 503271 C2 | 4/1996 |
| WO | WO 90/03766 A1 | 4/1990 |
| WO | WO 96/06567 A1 | 3/1996 |
| WO | WO 96/06597 | 3/1996 |
| WO | WO 97/13465 | 4/1997 |
| WO | WO 98/31301 A1 | 7/1998 |
| WO | WO 98/35632 A1 | 8/1998 |
| WO | WO 99/16381 A1 | 4/1999 |
| WO | WO 01/06951 A1 | 2/2001 |
| WO | WO 02/28312 A1 | 4/2002 |
| WO | WO 02/38079 | 5/2002 |
| WO | WO 02/058564 A2 | 8/2002 |
| WO | WO 2004/012626 A1 | 2/2004 |

OTHER PUBLICATIONS

Petros, P. E. Papa, "Vault Prolapse I:Dynamic Supports of the Vagina", International Urogynecol Journal (2001) vol. 12, pp. 292-295, Springer-Verlag London Ltd.

PCT International Search Report, PCT/US03/04181 dated Jul. 8, 2003.

"AMS Sparc™ Sling System", American Medical Systems, Inc., Minnetonka, MN, 2001, pp. 1-7.

"TVT Tension-free Vaginal Tape, Minimally Invasive Highly Effective Treatment for Female Stress Urinary Incontinence", Gynecare, Ethicon, Inc., 1999, pp. 1-6.

Leanza, V. et al. New Technique For Correcting Both Incontinence And Cystocele: T.I.C.T. (Tension-Free Incontinence Cystocele Treatment) Urogynaecologia International Journal, 2001, No. 3515, pp. 133-140.

Collinet, P., et al., "The Vaginal Patch For Vaginal Cure of Cystocele", J. Gynecol. Obstet. Biol. Reprod./vol. 29, No. 2, 2000, pp. 197-201.

Cosson, M. et al., "Cystocele Repair By Vaginal Patch",, Progres en Urologie, 2001, 11, pp. 340-346.

Giberti, Claudio, "Transvaginal Sacrospinous Colpoplexy By Palpation—A New Minimally Invasive Procedure Using An Anchoring System," Urology, 57(4), 666-668 (2001), Elsevier Science Inc., Ospedale.

European Supplementary Search Report dated Aug. 2, 2004, for corresponding EP application 02776559.3.

Supplementary Partial European Search Report dated Sep. 23, 2004, for corresponding EP application 00928947.1.

Norris et al., "Use of Synthetic Material in Sling Surgery: A Minimally Invasive Approach", Journal of Endourology, vol. 10, No. 3, Jun. 1996, pp. 227-230.

O'Donnell, "Combined Raz Urethral Suspension and McGuire Pubovaginal Sling for Treatment of Complicated Stress Urinary Incontinence", Journal of the Arkansas Medical Society, vol. 88, No. 8, Jan. 1992, pp. 389-392.

Staskin et al, "The Gore-tex sling procedure for female sphincteric incontinence: indications, technique, and results", World Journal Urol., vol. 15, 1997, pp. 295-299.

EP communication dated Sep. 13, 2005, for corresponding EP application 00928947.1.

EP Search Report dated Sep. 14, 2005, for corresponding EP application 04078476.1.

U.S. Appl. No. 09/716,546, Ethicon, Inc.

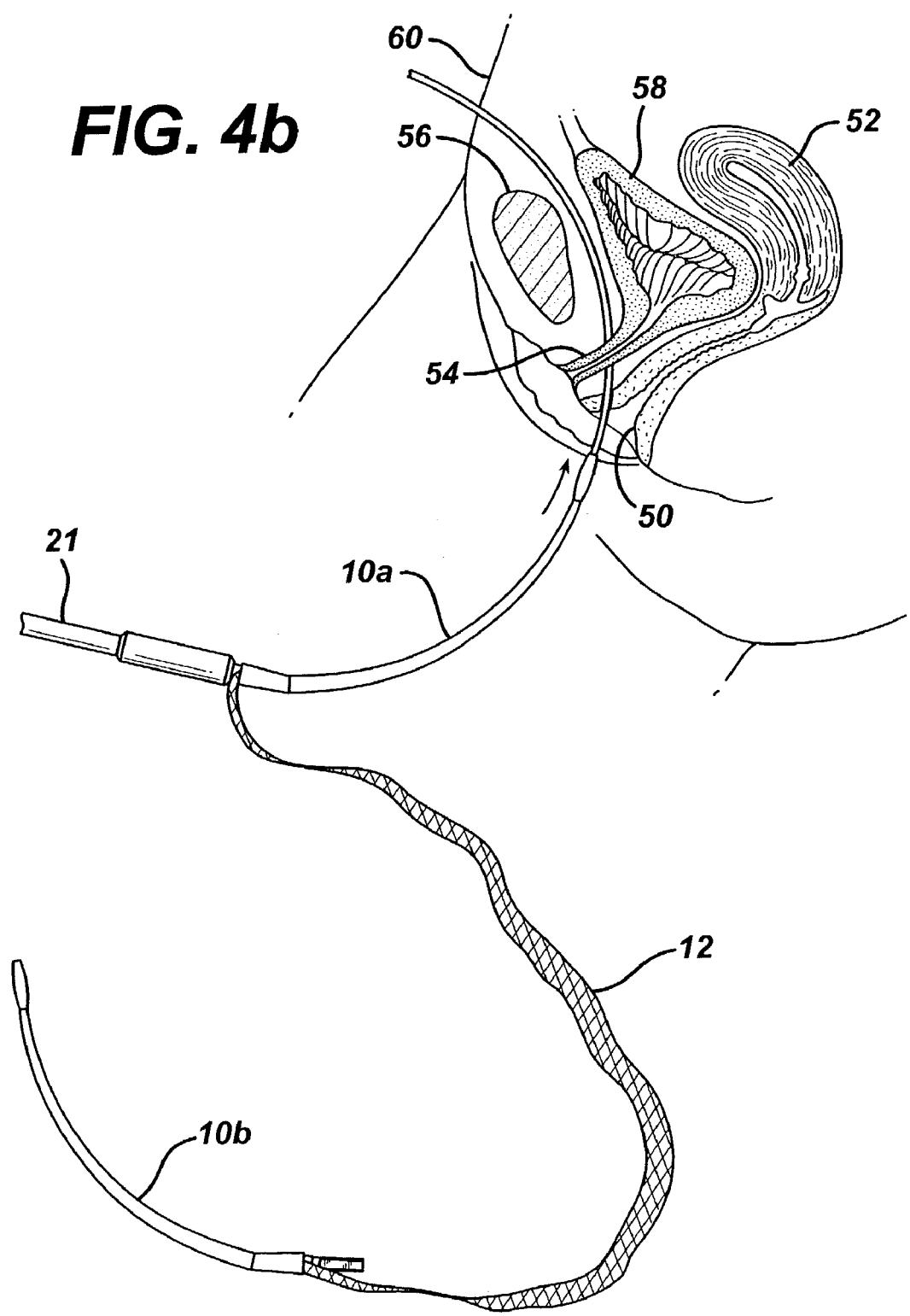

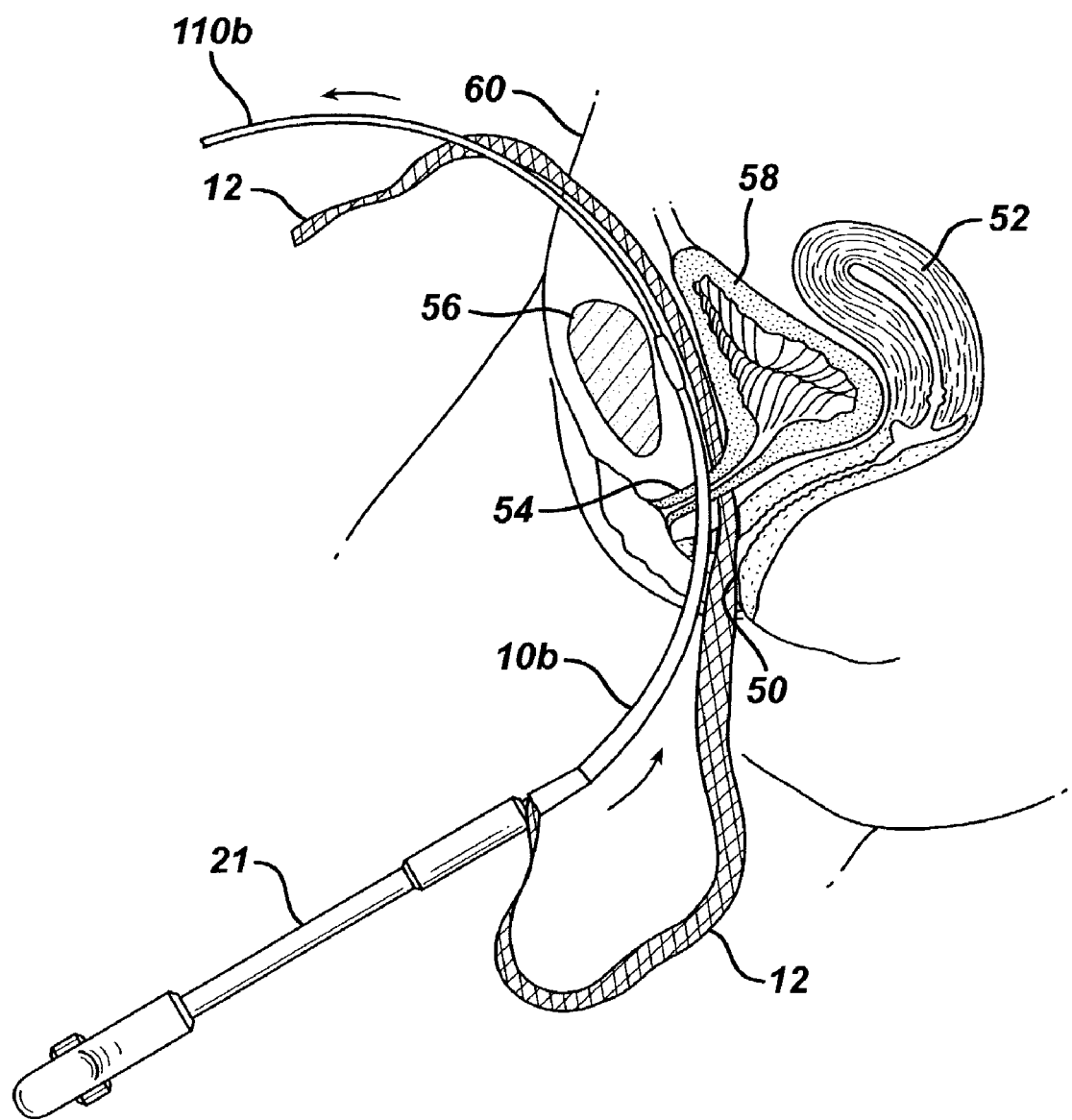

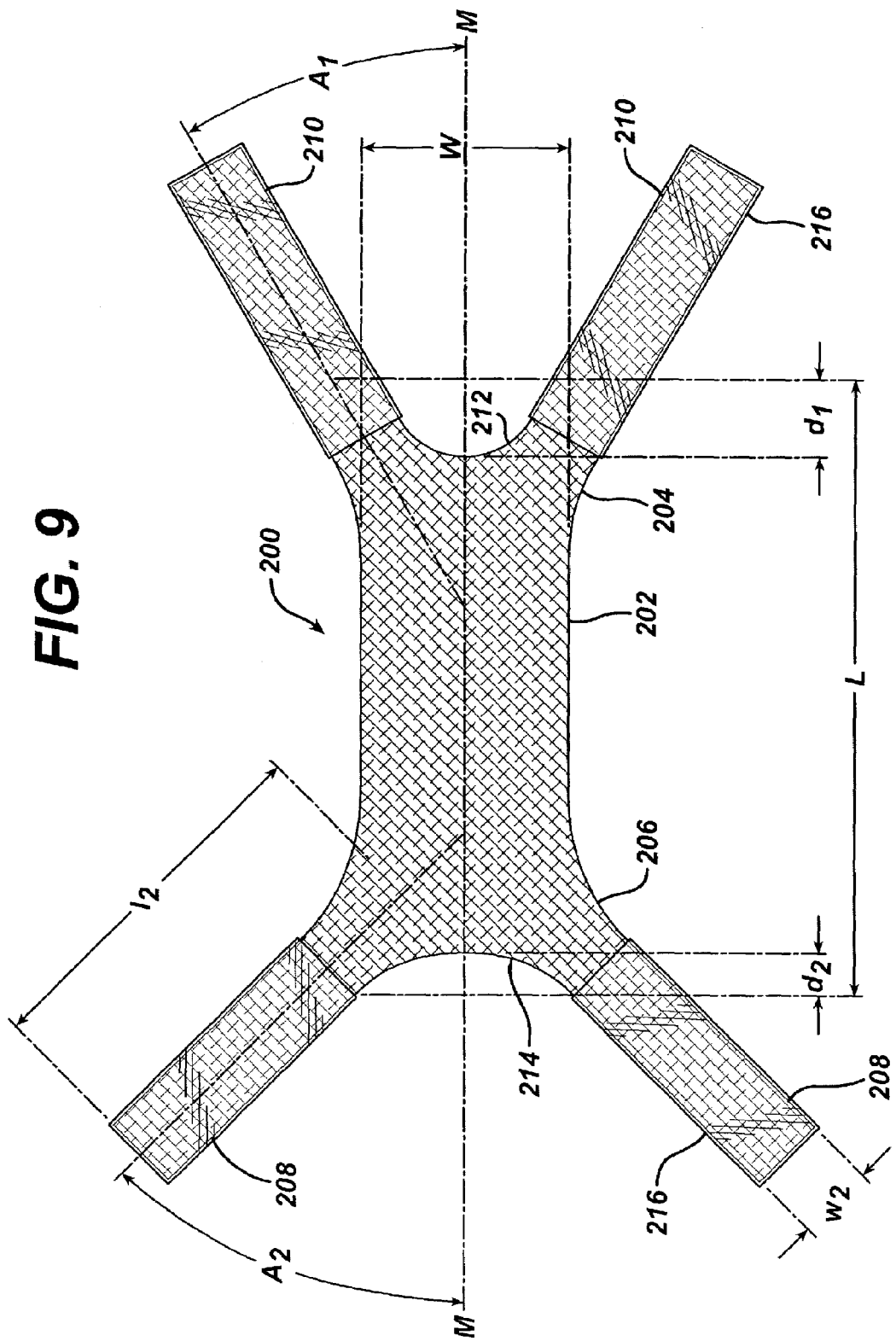

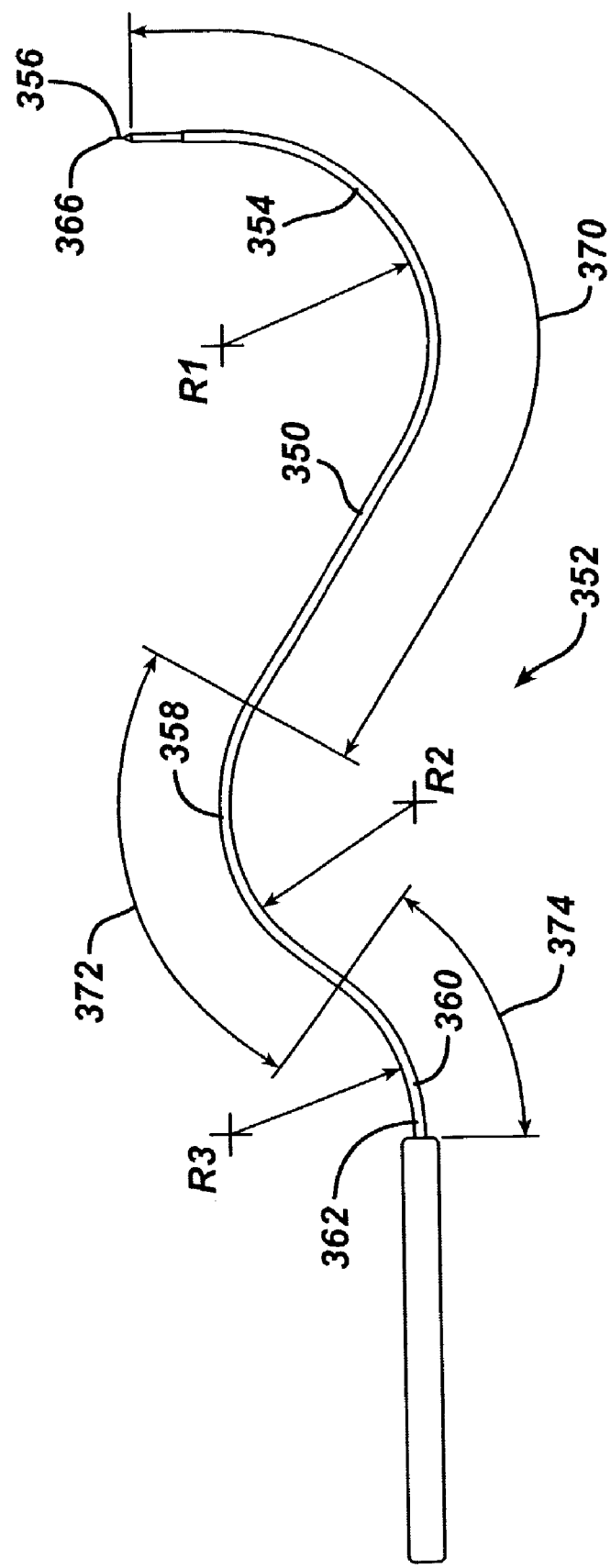

SURGICAL INSTRUMENT AND METHOD FOR TREATING ORGAN PROLAPSE CONDITIONS

CROSS REFERENCE TO RELATED APPLICATION

The present invention is a continuation-in-part of co-pending U.S. patent application, Ser. No. 10/191,572, filed on Jul. 9, 2002, which is a continuation of co-pending U.S. patent application Ser. No. 09/873,571, filed on Jun. 4, 2001, which is a continuation-in-part of Ser. No. 09/521,801 filed Mar. 09, 2000 now U.S. Pat. No. 6,273,852. The present invention also claims the benefit of earlier filed U.S. provisional patent application, Ser. No. 60/356,697, filed on Feb. 14, 2002.

BACKGROUND OF THE INVENTION

1. Field of the Invention

The present invention relates generally to surgical instruments and a methods, and surgical kits for treatment of pelvic floor prolapse conditions.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise. SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape.

U.S. Pat. No. 5,899,909, which is incorporated herein by reference in its entirety, discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare Worldwide, a division of Ethicon Inc., of Somerville, N.J., USA. In this procedure two 5 mm needles pass a PROLENE® mesh trans-vaginally and through the abdomen to create a tension-free support around the mid urethra.

An alternate method to treat SUI is the sling procedure. In this procedure a needle or other suture-retrieving device is first inserted through the abdomen, above the pubic bone. The needle is guided behind the pubic bone, through the subrapubic fascia around the urethra, and out of the body through an incision in the anterior vaginal wall. At this point sutures are attached to the needle(s) and pulled up back through the abdominal cavity, where the sutures are fastened to the rectus muscle.

Techniques for protecting against the puncture of the internal structures during this type of procedure have included laparoscopic procedures. This involves making an incision in the abdomen and inserting a video scope to watch the progress of the needles as they pass through the abdominal cavity. These additional incisions are not optimal for the patient. Also, the needles, which pass through the abdomen, are not designed to capture a mesh but rather a suture, which has been previously attached to the mesh or harvested fascia. These needles are generally in the diameter range of about 0.090 inches to about 0.120 inches. Therefore, the needles do not create a large channel through the fascia. The channel is only wide enough to pass the suture. Accordingly, the sutures do not possess the elongation properties of the PROLENE® mesh and therefore cannot provide the tension-free support of the TVT. Also, attaching a mesh directly to these needles is not optimal because it is very difficult, if at all possible, to pull the mesh through the narrow channel created by the needle.

Another common condition suffered by women is prolapse of organs within the pelvic cavity. Prolapse is a condition in which organs, namely the bladder, bowel, and uterus, which are normally supported by the pelvic floor, herniate or protrude into the vagina. This occurs as a result of weakening or damage to the muscles and ligaments making up the pelvic floor support. Childbirth is the most common cause of damage to the pelvic floor, particularly where prolonged labor, large babies and instrumental deliveries were involved. Other factors can include past surgery such as hysterectomy, lack of estrogen due to menopause, and conditions causing chronically raised intra abdominal pressure such as chronic constipation, coughing, heavy lifting, and other physical activity involving impact with the body, such as skydiving. Specific prolapse conditions include cystocele, which is a prolapse of the bladder, rectocele or rectal prolapse, enterocele or intestinal herniation, and prolapse of the vaginal vault such as after a hysterectomy.

Vaginal surgery is the usual method of repair, but abdominal surgery (typically laparoscopc surgery) may also be performed. Traditional pelvic floor repair surgeries, whether abdominal or vaginal, involve lifting the prolapsed organ to restore it back to its correct anatomical position, and subsequently using sutures attached to ligaments and/or muscles to retain the organ in the correct position. Surgeons have also been known to place a layer of mesh below the prolapsed organ, and to subsequently suture corners or sides of the mesh to ligaments or muscles on the sidewalls of the pelvis. The suturing can be done via access through the abdomen or by access through the vaginal incision. Using sutures to support the mesh structure has disadvantages similar to those described above in conjunction with SUI procedures.

The device and method disclosed in patent application WO 02/38079 provides an improvement over the traditional pelvic floor repair surgery discussed above. WO 02/38079 discloses a specific mesh configuration for use in treating both cystocele and SUI that includes a basic mesh structure with two front and two rear supports that extend outwardly therefrom. The supports are thin strips of mesh that provide support to the prolapsed organ in place of sutures. In particular, WO 02/38079 describes using the instrument for treating SUI described in WO 96/06567 and 97/13465, which are incorporated herein by reference in their entirety, and the method described therein, to pass the mesh strips through the body. The described needles are used to pass the mesh strips from the vaginal incision up through the abdomen. One pass is made with a needle coupled to both the front and rear strips on one side, and then another pass is made for the front and rear strips on the other side. Thus, the front and rear strip on a given side are coupled to a needle together, and passed through the same channel out through the abdomen. As a result of both the front and back strips being attached at the same point, some additional stabilization is required to prevent forward movement of the basic structure, with suturing being the disclosed means by which to achieve this stabilization.

As with the traditional pelvic floor repair procedures, the procedure described in WO 02/38079 requires extensive, deep suturing skills in tight spaces, which are difficult to perform and time consuming. Sutures provide for only a "pin point" attachment of the mesh in place, and failures between the suture and the mesh are not uncommon. In addition, the single point of attachment of both mesh strips significantly limits the adjustability of urethral suspension versus bladder suspension. In particular, if tension free suspension of the urethra is achieved, further adjustment of the bladder suspension strips (rear strips) can adversely affect the urethral suspension, and vice versa. Finally, the vaginal approach of WO 02/38079 is disadvantageous in that suspension of the rear strip is limited to the same path as that of the front strip, as any other pathway would be potentially dangerous to vital organs and nerves via such a blind approach.

Accordingly, it would be beneficial to provide an improved surgical system and method for pelvic floor repair.

SUMMARY OF THE INVENTION

The present invention provides a surgical kit for performing a surgical procedure on a patient to restore a prolapsed organ within a patient's pelvic region. The surgical kit includes a mesh for supporting the organ, the mesh including a support sheet portion to be positioned substantially beneath the organ having a distal end region and a proximal end region, first and second front attachment strips extending from the proximal end region, and first and second rear attachment strips extending from the distal end region. The surgical kit further includes a first guide needle for penetrating tissue within the patient's body to create a passageway through the patient's pelvic region through which the first or second front or rear attachment strips can be pulled. The guide needle has a proximal end and a tissue penetrating blunt tip at a distal end, and defines in part a curved shaft having a first curvature. Also included is a coupling means for coupling a distal end of each of the first and second front and rear attachment strips to the distal end of the guide needle.

According to one embodiment, for each of the first and second front and rear attachment strips, the coupling means is a coupling element fixedly secured at a first end to a distal end of the attachment strips, and having an opening at a second end dimensioned to receive therein and securely engage the distal end of the guide needle. In another embodiment the coupling element can be detachably coupled to the distal end of the guide needle.

In another alternate embodiment, for each of the first and second front and rear attachment strips, the coupling means includes a needle element fixedly coupled at a proximal end to a distal end of the attachment strip, and a coupling device for coupling a distal end of the needle element to the distal end of the guide needle. The coupling device of this embodiment may further include a first opening at a first end dimensioned to receive therein and securely engage the distal end of the needle element and a second opening at a second end dimensioned to receive therein and securely engage the distal end of the guide needle.

In another embodiment of the surgical kit, the distal end region of the support sheet portion has a recess therein between the first and second rear attachment strips, and in yet another embodiment, the proximal end region of the support sheet portion also has a recess therein between the first and second front attachment strips.

In yet another embodiment, the first and second front and rear attachment strips extend outwardly from the proximal and distal end regions respectively at an angle of approximately 30–60 degrees relative to a midline of the mesh. In yet another embodiment, the first and second rear attachment strips extend outwardly from the distal end region at an angle of approximately 40 degrees relative to the midline of the mesh, and the first and second front attachment strips may extend outwardly from the proximal end region at an angle of approximately 60 degrees relative to the midline of the mesh.

In another embodiment, the surgical kit further includes a second guide needle for penetrating tissue within the patient's body to create a passageway through the patient's pelvic region through which the first or second front or rear attachment strips can be pulled, the guide needle having a proximal end and a tissue penetrating blunt tip at a distal end and defining in part a curved shaft. The curved shaft of the second guide needle may have a curvature different than that of the first guide needle, and the passageway created by the first guide needle may be different than that of the second guide needle.

According to yet another embodiment, the organ is the patient's bladder, and the curvature of the first guide needle is such it can extend from an exterior of the abdomen, around the pubic bone, and into the vagina. In yet another embodiment, the curvature of the second guide needle is such that it can extend from an exterior of the abdomen at a location caudal and lateral to that of the first guide needle, around the side of the bladder, and out into the vagina. In yet another embodiment, the curvature of the second guide needle forms a compound curve.

In yet another embodiment, for each of the first and second front and rear attachment strips, a removable sheath substantially covers the attachment strip.

A mesh is also provided for supporting a prolapsed bladder, which includes a support sheet portion to be positioned substantially beneath the bladder having a distal end region and a proximal end region. The proximal end region has a first recess therein and the distal end region has a second recess therein so that, when the mesh is positioned within a patient's body, the proximal end region is positioned substantially under the bladder with the bladder neck positioned substantially within the first recess, and the distal end region is positioned under a posterior end of the bladder with the second recess positioned above the apex of the vagina and/or proximal of the cervix. The mesh also includes first and second front attachment strips that extend from the proximal end region at an angle of between approximately 30 and 60 degrees relative to a midline of the mesh, and first and second rear attachment strips that extend from the distal end region at an angle of between approximately 30 and 60 degrees relative to the midline.

In another embodiment, the mesh further includes, for each of the first and second front and rear attachment strips, a removable sheath substantially covering the attachment strip.

In one embodiment, the first and second front attachment strips extend from the proximal end region at an angle of approximately 60 degrees relative to the midline, and in yet another embodiment, the first and second rear attachment strips also extend from the proximal end region at an angle of approximately 40 degrees relative to the midline.

According to another embodiment, the mesh further includes coupling elements coupled to a distal end of each of the first and second front and rear attachment strips. The coupling elements each further have a means for attaching to the distal end of a guide needle to couple it thereto, and each are dimensioned to pass through a passageway through the patient's body created by the guide needle.

A method is also provided for restoring a prolapsed organ within a patient's pelvic cavity. The method includes the steps of providing a mesh for supporting the prolapsed organ, the mesh including a support sheet portion to be positioned substantially beneath the organ having a distal end region and a proximal end region. First and second front attachment strips extend from the proximal end region of the mesh, and first and second rear attachment strips extend from the distal end region of the mesh. The method further includes the steps of, for each of the first and second front and rear attachment strips, using the guide needle to create a passageway through the patient's body from an exterior of the body and into the patient's vagina, coupling the guide needle to a distal end of the attachment strip using a coupling means, and retracting the guide needle and attached attachment strip through the body through the passageway; adjusting the mesh using ends of the attachment strips so that the mesh supports the prolapsed organ; removing a portion of the attachments strips that are outside of the body; and leaving the mesh and remaining attachment strips within the body.

According to one embodiment, for the first and second front attachment strips, the passageway through the patient's body extends from an exterior of the abdomen, around the pubic bone and out of the vagina, on first and second sides of the bladder respectively. In yet another embodiment, for the first and second rear attachment strips, the passageway through the patient's body extends from an exterior of the abdomen at a location caudal and lateral to the location of the first and second front attachment strips, around the bladder and out through the vagina, on first and second sides of the bladder respectively. In an alternate embodiment, for the first and second front attachment strips, the passageway through the patient's body extends from an exterior of the medial side of the hip, through the obturator fossa, around the obturator bone, and out thought the vagina, on first and second sides of the bladder respectively.

In yet another embodiment, a first guide needle is used to create the passageway for the first and second front attachment strips, and a second guide needle is used to create the passageway for the first and second rear attachment strips, and the first guide needle has a curvature different than the second guide needle.

In another embodiment, for each of the first and second front and rear attachment strips, the coupling means is a coupling member fixedly secured at one end to a distal end of the attachment strip, and having an opening at a second end for receiving therein and securely engaging a distal end of the guide needle. In an alternate embodiment, for each of the first and second front and rear attachment strips, the coupling means comprises a needle element fixedly attached at a proximal end to a distal end of the attachment strip, and a coupling device for coupling the distal end of the needle element with the distal end of the guide needle. The coupling device may further have an opening at a first end for receiving therein and securely engaging the distal end of the needle element, and an opening at a second end for receiving therein and securely engaging the distal end of the guide needle.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3b–d are alternate embodiments of a connector for use in FIG. 3a;

FIGS. 4a–j diagrammatically illustrate several surgical steps of a trans-abdominal method utilizing two needles and guide needle according to the invention to treat SUI;

FIGS. 8a–i diagrammatically illustrate several surgical steps of a trans-abdominal method utilizing two needles and two guide needles according to the invention to treat SUI;

FIG. 9 is a plan view illustrating one embodiment of a mesh for use in treating pelvic floor prolapse;

FIG. 13 is a side view of another embodiment of a surgical guide needle that can be used for placing a mesh for treating pelvic floor prolapse;

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways.

The invention discloses an apparatus and method for treating SUI. A mesh or tape is passed through pelvic tissue and positioned between the urethra and vaginal wall, creating a supportive sling. The mesh provides a structure means for tissue in growth and thereby provides a newly created body tissue supporting means for the urethra. When pressure is exerted upon the lower abdomen, such as during a cough or sneeze, the mesh provides support to the urethra, allowing it to keep its seal and prevent the unwanted discharge of urine.

Figure 1:
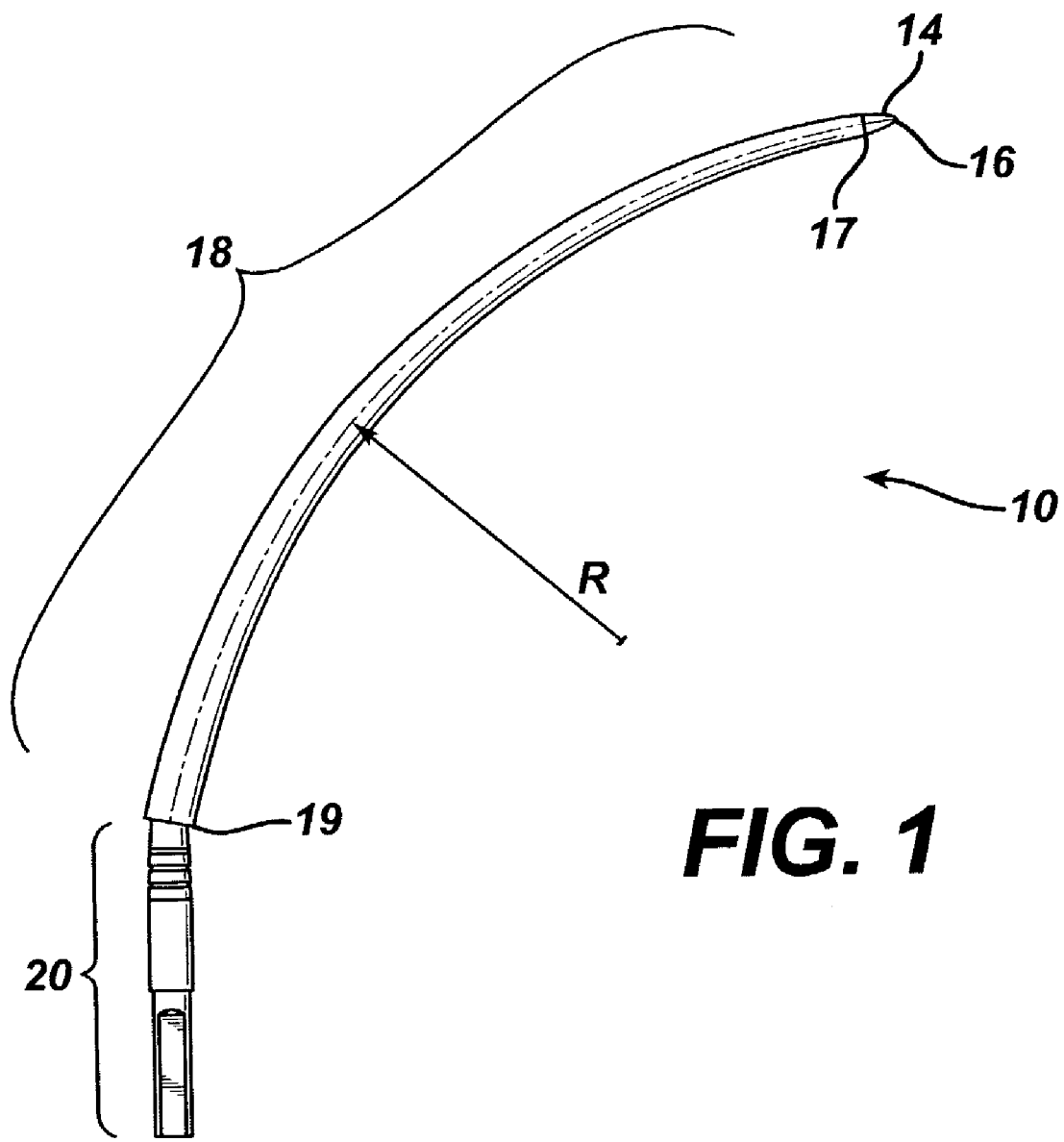
FIG. 1 is a side view of the needle in one embodiment thereof.
Figure 2A:
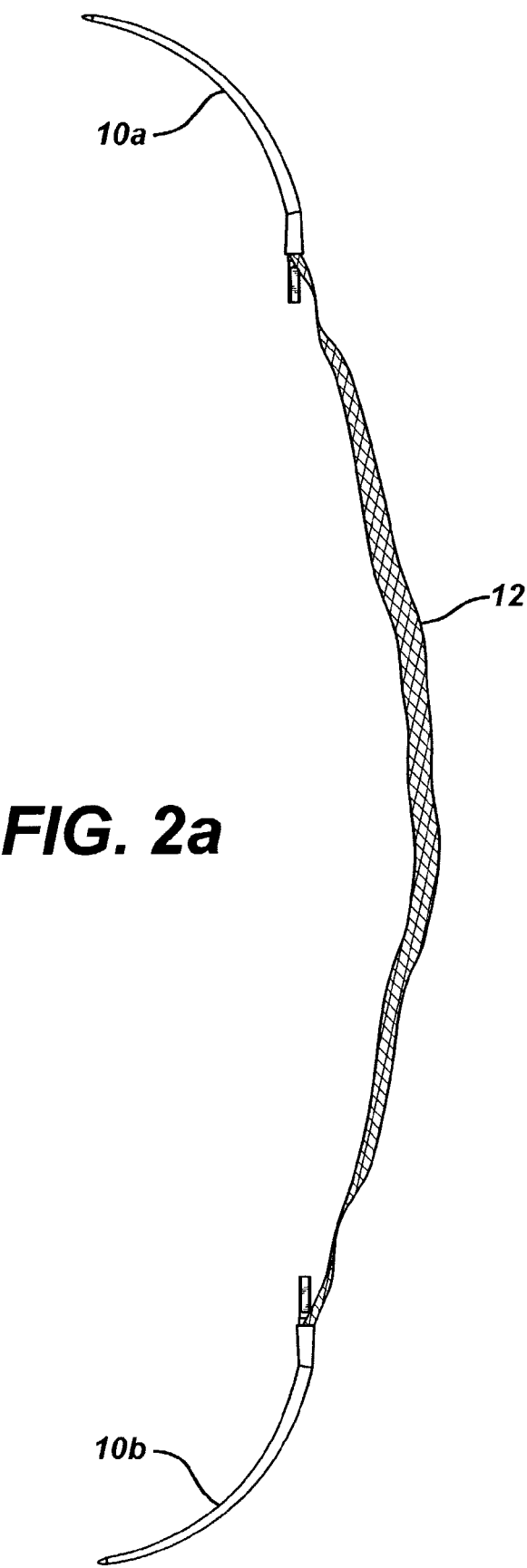
FIG. 2a is a side view of two needles and a mesh interconnecting the needles.

Referring to FIGS. 1 and 2a, in one embodiment the surgical instrument comprises a needle-like element 10 that attaches to a mesh 12. Needle element 10 defines a certain radius R to perform the surgical procedure discussed herein. The distal end of needle element 10 terminates at a conical section 14 having a tip 16. Alternate configurations, such as a blade-like, arrow or burr tips are, also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the mesh as described below.

The proximal end of needle 10 terminates in an attachment segment 20 that is adapted to mate and lock into a handle 21 as disclosed in U.S. Pat. No. 5,899,909.

Disposed between tip 14 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of shaft 18 may be constant, for example, about 5 mm. Alternatively, the diameter of segment 18 may transition from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm.

Needle 10 is preferably tubular with a circular cross section and is made from a material that is compatible with the human body. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the mesh 12. The surface of needle 10 may also be darkened in shade or color to provide higher visibility while in place in the body during a cystoscopy.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
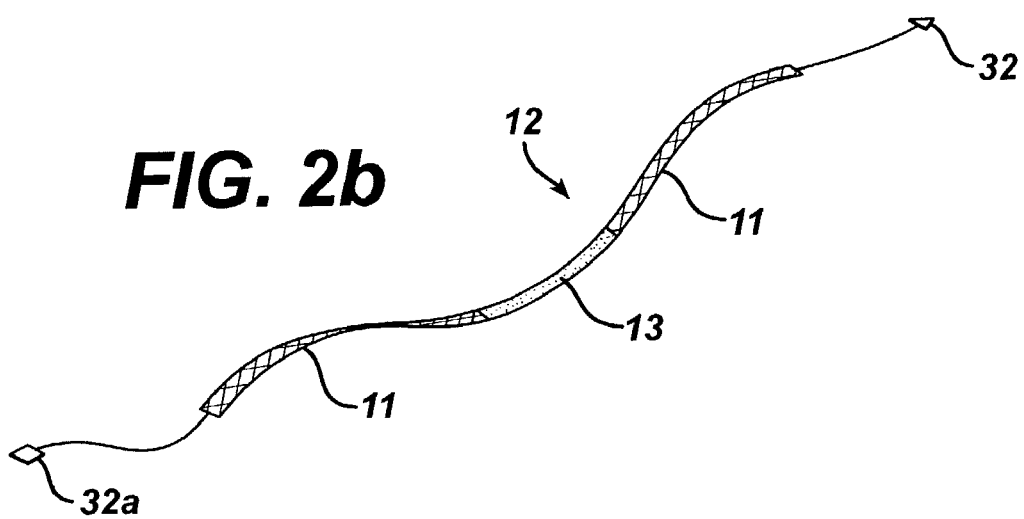
FIGS. 2b–d are alternate embodiments of the mesh and connecting means between the mesh and needle.
Figure 2C:
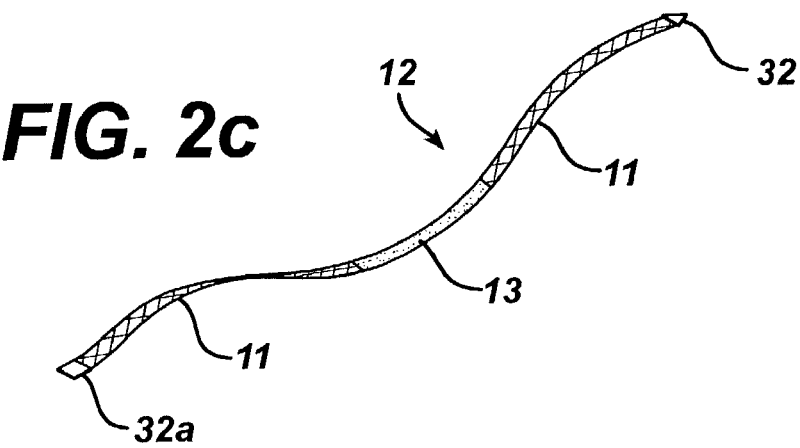
Figure 2D:
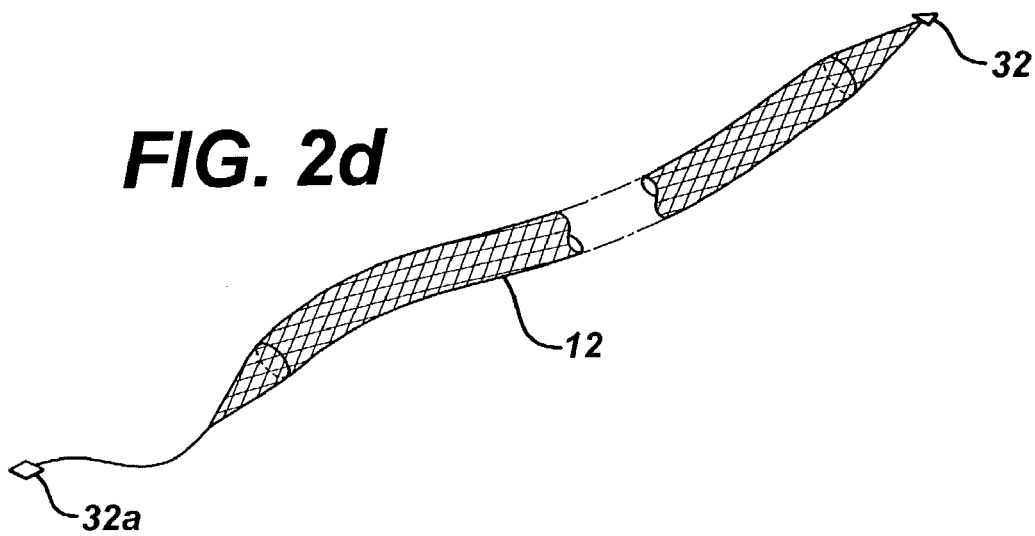

Referring to FIGS. 2a–d, mesh 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the mesh 12 is a combination of a synthetic material 11 and a natural material 13 centered between the synthetic material 11 as shown in FIGS. 2b–c. A still further embodiment of the mesh 12 includes a combination of synthetic material 11 and natural material 13, whereby the natural material is placed over or incorporated within a generally central portion of the synthetic material 11. One advantage of the mesh configurations is that natural material 13 is along the center region of mesh 12 so that after installation of mesh 12, natural material 13 is positioned below the urethra and eliminates possible erosion issues at the interface of the urethra and mesh. Natural material 13 may be connected to the synthetic material 11 by means of sewing, a biocompatible glue, cell culturing techniques or other known means.

Mesh 12 may be of any convenient shape that suits the intended purpose of the invention. An exemplary width is about 1 cm and the length would be dependent upon the size of the female undergoing the procedure. Mesh 12 may be single or double ply, generally planar in structure, or tubular (FIG. 2d) to provide additional supporting strength and more surface area on which tissue fibers may attach. Moreover, mesh 12 may consist of different types of material, such as a bioabsorbable and non-bioabsorbable material. Mesh 12 may also be coated with an antimicrobial additive to prevent or minimize infection and a lubricous coating, for example, a bioabsorbable hydrogel, to facilitate the mesh passing through the tissue as discussed below. Preferably, mesh 12 is covered by a removal plastic sheath as disclosed in U.S. Pat. No. 5,899,909. The mesh may also be made radio-opaque and/or of a contrasting color to the body tissue to allow for future diagnostic visualization.

In one embodiment mesh 12 may be attached to needle segment 20 by means of tying, gluing or other suitable attaching means. Preferably, a biocompatible heat shrink tube fixes mesh 12 onto needle portion 20, FIG. 2a.

Figure 3A:
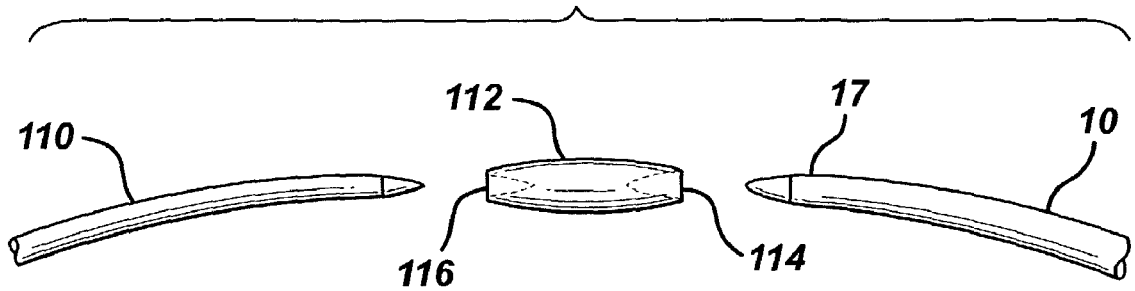
FIG. 3a is an assembly diagram for two needles and a connector.

FIG. 3a illustrates a needle 10 for use in conjunction with a guide needle 110 and coupler 112. Guide needle 110 may be configured to have a similar radius R as needle 10. Preferably, guide needle 110 has a smaller diameter, about 2 mm. It is possible, however, for guide needle 110 to have the same diameter as needle 10. A coupler 112 acts as an interfacing element useful to couple guide needle 110 to needle 10. Coupler 112 is substantially elliptical-shaped having a first bore opening 114 for accepting distal end 17 and a second bore opening 116 for accepting the distal end of guide needle 110. Preferably, openings 116 and 114 are configured to allow for a press fit connection with needles 110 and 10, respectively. Alternatively, openings 114 and 116 may comprise a biocompatible glue or high-friction material to facilitate a strong connection between the needles 10/110 and coupler 112. Coupler 10 may be made from any biocompatible metal, such as stainless steel or polyurethane, silicone, rubber or other similar compound.

Figure 3B:
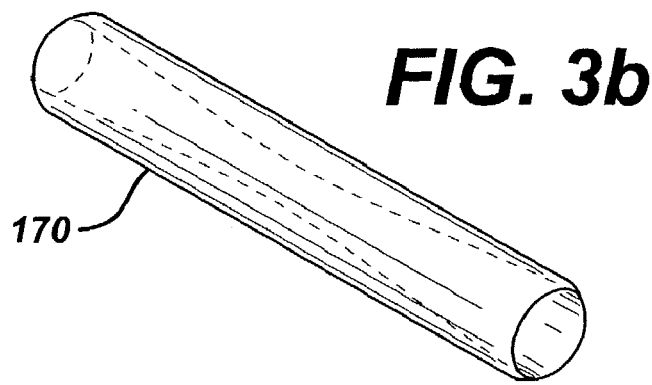
Figure 3C:
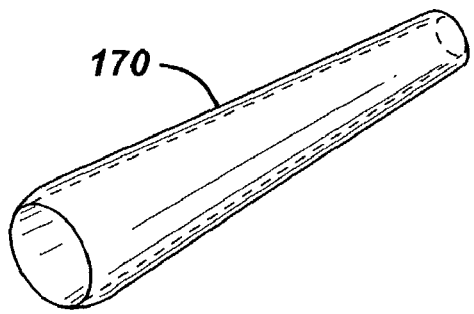
Figure 3D:
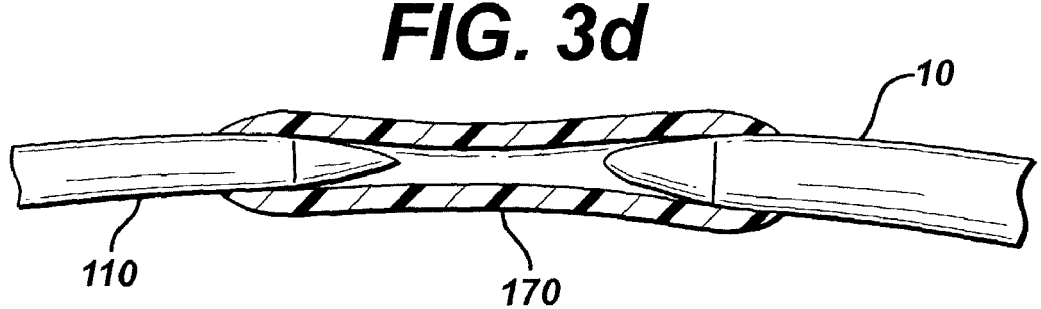
Figure 4A:
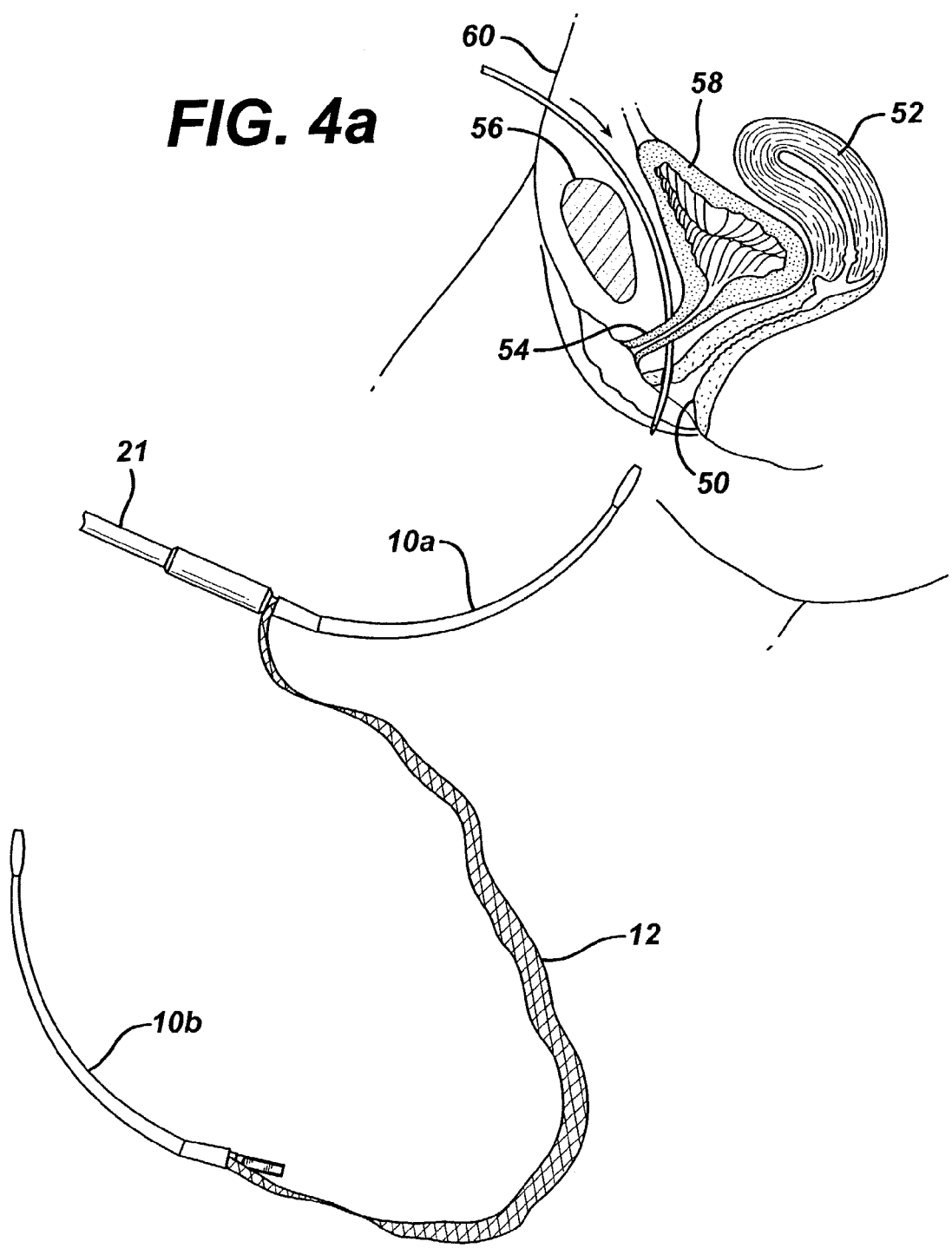
Figure 4C:
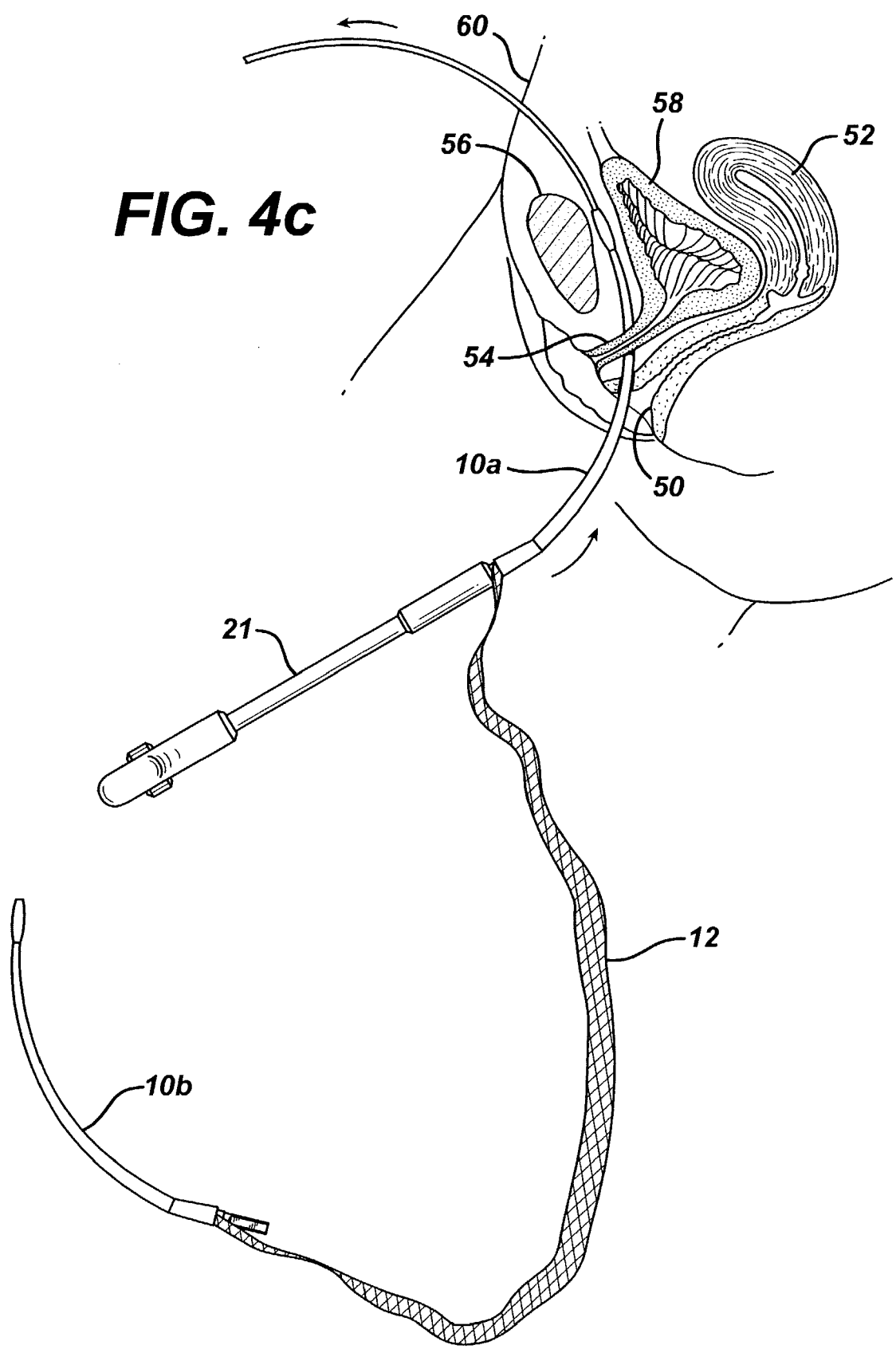
Figure 4D:
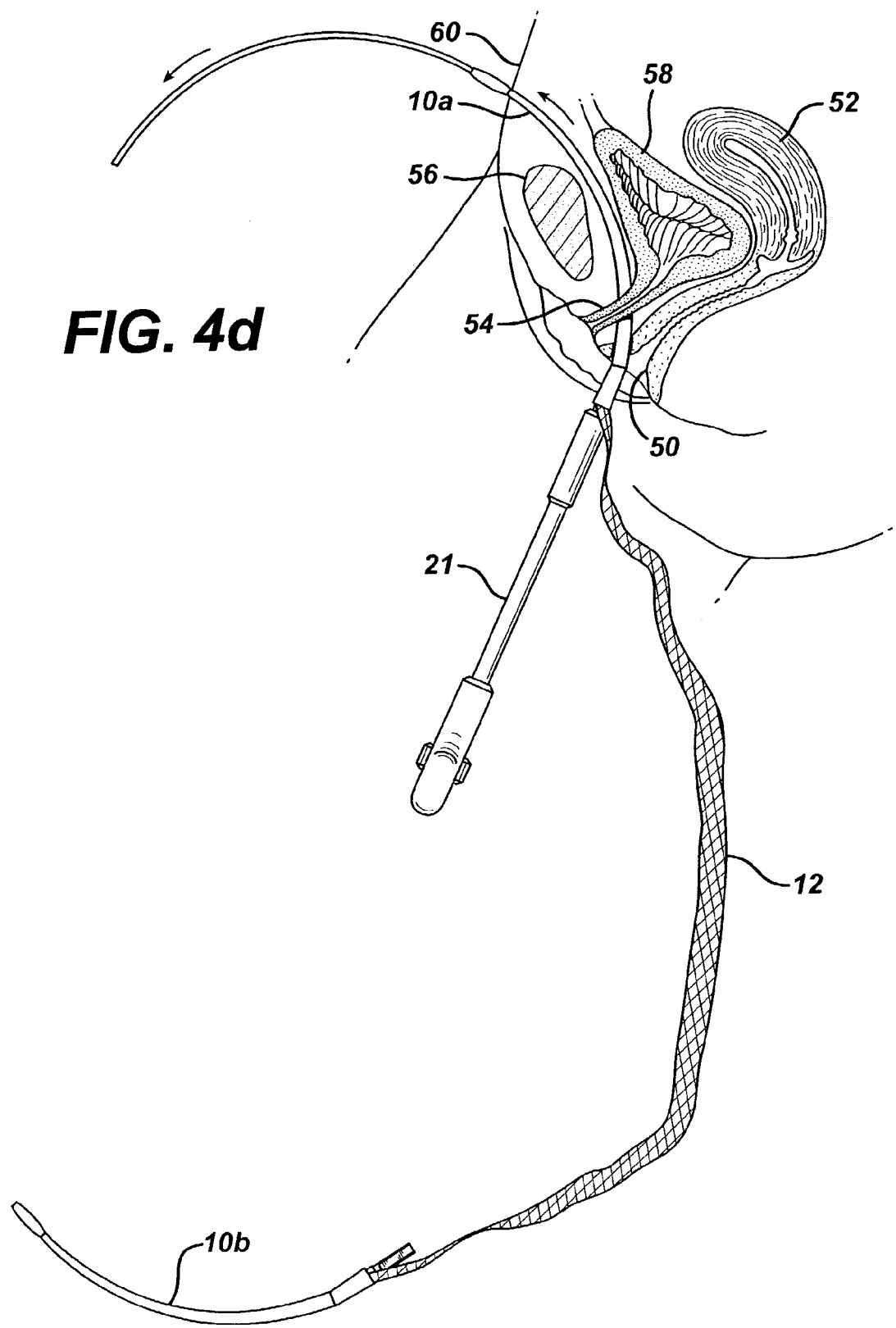
Figure 4E:
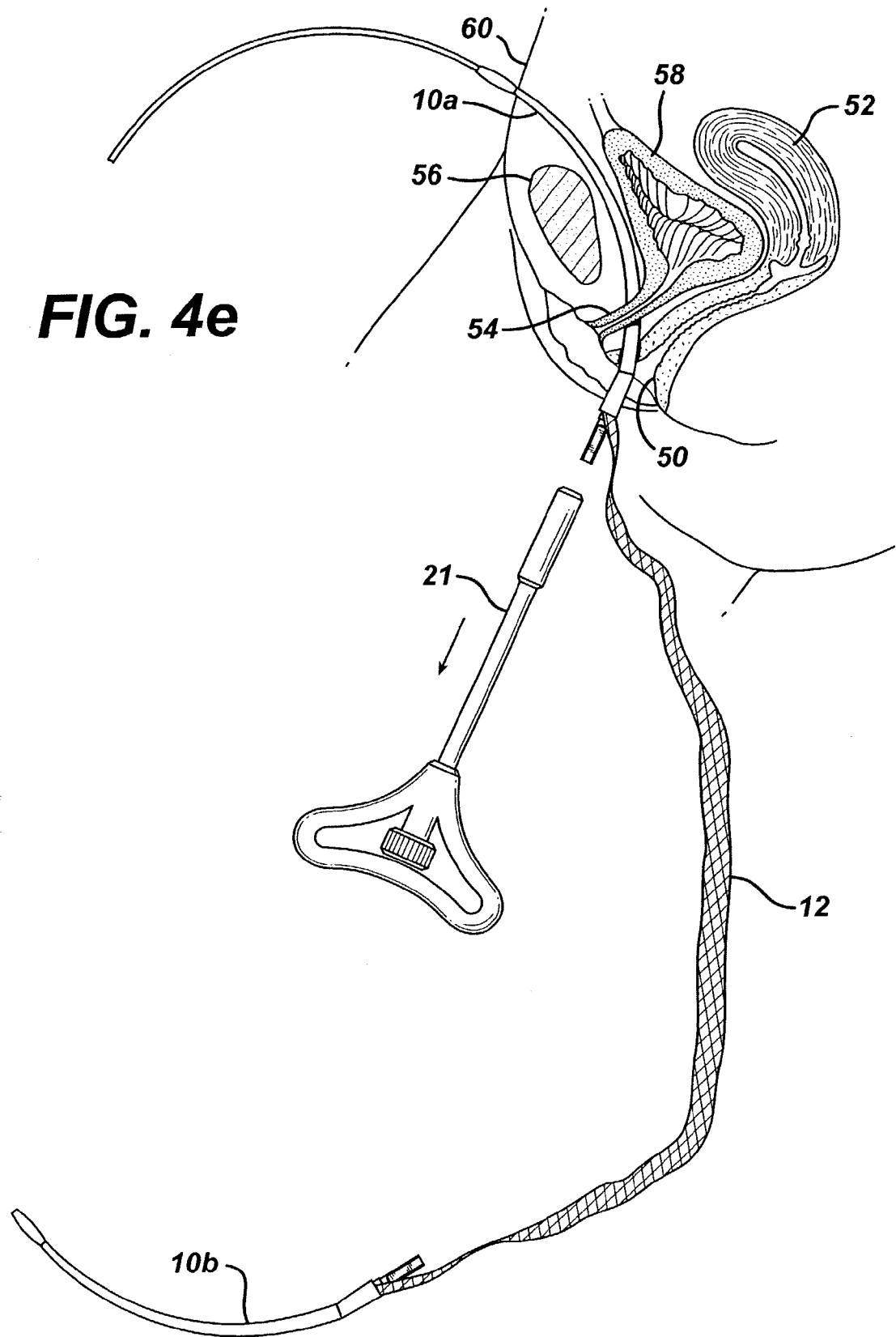
Figure 4F:
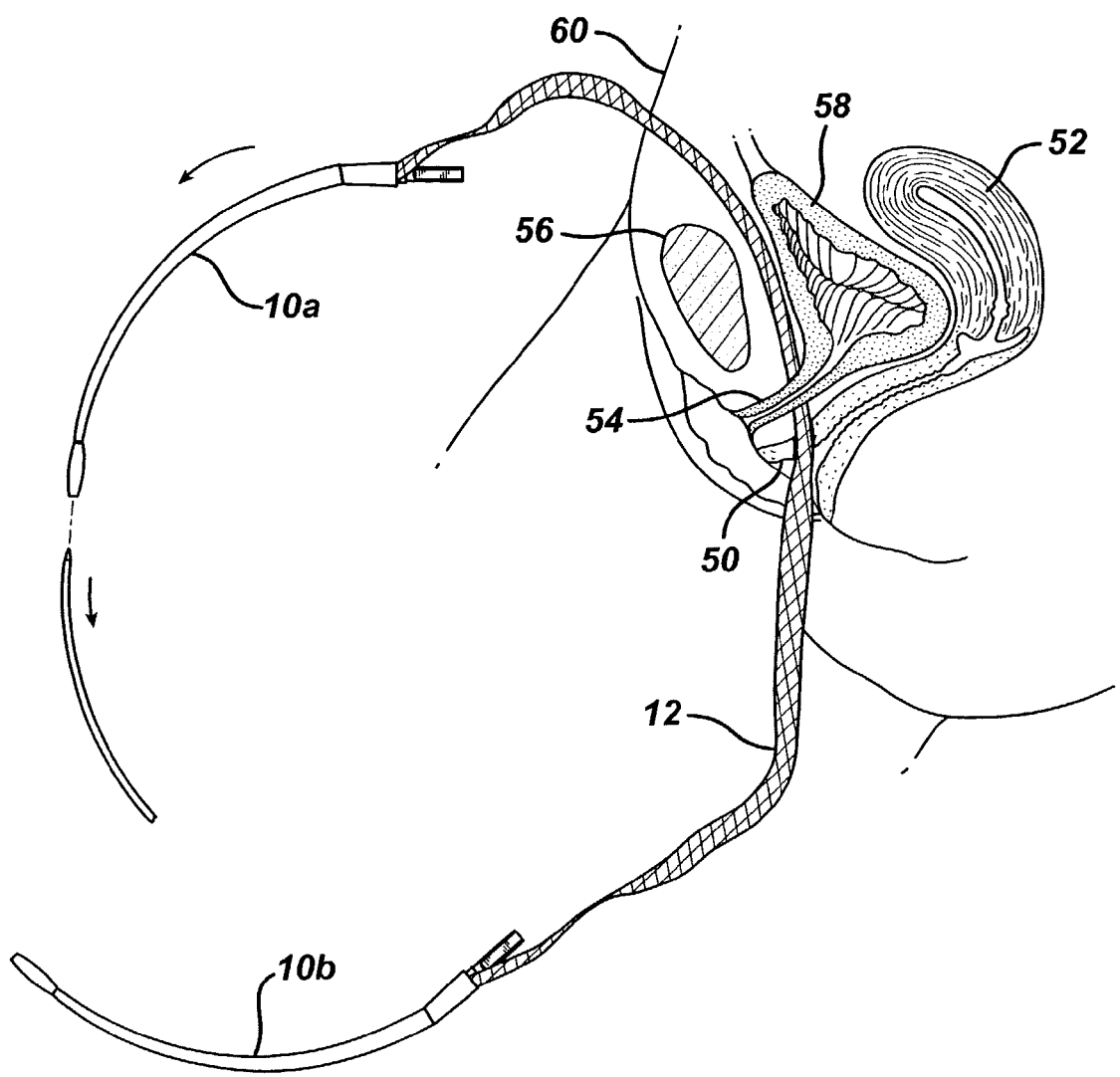
Figure 4G:
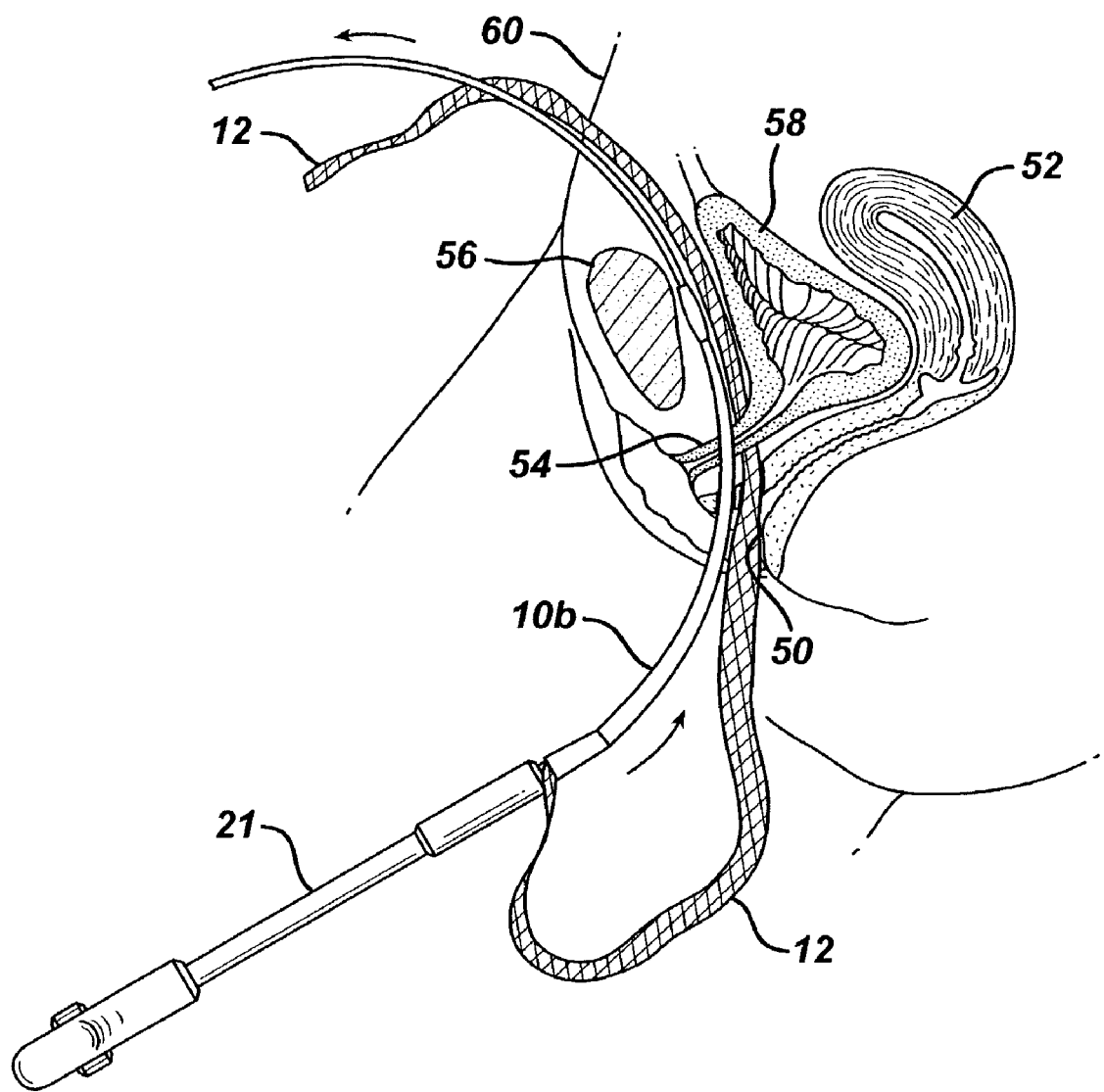
Figure 4H:
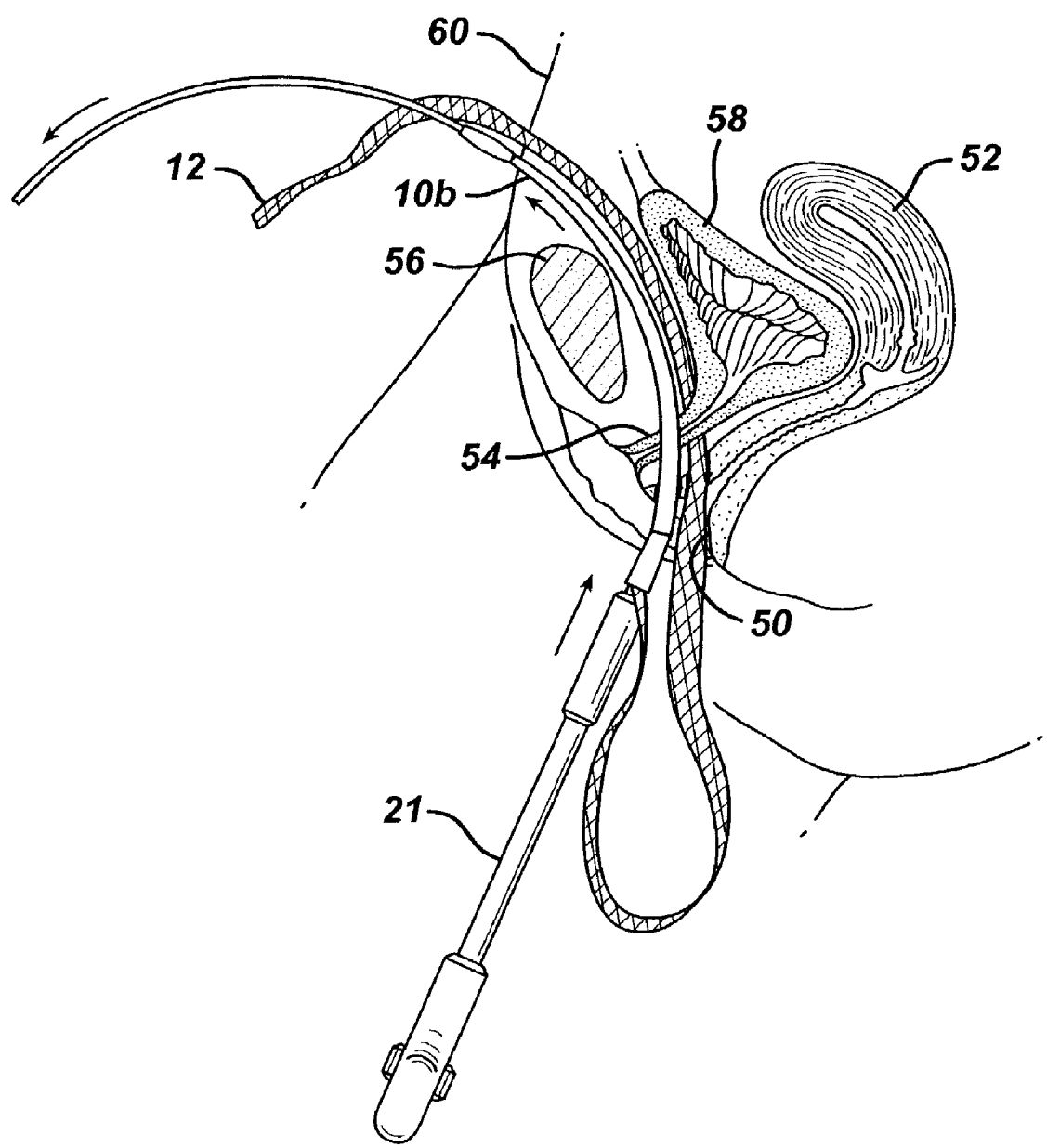
Figure 4I:
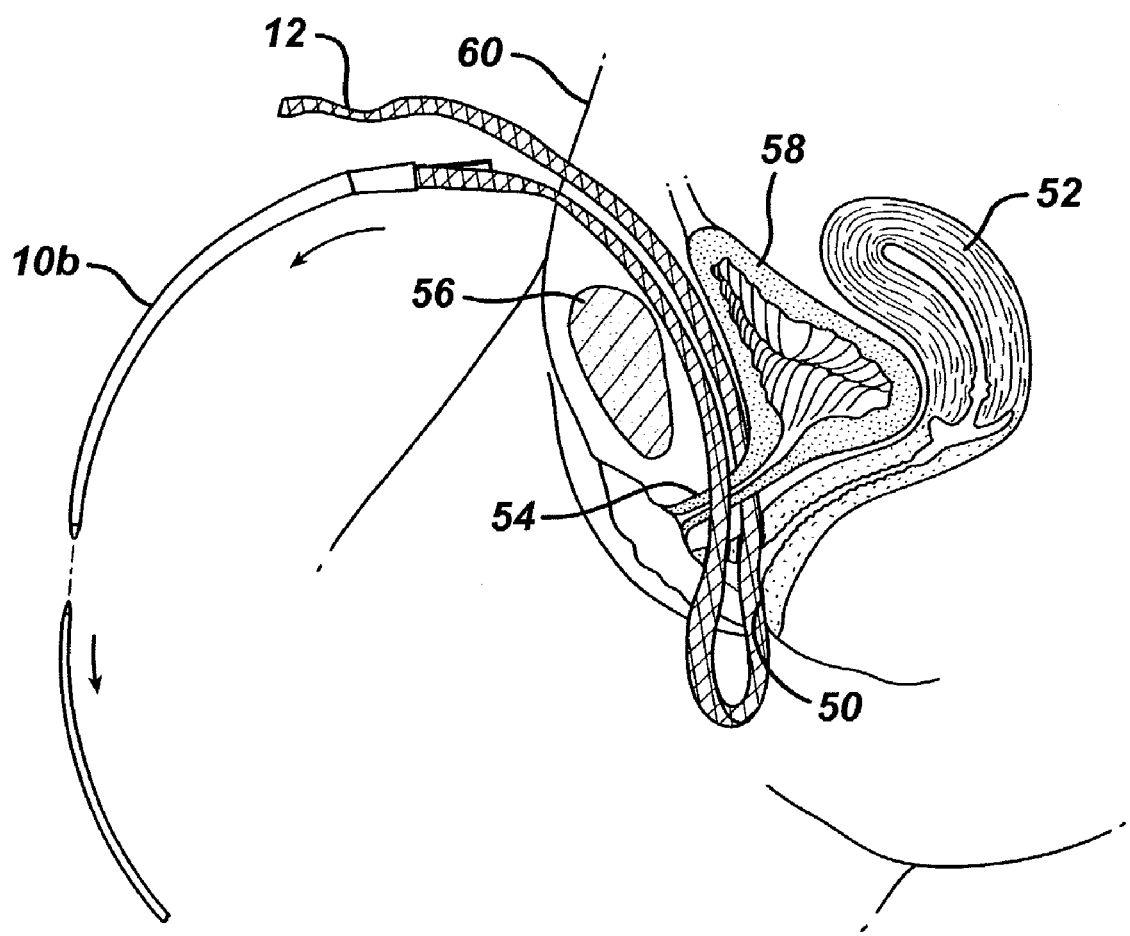
Figure 4J:
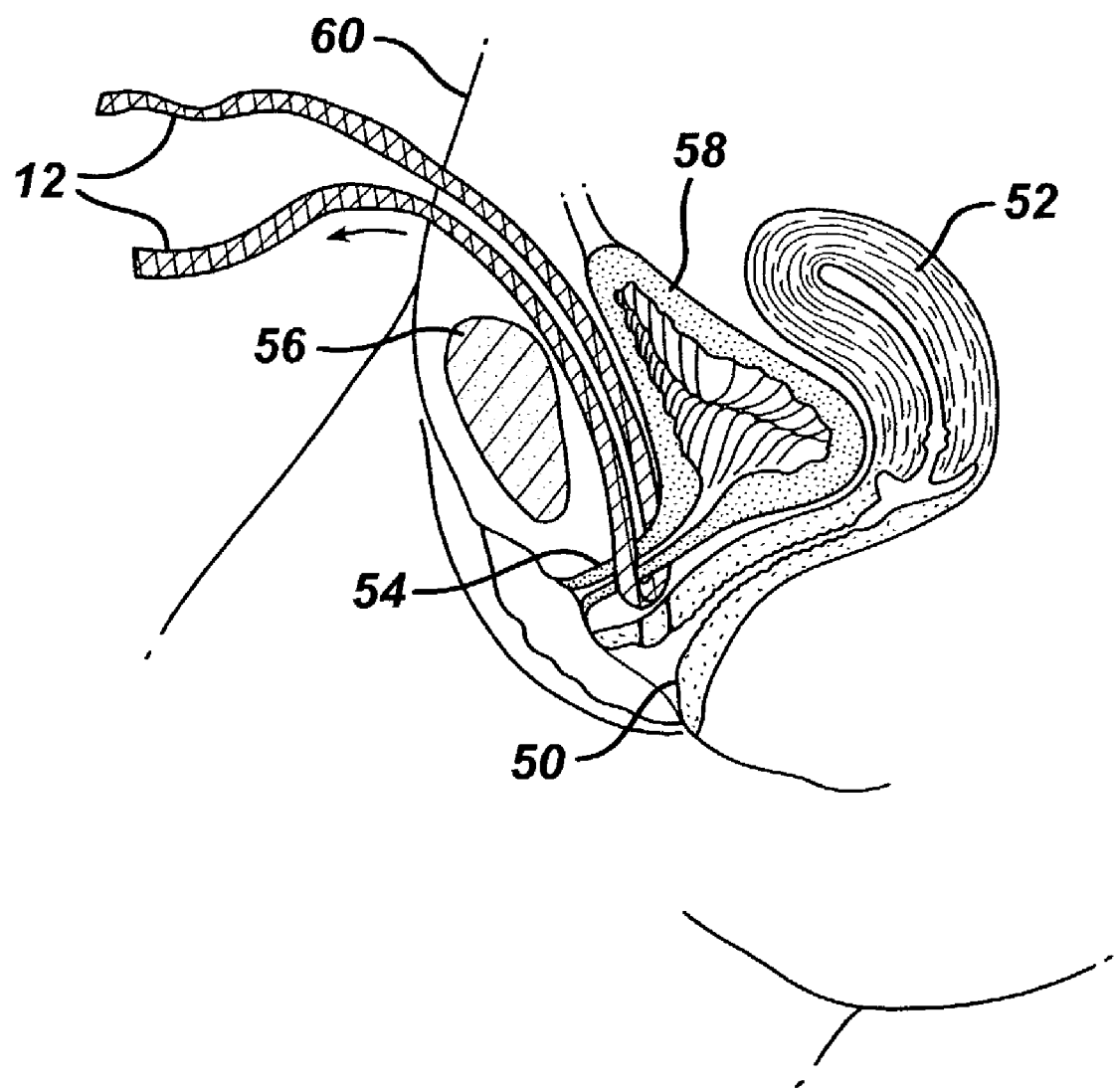

FIGS. 3b–d illustrate alternate connector means utilizing a high friction tube 170, such as Tyron. FIG. 3b discloses a tube having a constant O.D., but a varying I.D. The larger I.D. would accept needle 10 and the smaller I.D. accepts the guide needle 110. FIG. 3c illustrates a tube 172 having both a varying O.D. and I.D. As the needles are placed within the tube the decreasing I.D. compresses around the distal ends of the respective needles and the high coefficient of friction securely anchors the needles. FIG. 3d illustrates the needles within the tube 172. Preferably, the ends of tube 170 and 172 are tapered to eliminate any abrupt surface that adds additional drag to the needles as they are pulled through the abdominal cavity.

The surgical procedure for trans-abdominally implanting mesh 12 using two needles is shown in FIGS. 4a–j. In the figures the relevant parts of the female lower abdomen are disclosed, the vagina being 50, the uterus 52, the urethra 54, the pubic bone 56, the urinary bladder 58 and the abdominal wall 60. A guide needle 110 penetrates the abdominal wall 60, anterior to the pubic bone 56, FIG. 4a and follows the contour of the pubic bone 56 to one side of the urethra 54 and exits the body through an incision having been made in the anterior wall of the vagina 50. Coupler 112 attaches to the distal end of guide needle 110, extending out from the body, and needle 10a, FIG. 4b. One end of mesh 12 is attached to the proximal end of needle 10a. The surgeon then retracts guide needle 110 back through the abdomen and advances needle 10a through the vaginal incision following the same path guide needle 110 created, FIG. 4c. The needles pass through the vaginal wall and through the soft tissue on one side of the urethra 54, the needles then according to FIG. 4d being passed close to the back of the pubic bone 56, through additional layers of fat, muscle and fascia, and then out the abdominal wall 60 above the pubic bone 56. The surgeon uncouples handle 21 from the needle 10a and pulls needle 10a out of the body through the abdominal wall 60, FIG. 4e.

Guide needle 110 is disconnected from needle 10a, and the surgeon repeats the same procedure, but passing the guide needle 110 on the opposite side of the urethra 54, FIGS. 4f–j, to complete the implantation of the mesh between the mid-urethra and vaginal wall using needle 10b.

FIGS. 8a–i illustrate an alternate preferred embodiment. A first guide needle 110a penetrates the abdominal wall 60, anterior to the pubic bone 56 and follows the contour of the pubic bone 56 to one side of the urethra 54 and exits the body through an incision having been made in the anterior wall of the vagina 50. A second guide needle 110b penetrates the abdominal wall 60, anterior to the pubic bone 56 and follows the contour of the pubic bone 56 to the opposite side of the urethra 54 as guide needle 110a and exits the body through an incision having been made in the anterior wall of the vagina 50, FIG. 8a. At this point, the surgeon may perform a single cystoscopy to confirm the integrity of the bladder 58. Couplers 12a,b attach to the distal ends of needles 10a,b. Needle 10a, having one end of mesh 12 attached to the proximal end of needle 10a attaches to guide needle 110a via coupler 112a, FIG. 8b. The surgeon then retracts guide needle 110a back through the abdomen and advances needle 10a through the vaginal incision following the same path guide needle 110a created. The needles pass through the vaginal wall and through the soft tissue on one side of the urethra 54, the needles being passed close to the back of the pubic bone 56, through additional layers of fat, muscle and fascia, and then out the abdominal wall 60 above the pubic bone 56, FIGS. 8c–d. The surgeon uncouples handle 21 from the needle 10a and pulls needle 10a out of the body through the abdominal wall 60, FIG. 8e.

The surgeon repeats the same procedure, but removing guide needle 110b and advancing needle 10b on the opposite side of the urethra 54, to complete the implantation of the mesh between the mid-urethra and vaginal wall using needle 10b, FIGS. 8f–i.

Figure 5A:
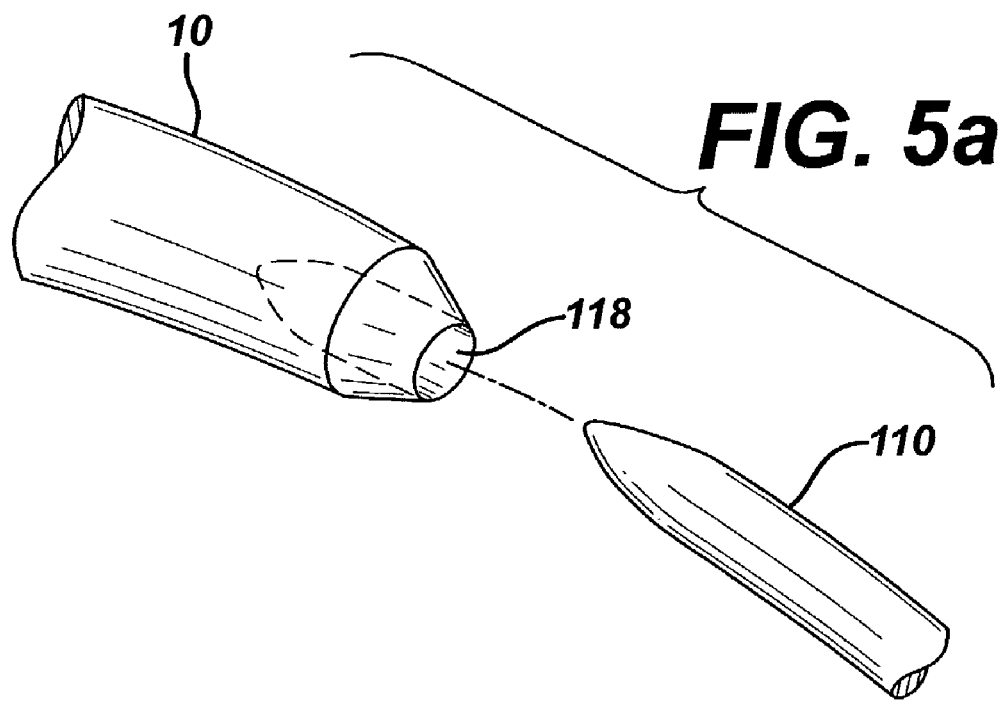
FIGS. 5a–d illustrate alternate embodiments of coupling the guide needle to the needle.
Figure 5B:
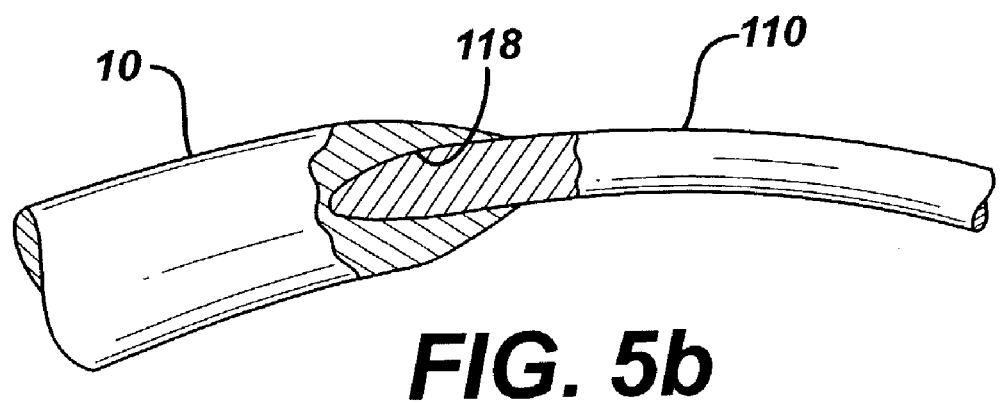

FIGS. 5a–d illustrate alternate embodiments for coupling needle 10 to guide needle 110 to implant a mesh 12 trans-abdominally as indicated above. In FIGS. 5a–b, the distal end of needle 10 is modified to include a bore opening 118 to allow for a press fit connection with the distal end of guide needle 110. Alternatively, bore-opening 118 may comprise other connection means, such as glue or a high-friction material.

Figure 5C:
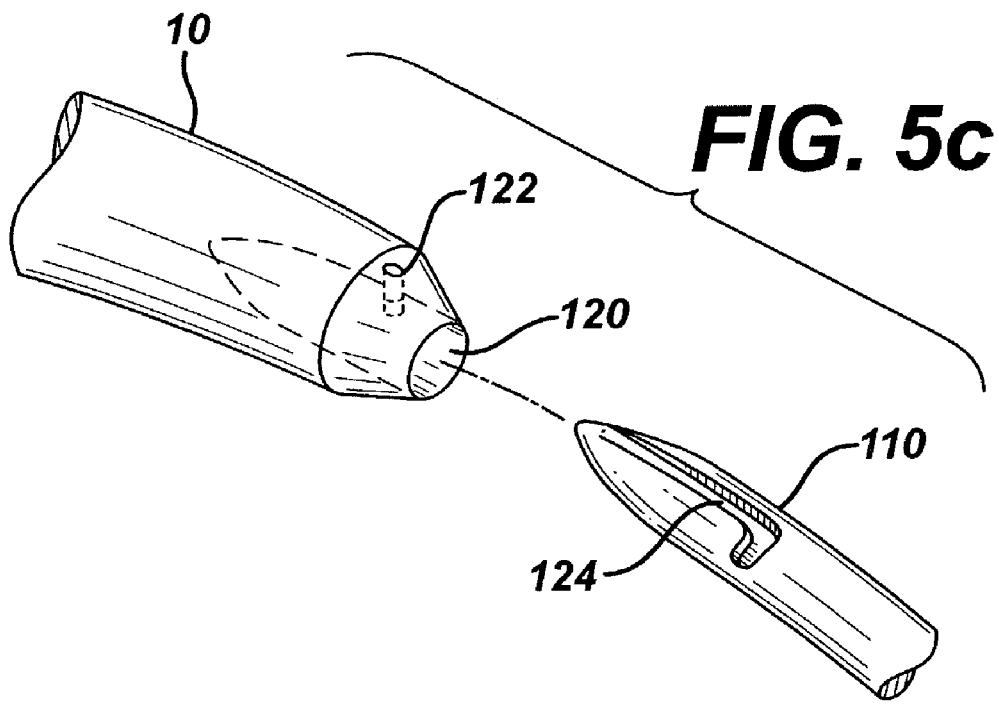
Figure 5D:
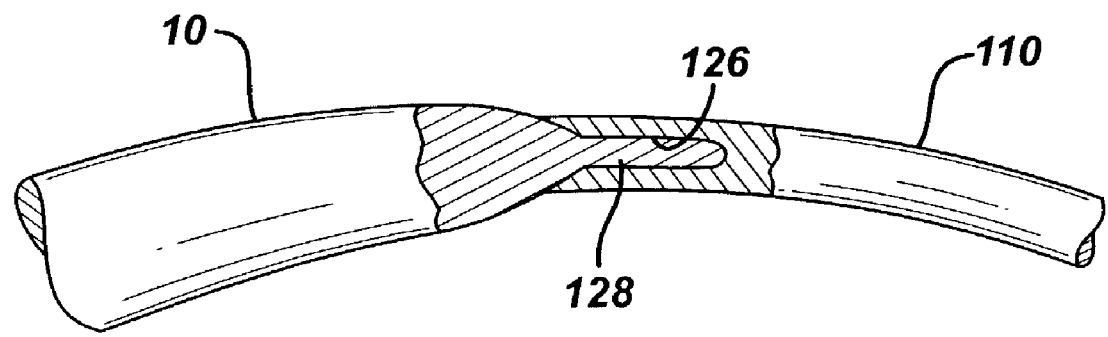

In FIG. 5c, the distal end of needle 10 is modified to include a bore opening 120 and a locking pin 122. Guide needle 110 is modified to include an L-shaped groove 124. The distal end of guide needle 110 inserts into opening 120 and groove 124 engages locking pin 122 and locks thereto with a quarter-turn twist. FIG. 5d illustrates a bore opening 126 in guide needle 110 to accept a protruding element 128 at the distal end needle 10. Protruding element 128 press fits into bore opening 126.

One advantage of the embodiment shown in FIG. 3 is that the needle 10 can be used for either a trans-abdominal approach or a trans-vaginal approach. In this approach, a kit comprising two needles 10, attached to a mesh 12, at least one coupler and at least one guide needle may be distributed for use by multiple surgeon specialists. For example, a gynecologist may prefer the trans-vaginal approach and will simply discard the connector and guide needle from the kit. On the other hand, a urologist may prefer the trans-abdominal approach and utilize the connector(s) and guide needle(s).

Referring now to FIGS. 6a–h, an alternate embodiment of the invention utilizes the needle 10 to penetrate the abdominal wall 60 and couple to the mesh 12. In this embodiment, the mesh 12 is modified to create a connection means for connecting to the distal end of the needle 10. The connection means is preferably detachable so that when the mesh is pulled out of the abdominal wall, the mesh may be detached from the needle and the needle reused to retrieve the other end of the mesh. This embodiment allows for the use of a single needle for the procedure. This embodiment also allows for the use of a mesh constructed, at least in part, of natural materials, which are otherwise not suitable in the pre-affixed embodiment due to the inability of the natural material to survive extended periods in inventory.

Figure 6A:
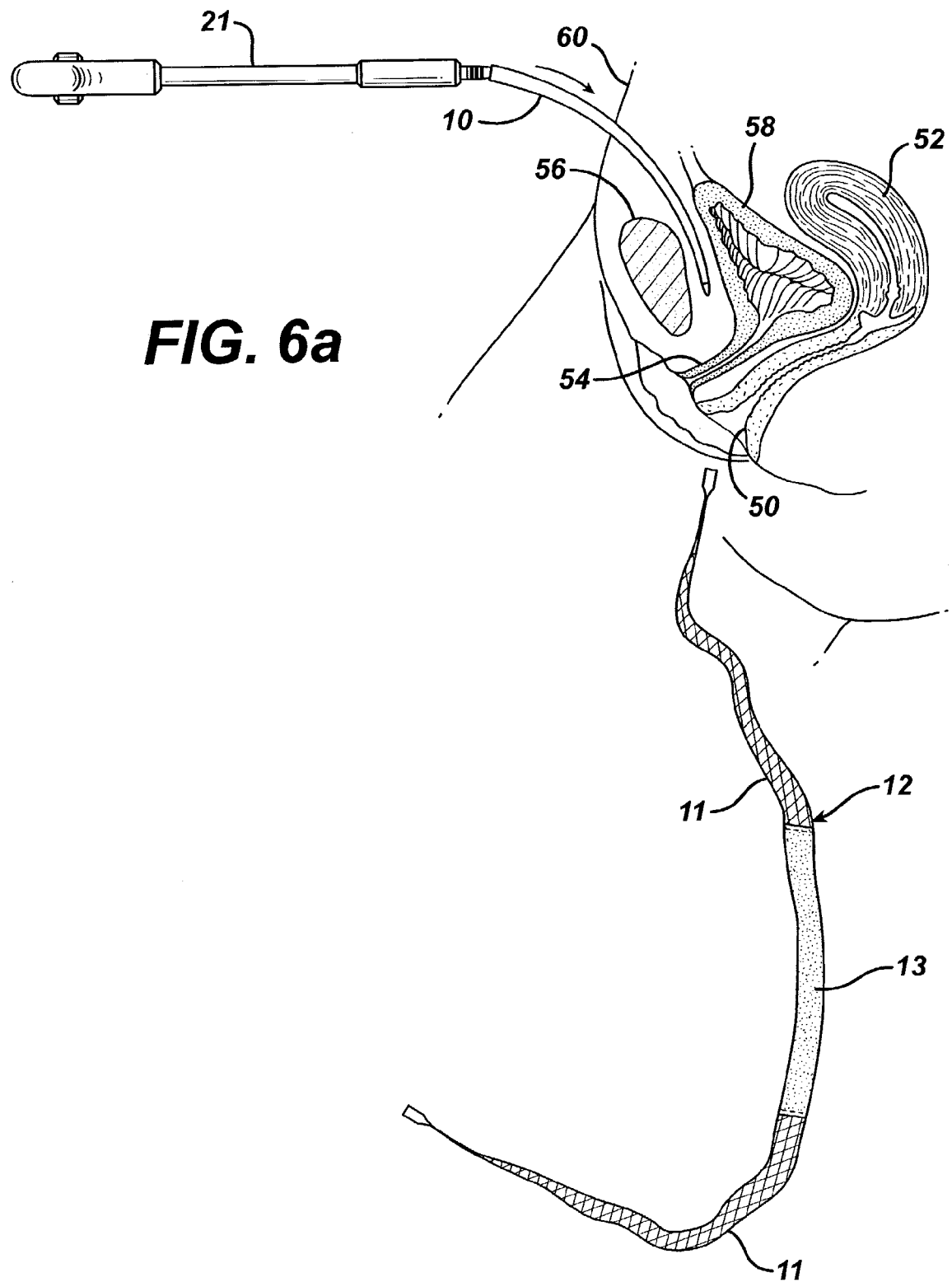
FIGS. 6a–h diagrammatically illustrate several surgical steps of a trans-abdominal method utilizing a single needle according to an alternate embodiment of the invention to treat SUI.
Figure 6B:
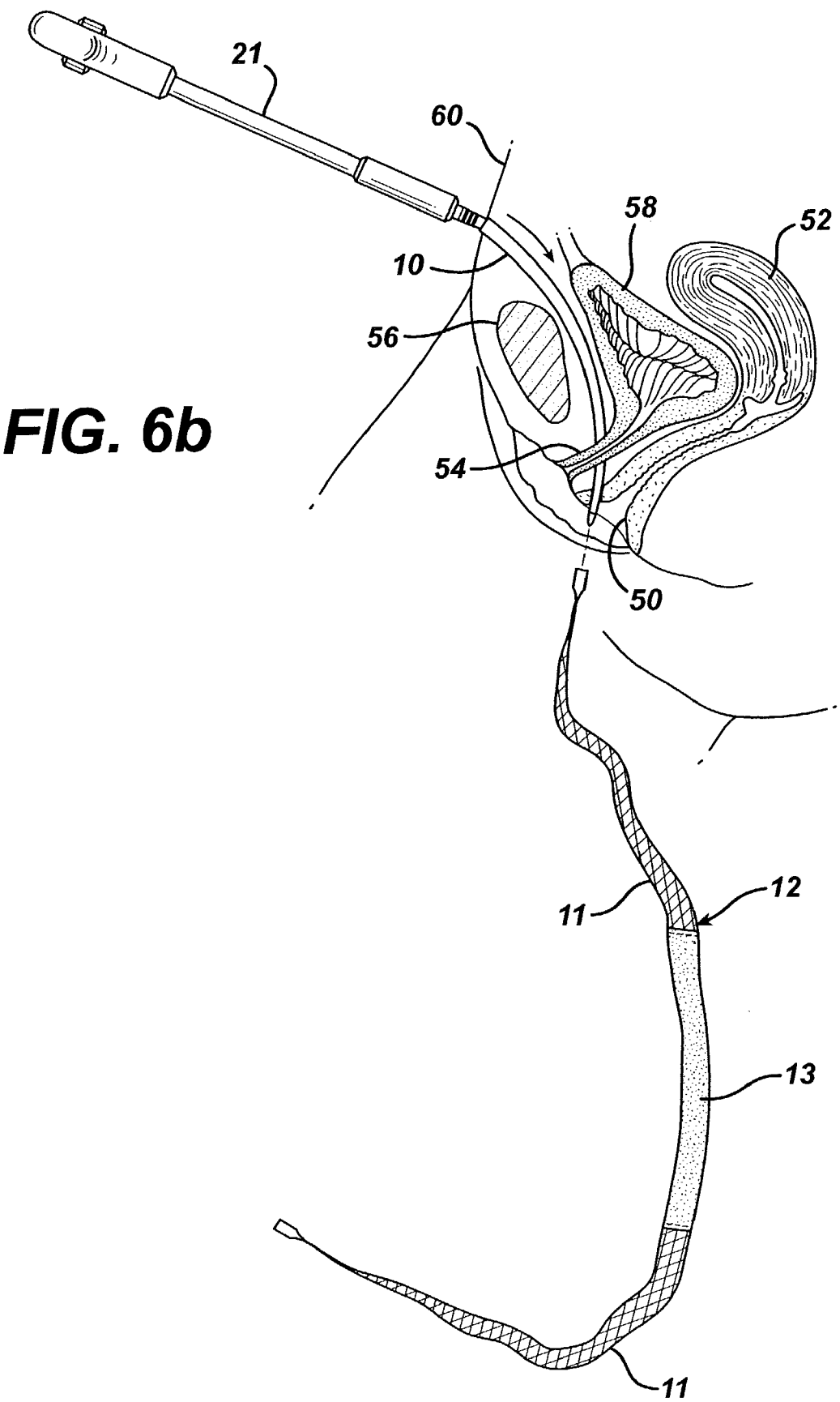
Figure 6C:
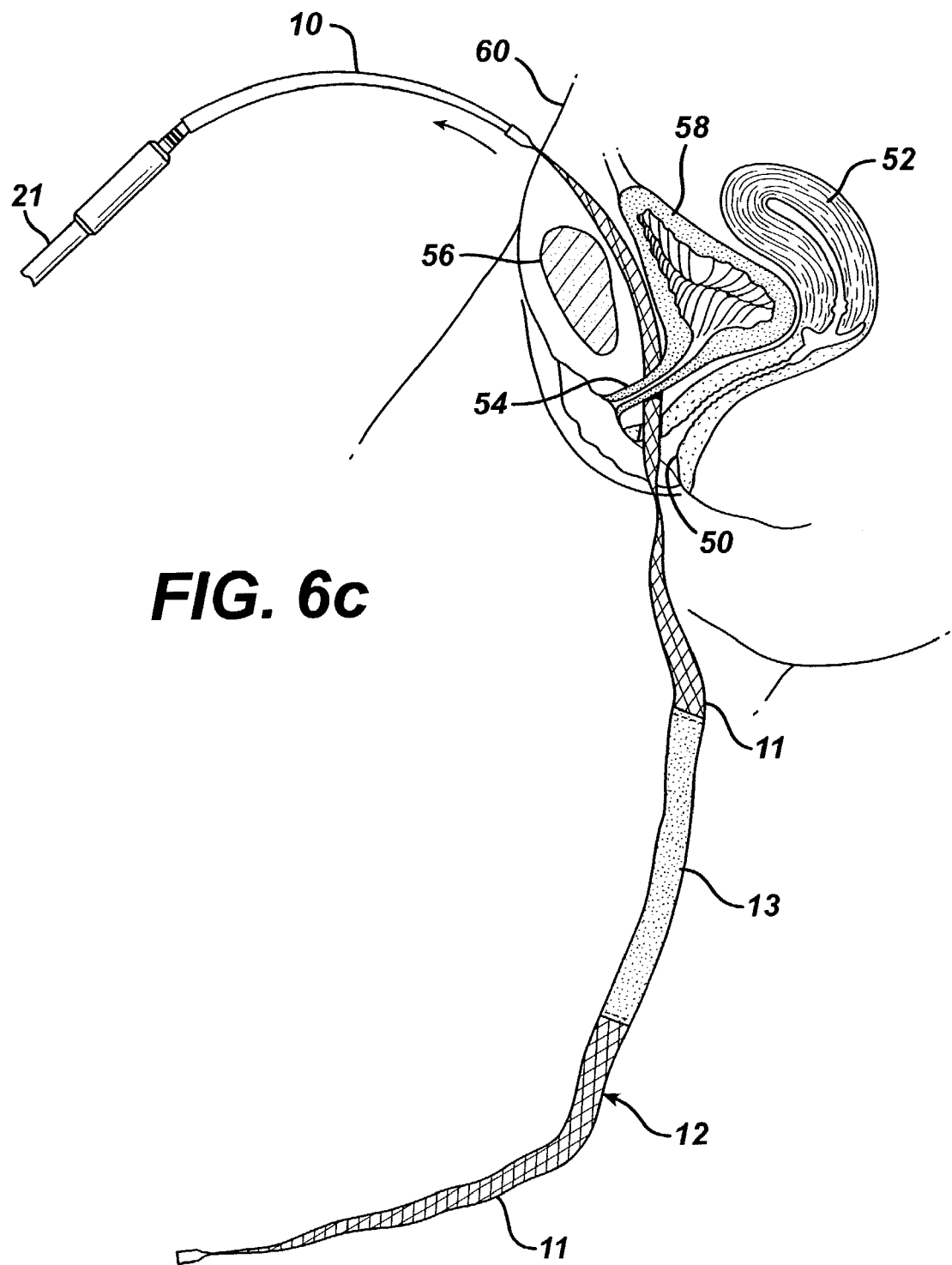
Figure 6D:
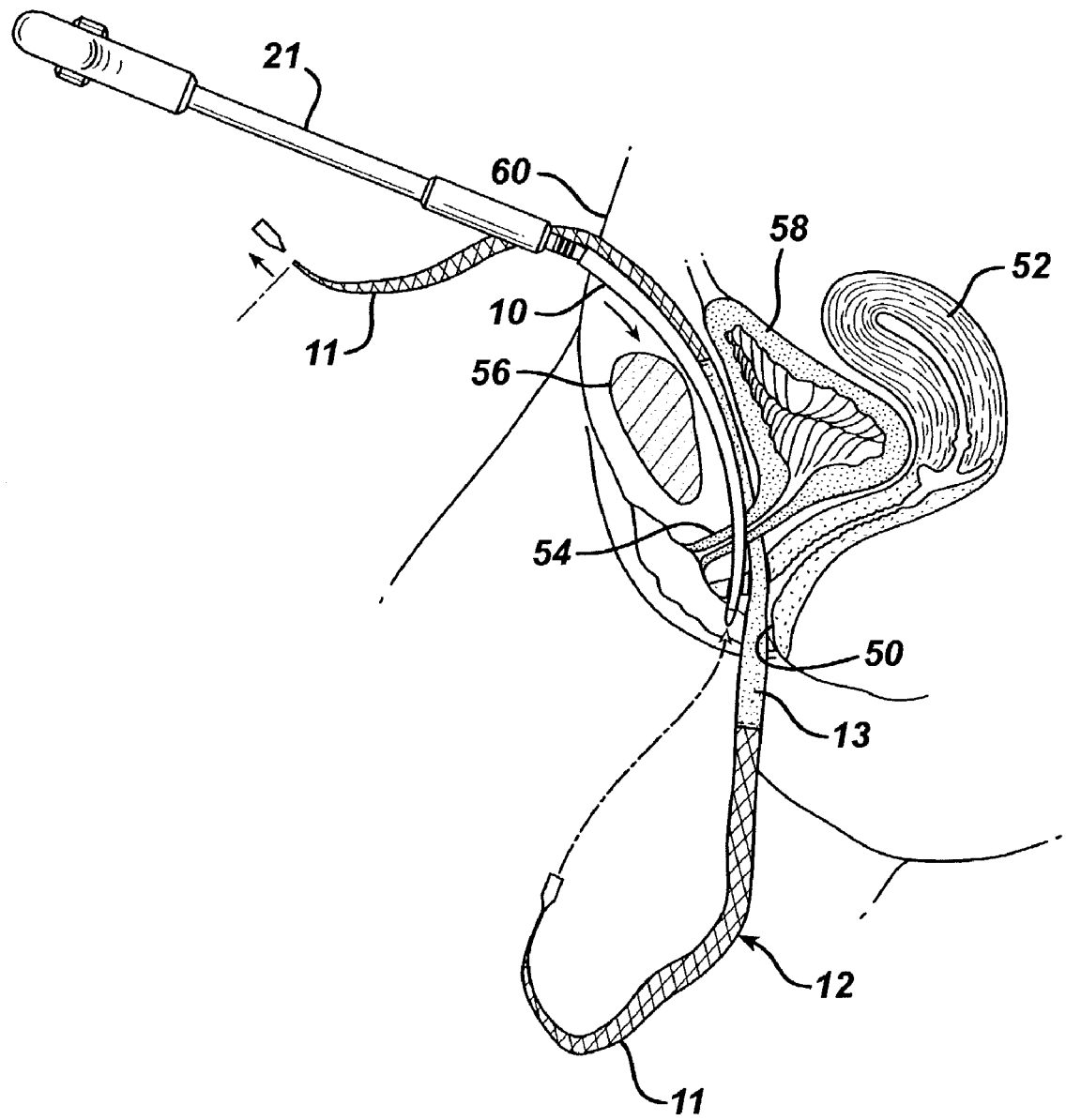
Figure 6E:
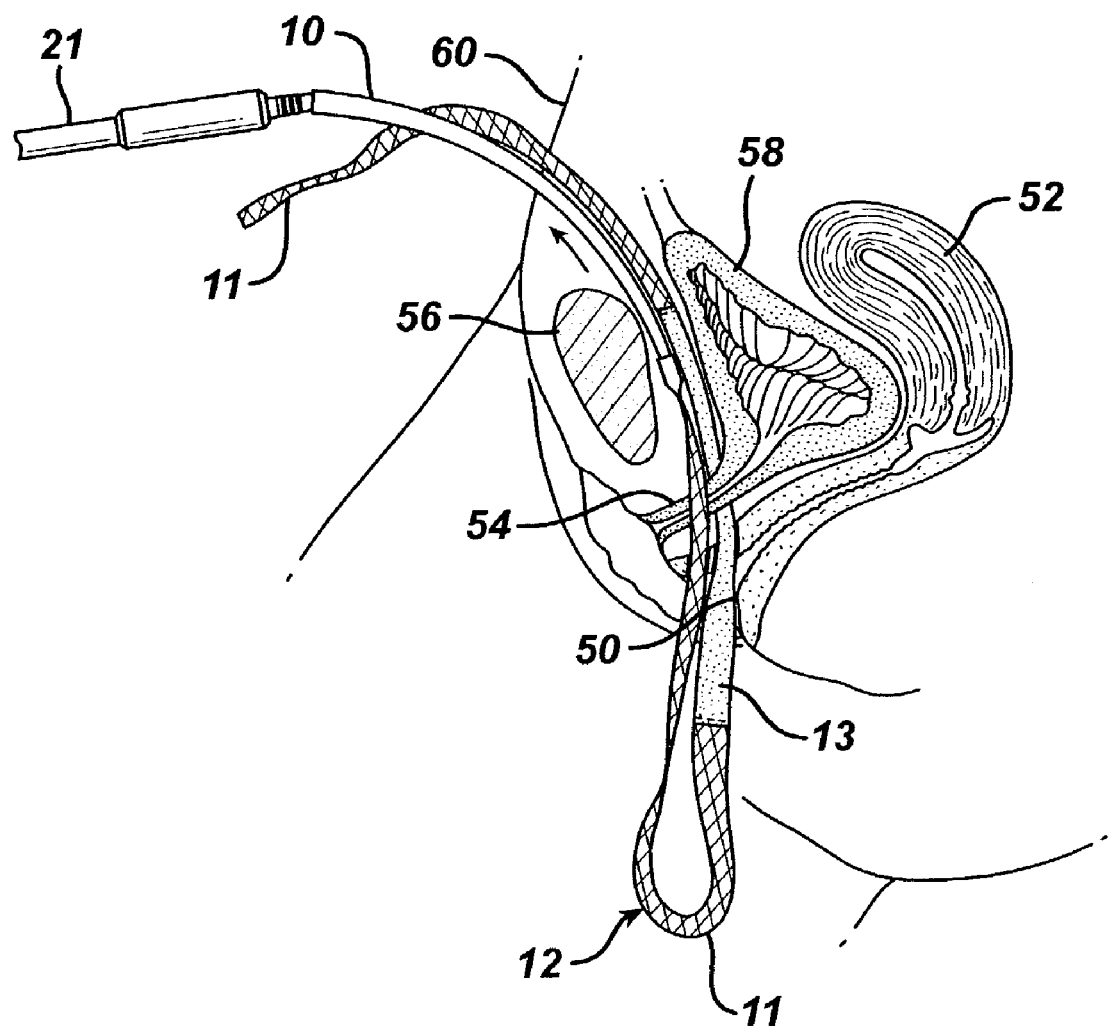
Figure 6F:
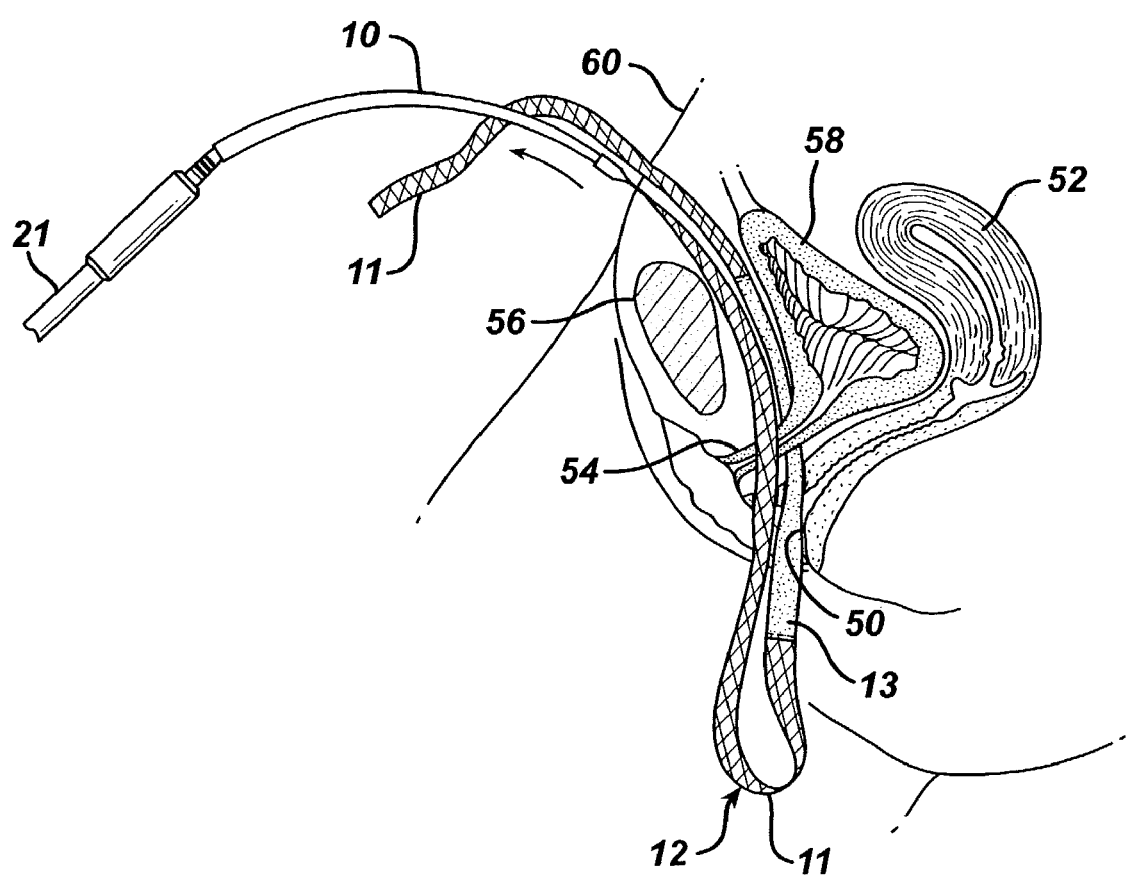
Figure 6G:
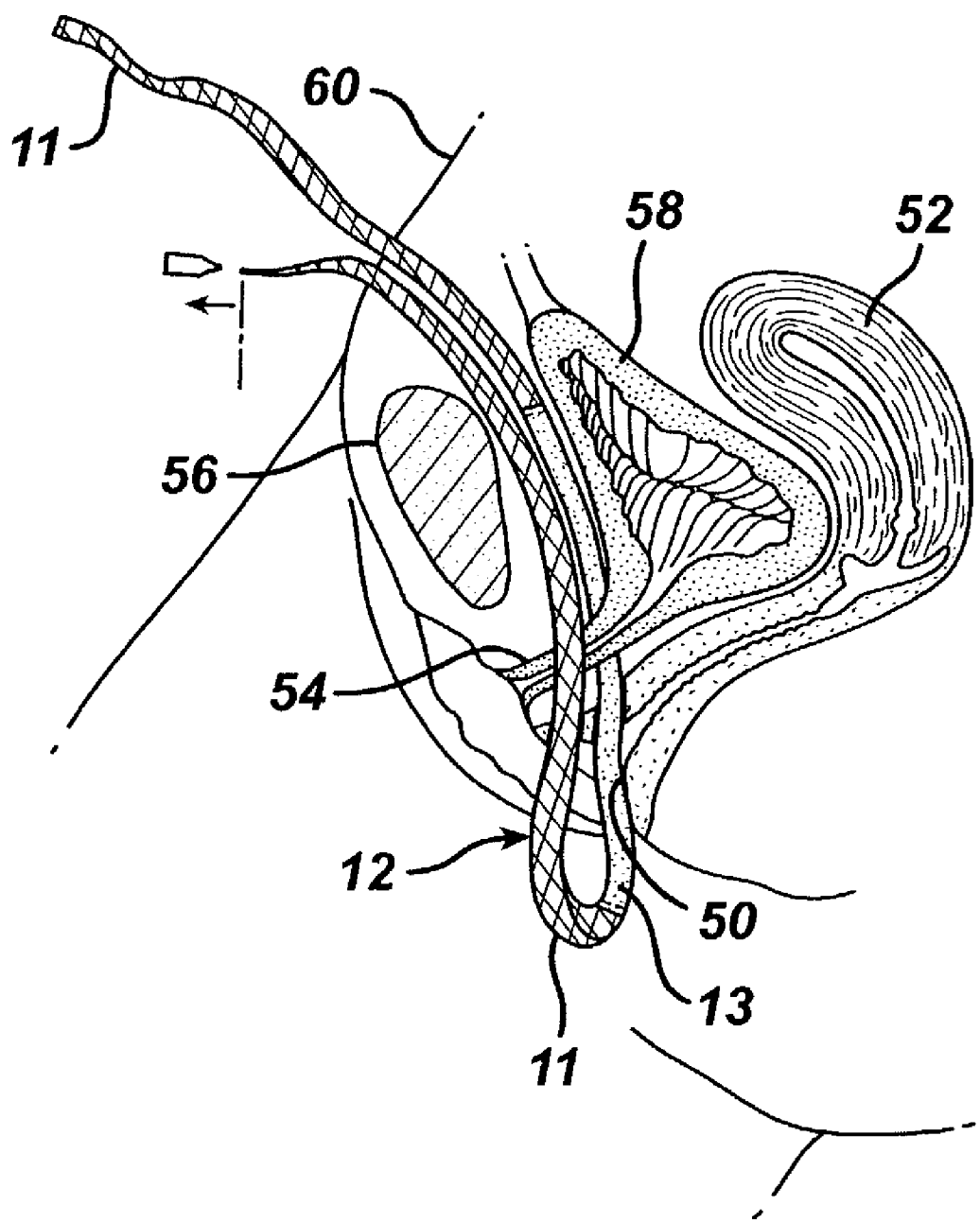
Figure 6H:
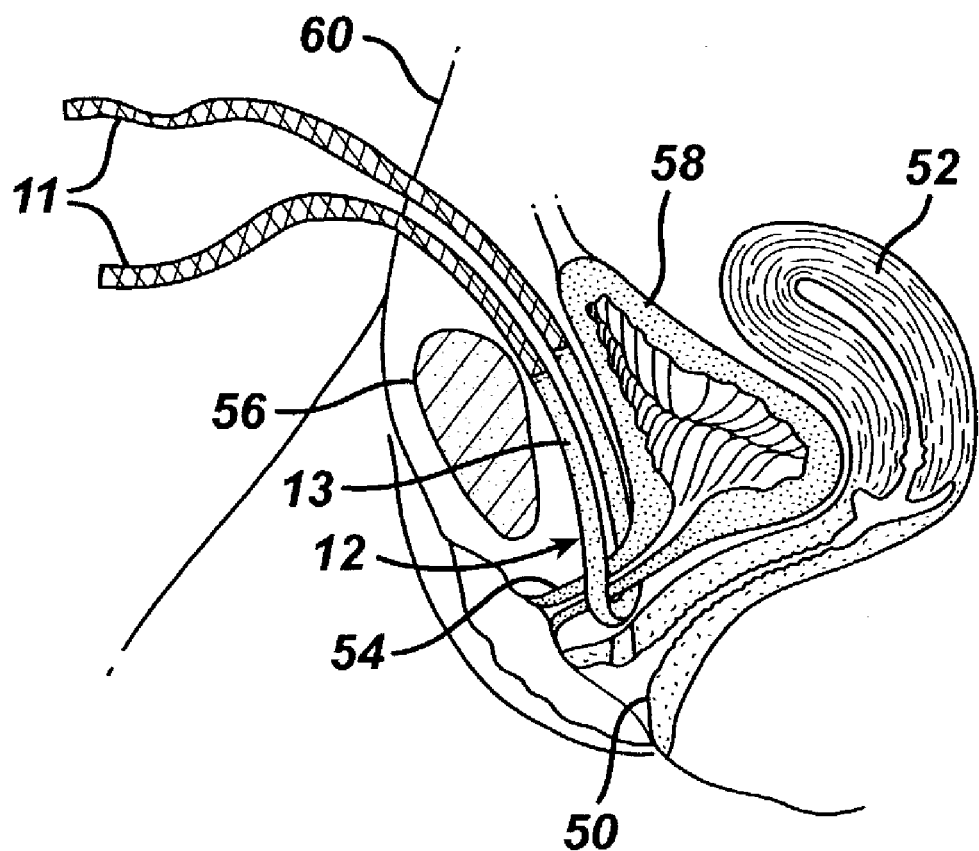

A needle 10 with coupling means at the distal end penetrates the abdominal wall 60, anterior to the pubic bone 56, FIG. 6a and follows the contour of the pubic bone 56 to one side of the urethra 54 and exits the body through an incision having been made in the anterior wall of the vagina 50, FIG. 6b. A first end of mesh 12 attaches to the distal end of needle 10 via coupling means. The surgeon then retracts needle 10 back through the pelvic cavity, following the same path created by needle 10, while at the same time causing mesh 12 to follow the needle, FIG. 4c. The needle 10 and mesh 12 pass through the vaginal wall and through the soft tissue on one side of the urethra 54. The needle and mesh then according to FIG. 4f being passed close to the back of the pubic bone 56, through additional layers of fat, muscle and fascia, and then out the abdominal wall 60 above the pubic bone 56.

Needle 10 disconnects from the first mesh end, and the surgeon repeats the same procedure, but this time passes the needle 10 on the opposite side of the urethra 54, FIGS. 6d–h, to complete the implantation of the mesh 12 between the mid urethra and vaginal wall.

Figure 7A:
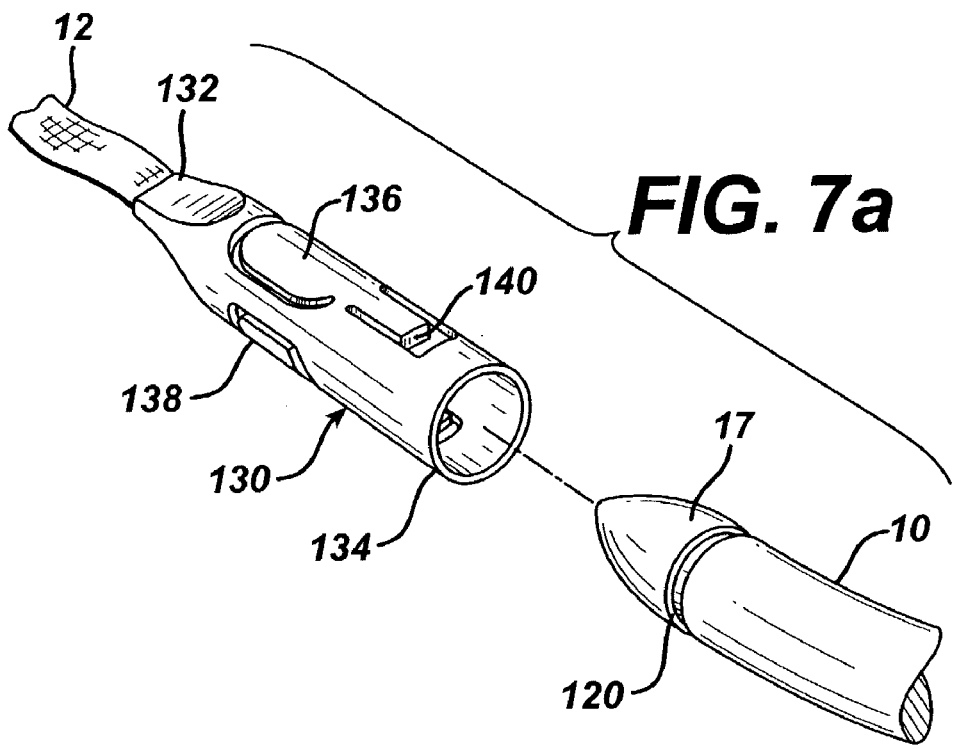
FIGS. 7a–g illustrate alternate embodiments of coupling the needle to the mesh.
Figure 7B:
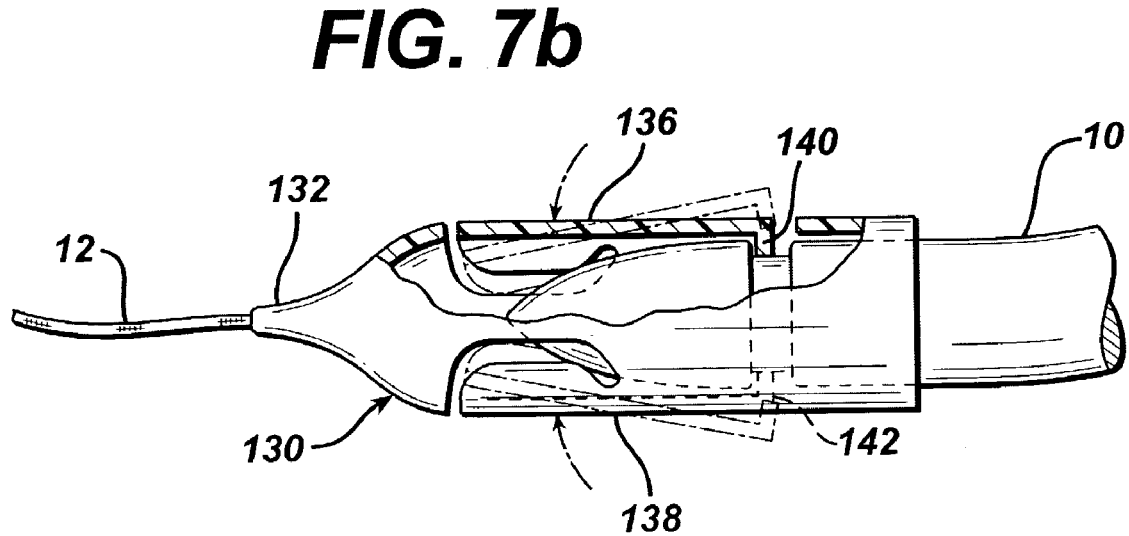

Referring to FIGS. 7a–g, alternate embodiments for connecting the needle 10 to the mesh 12 are disclosed. FIGS. 7a–b disclose a coupler 130 having a proximal end 132 configured to accept the mesh 12 and a distal end 134 for accepting the distal end 17 of needle 10. Distal end 17 comprises a contiguous groove 120 for detachably coupling with coupler 130. Coupler 130 further comprises two spring tabs 136 and 138, each with fingers 140 and 142 for engaging groove 120. Mesh 12 is preferably attached to the distal end 132 using a biocompatible glue or other appropriate mechanical fastening means. The surgeon may simply attach or detach needle 10 from coupler 130 by depressing spring tabs 136 and 138 forcing fingers 140 and 142 upward to allow distal end 17 to slide in or out of coupler 130. Fingers 140 and 142 engage groove 120 to hold needle 10 firmly in place within coupler 130.

Figure 7C:
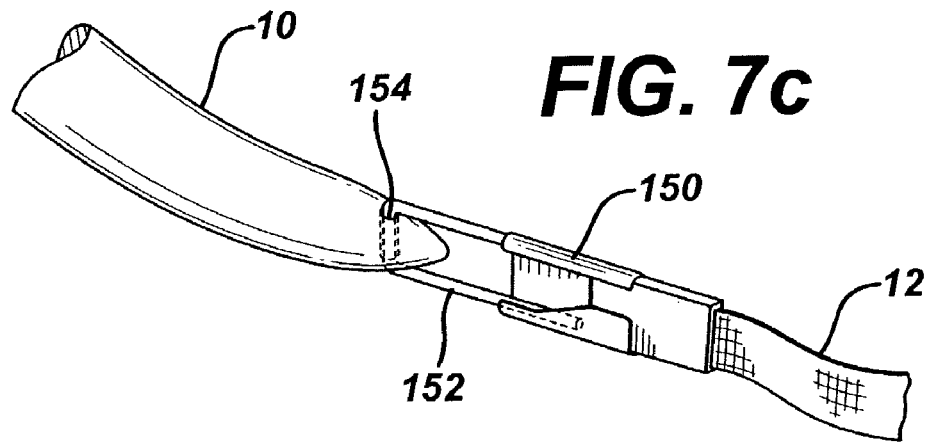
Figure 7D:
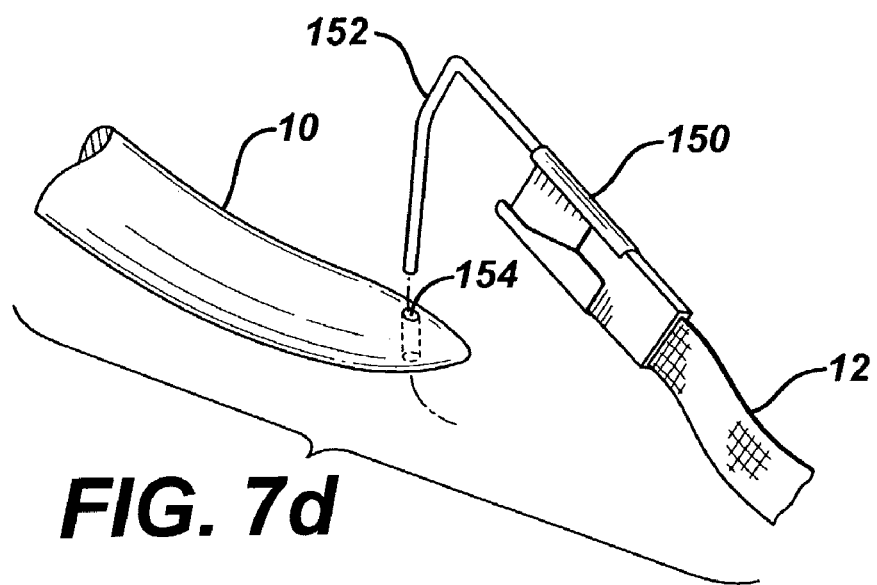
Figure 7E:
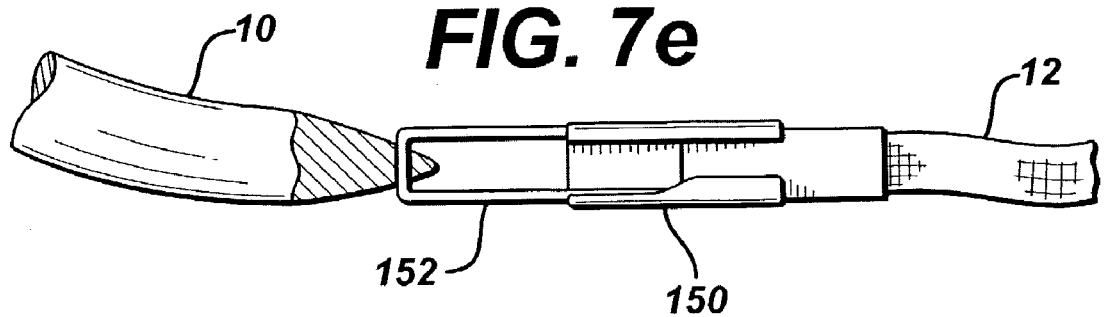

FIGS. 7c–e illustrate a coupling mechanism 150 similar in function to a safety pin. Spring arm 152 engages with a bore 154 at the distal end 17 of needle 10.

Figure 7F:
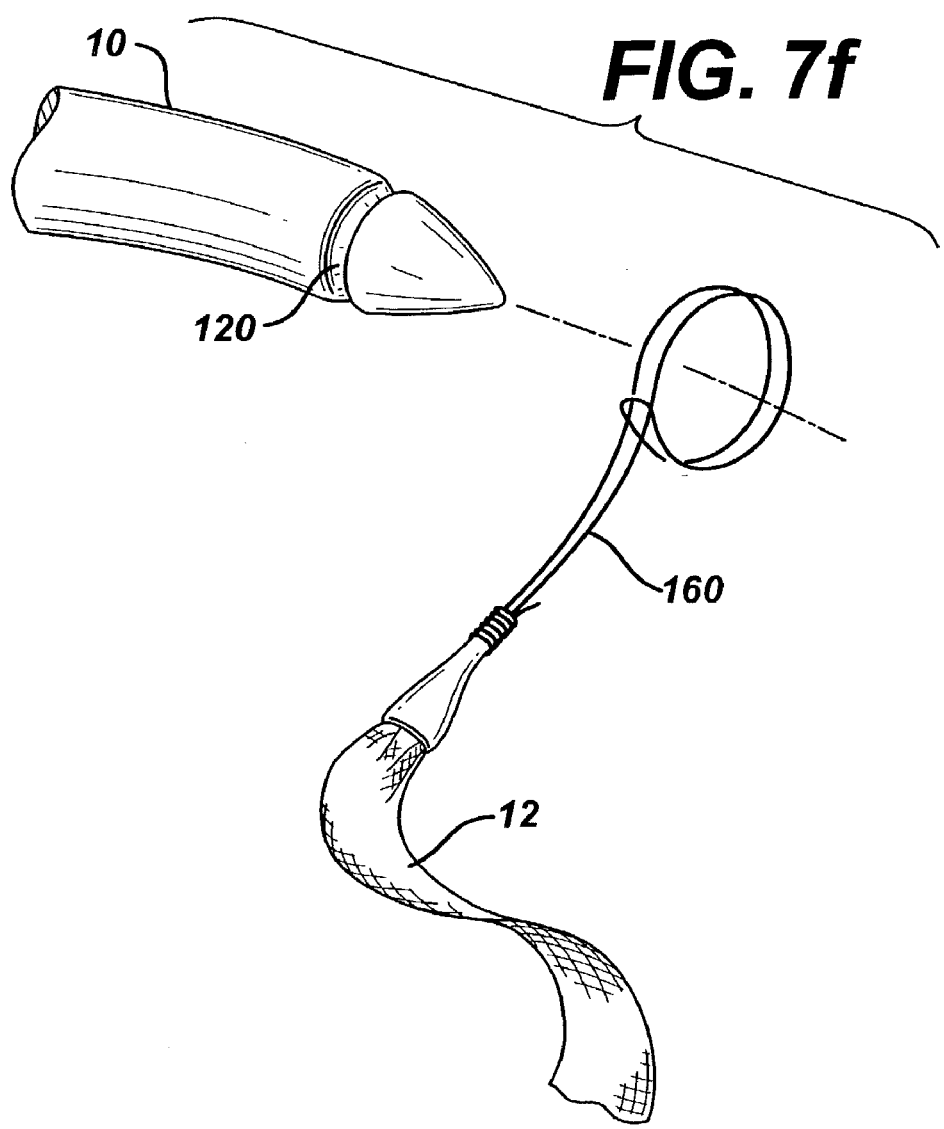
Figure 7G:
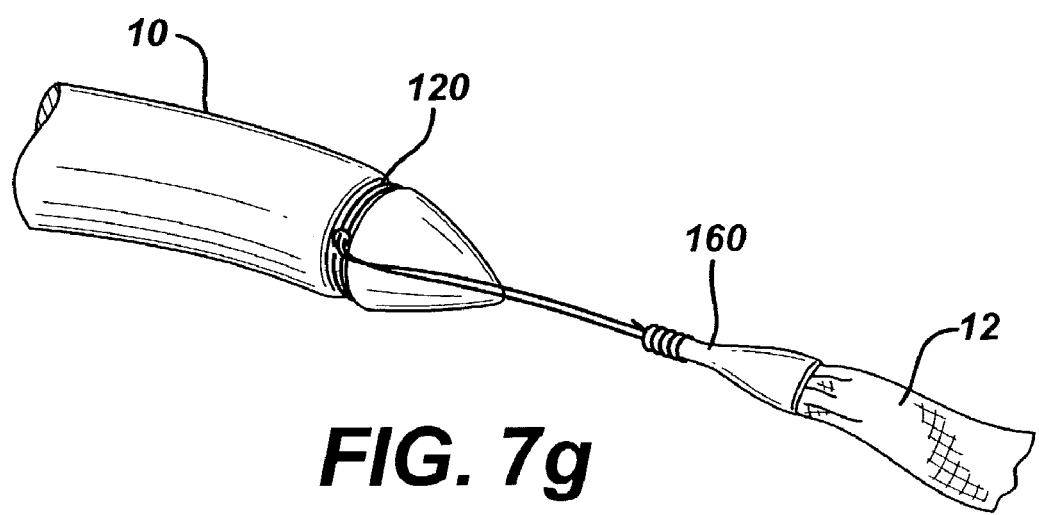
Figure 8A:
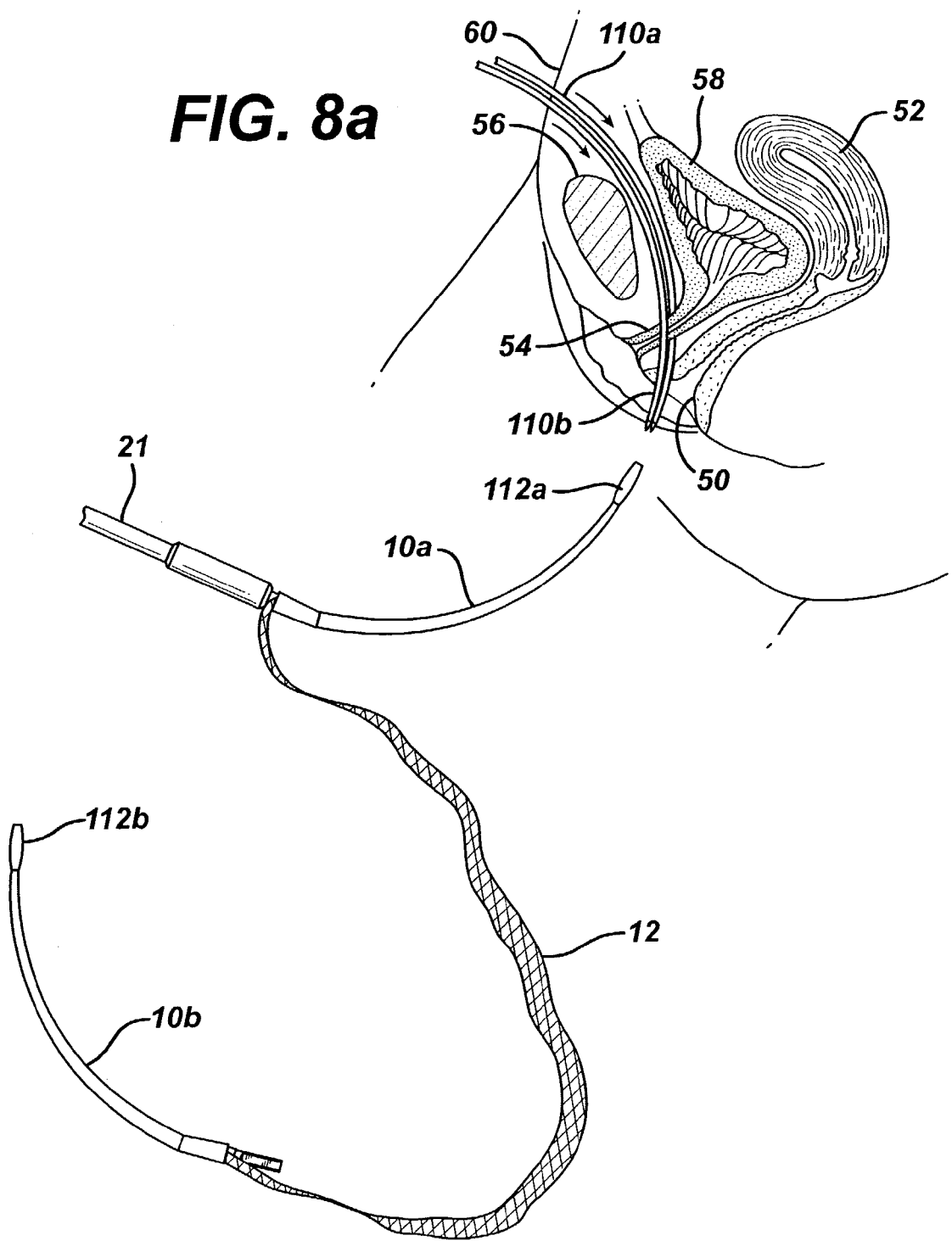
Figure 8B:
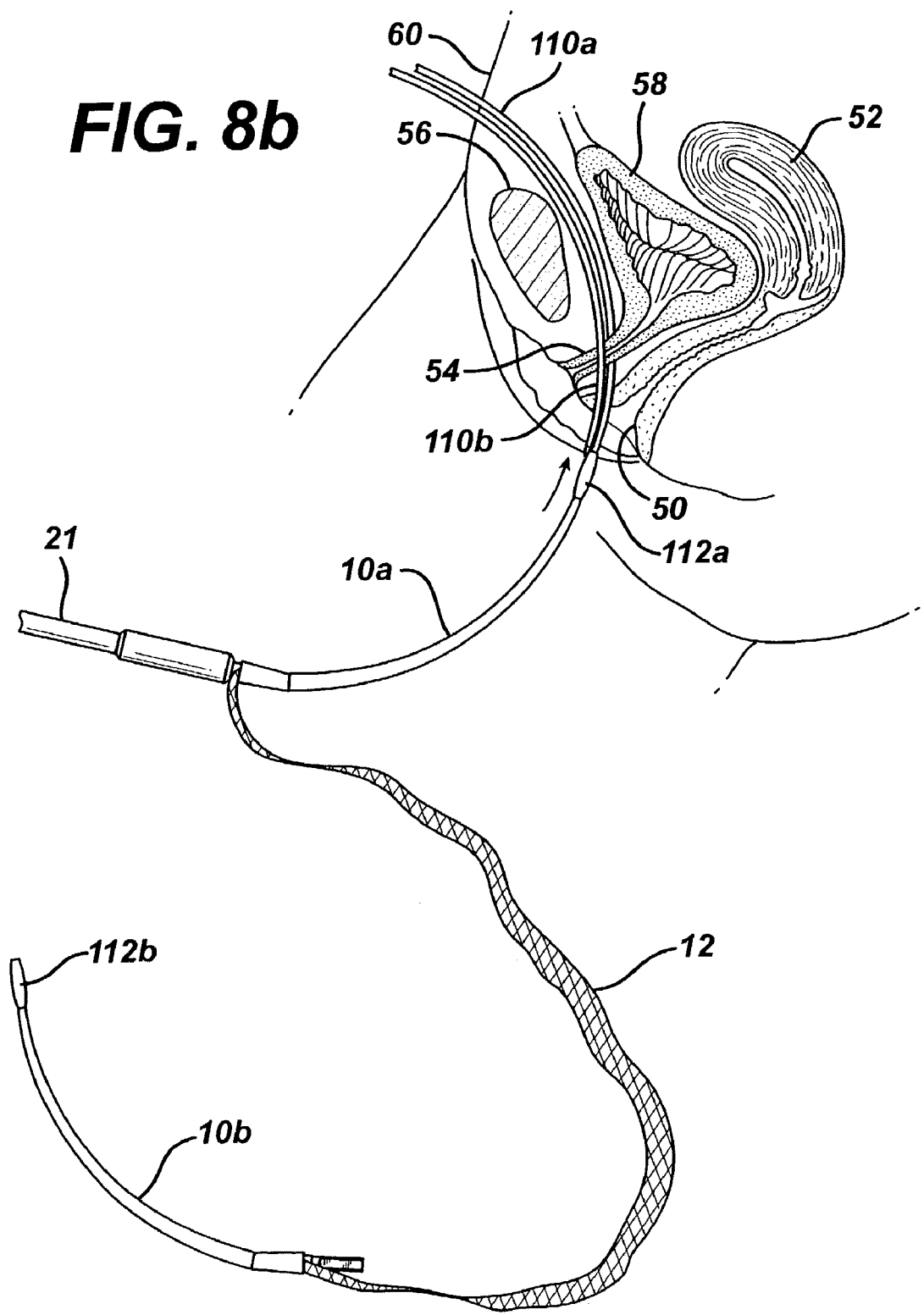
Figure 8C:
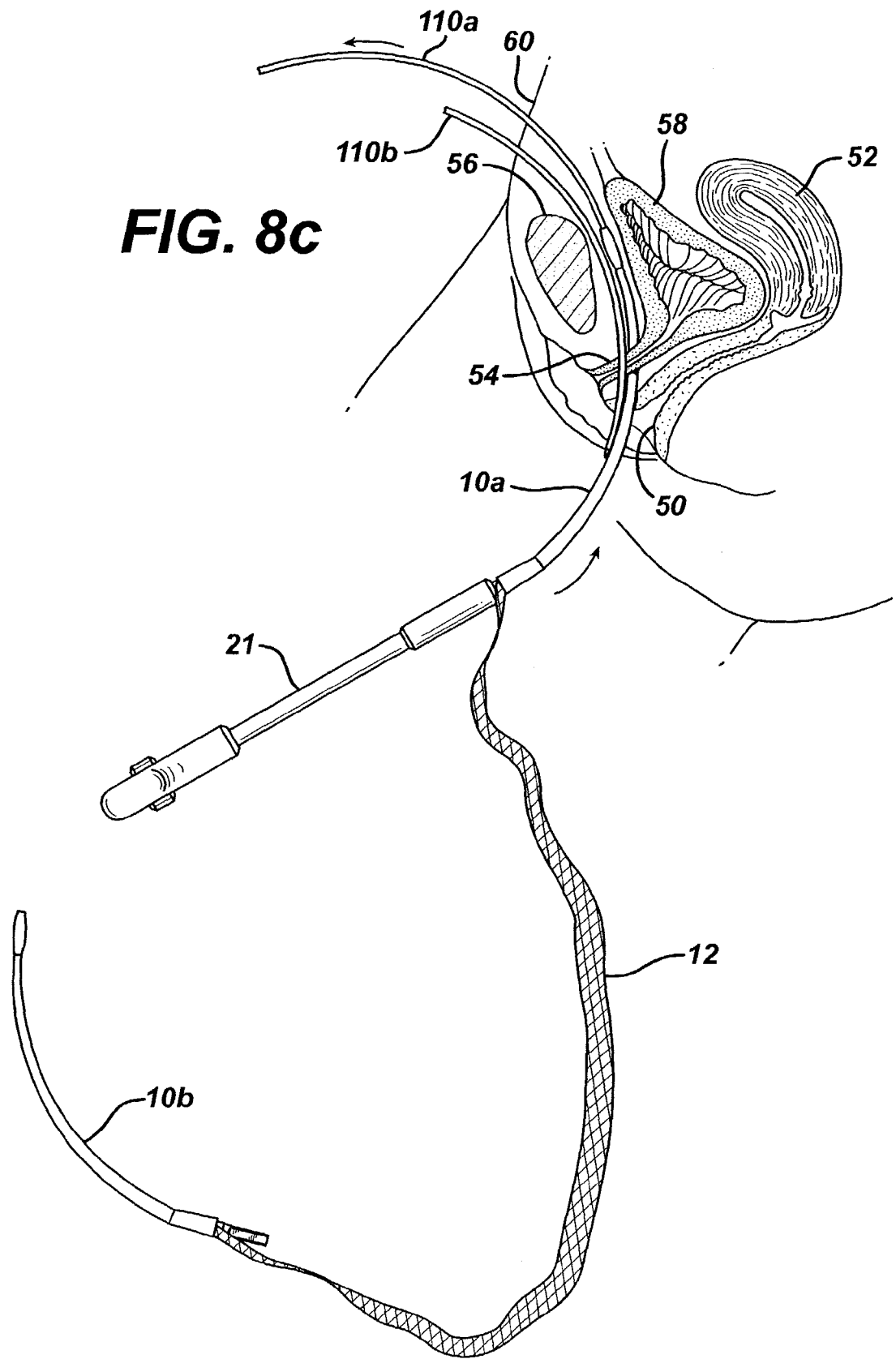
Figure 8D:
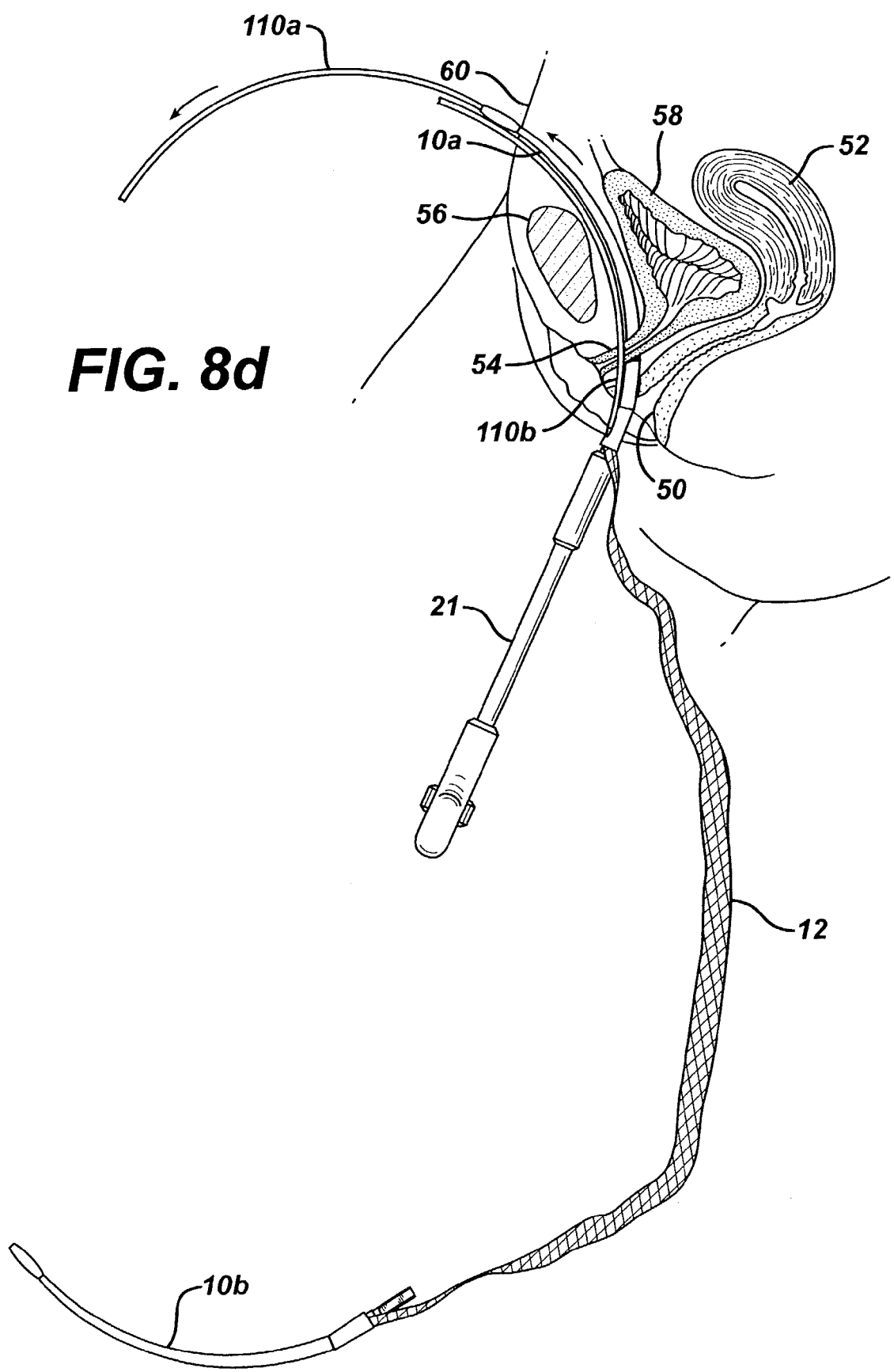
Figure 8E:
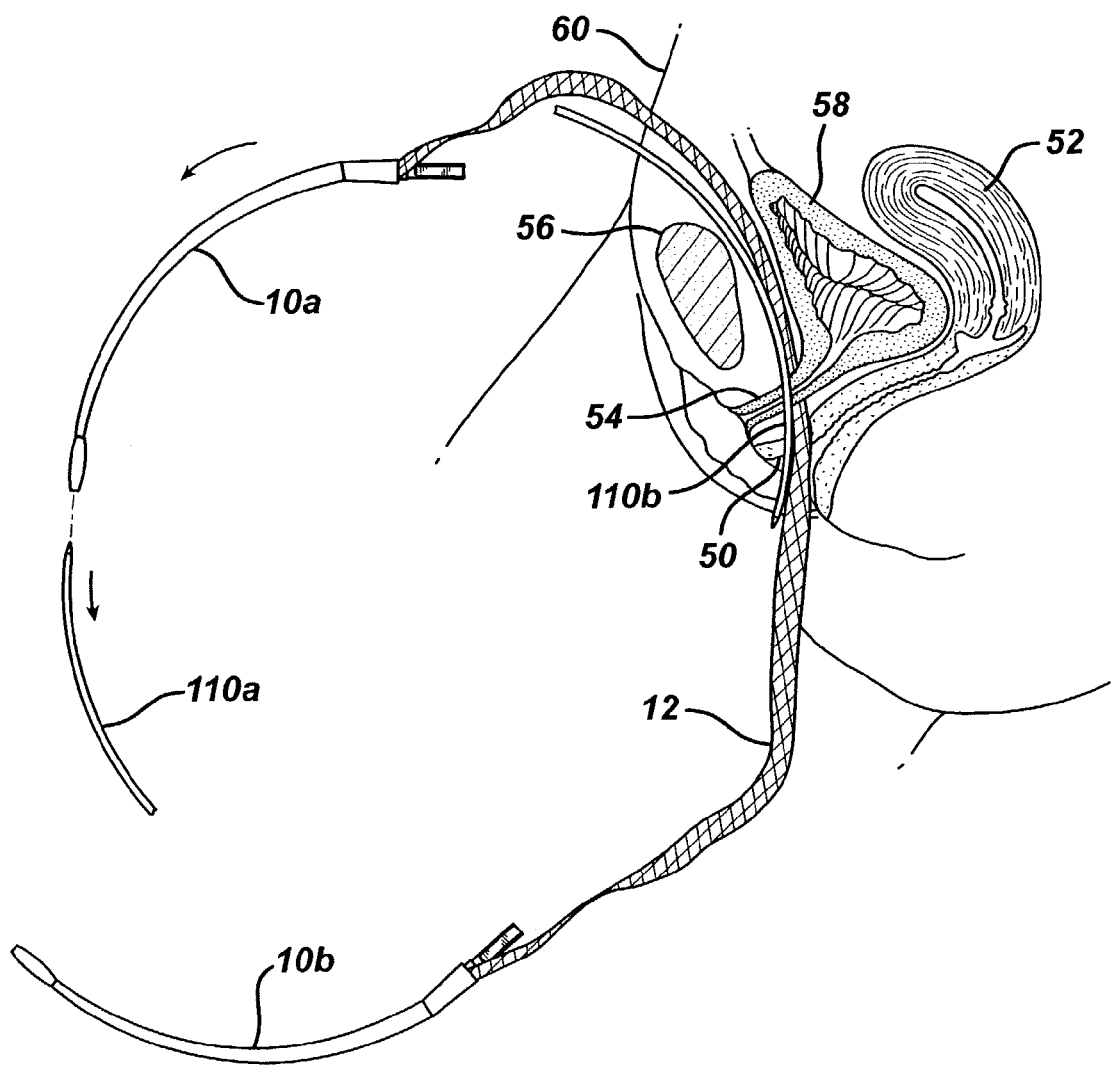
Figure 8G:
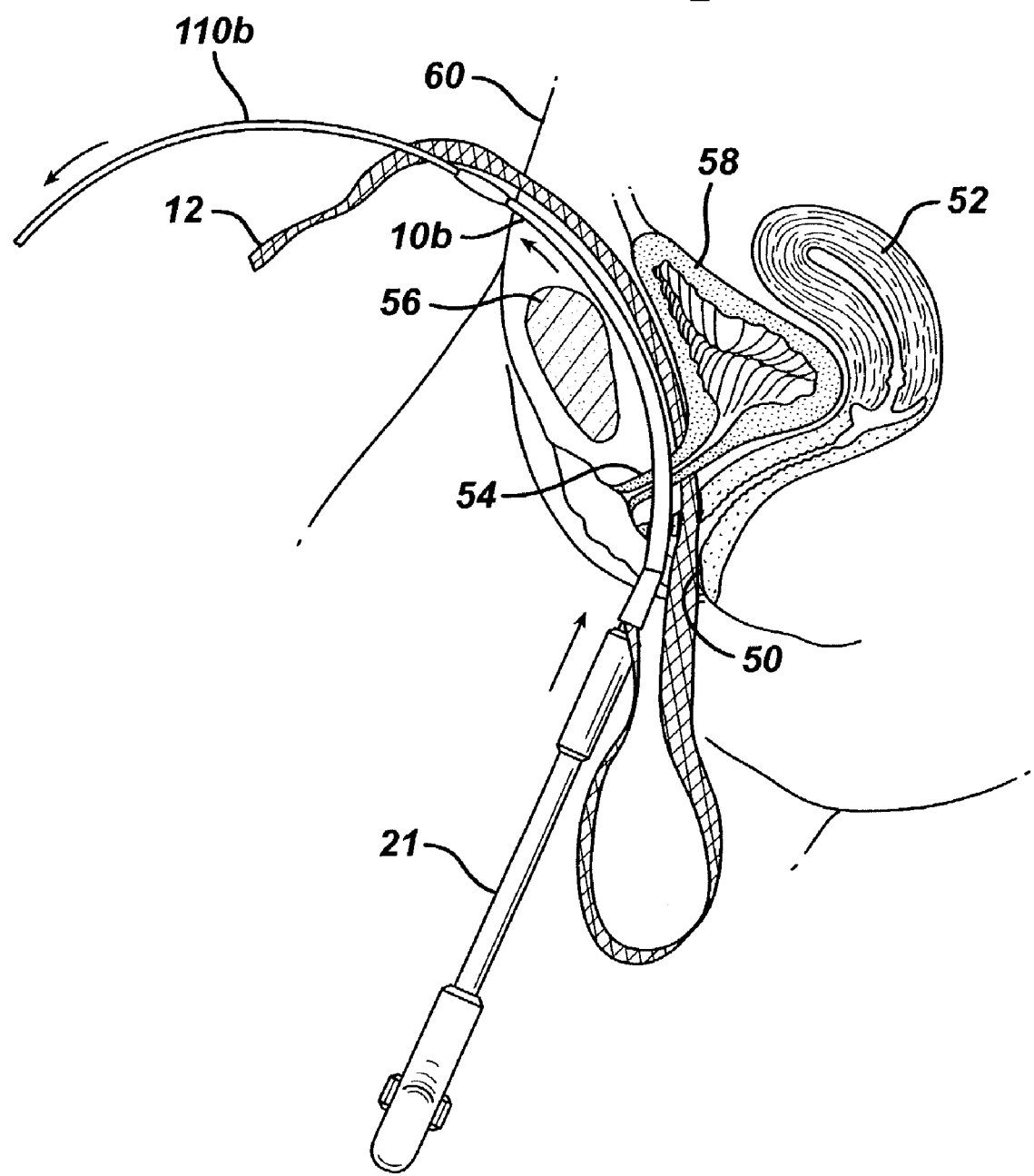
Figure 8H:
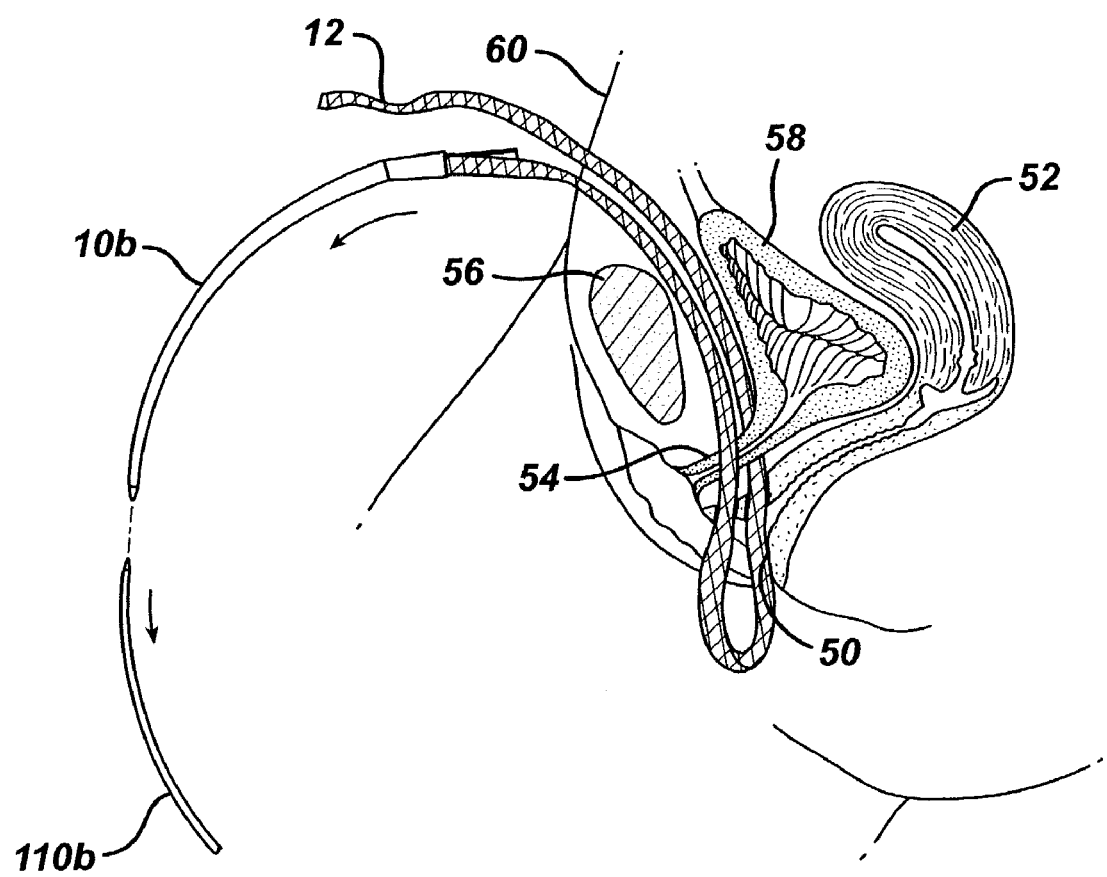
Figure 8I:
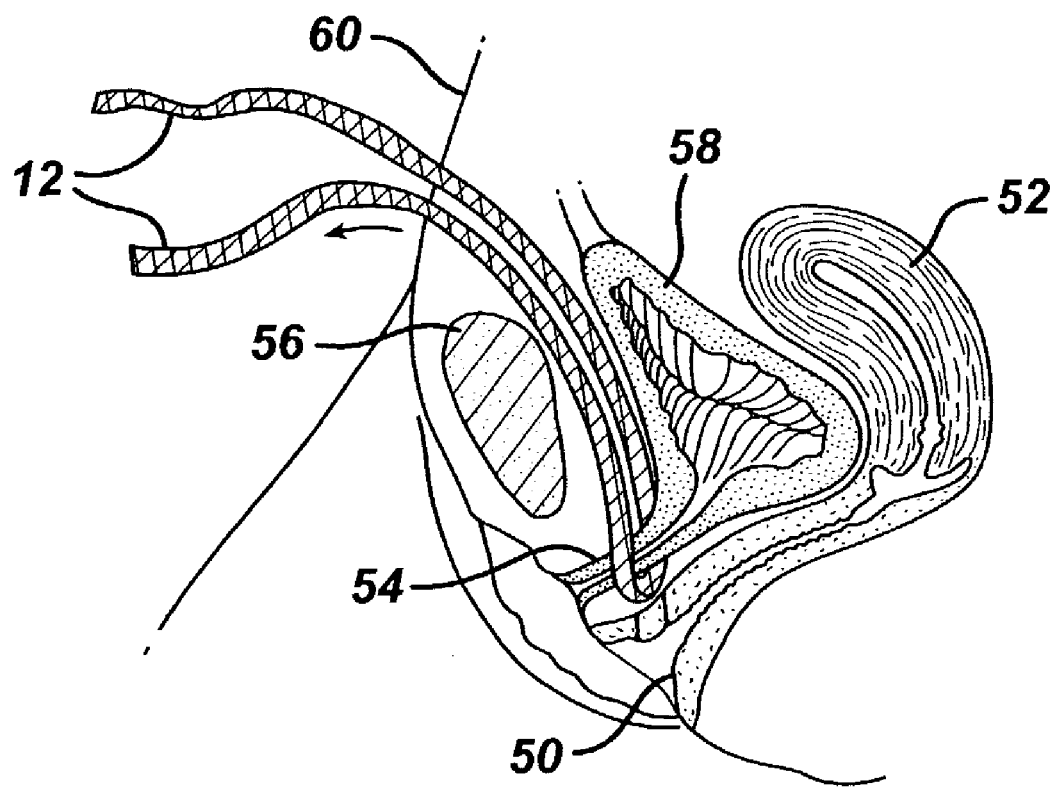

FIGS. 7f–g illustrate a loop coupling mechanism 160 attached to mesh 12 for engaging groove 120.

As would be appreciated by one skilled in the art, there exist multiple means for detachably connecting the mesh to the needle.

Since all procedures may be performed using a local anesthesia, the patient is able to provide feedback to the surgeon after mesh 12 is in place. Typically, the urinary bladder 58 is filled with a fluid, such as water, using a catheter and the patient is requested to cough. The surgeon is able to determine the operation of the urethra and may adjust the placement of the mesh 12, as necessary, by adjusting the ends of mesh 12 located at the outside of the abdomen 60, FIGS. 4h and 5h. After adjustments, the surplus mesh at the abdomen is cut off, and the ends of the mesh are secured within the abdomen and the abdomen is closed. Likewise, the incision at the vaginal wall is closed whereby the tissue flap seals the mesh between the urethra 54 and the wall of vagina 50.

Mesh 12 is left in the body and forms an artificial ligament attached to the abdominal wall that provides the support for the urethra as required in order to restore urinary continence to the patient.

Figure 14:
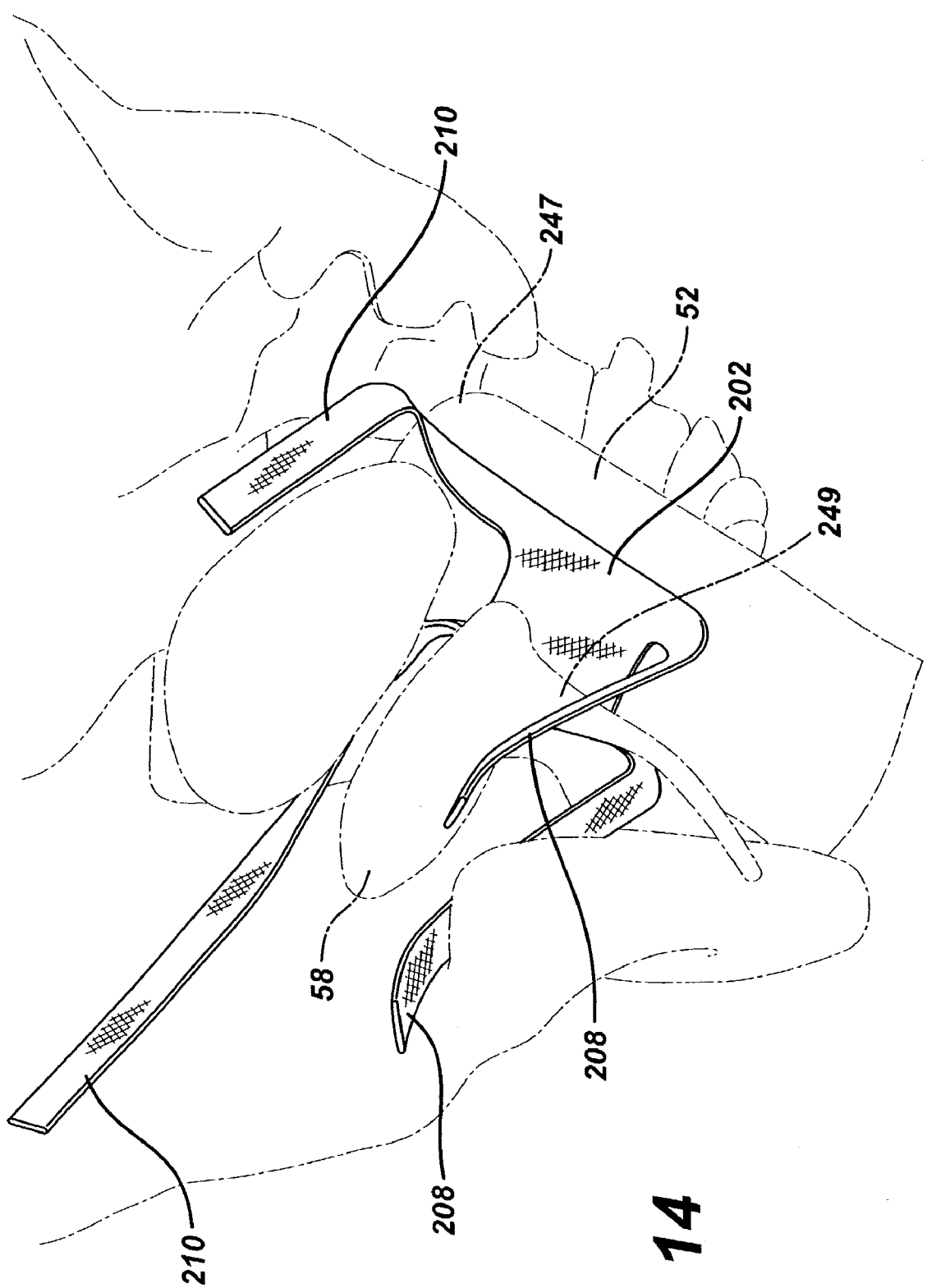
FIG. 14 is a perspective view illustrating the mesh of FIG. 9 in place within the body.

Referring now to FIGS. 9–18, surgical devices and methods for pelvic floor repair procedures will now be described in detail. According to one embodiment for cystocele repair, a mesh 200, illustrated in FIG. 9, is provided having a support sheet portion 202 for supporting the bladder having a distal end region 204 and a proximal end region 206 and a midline M—M. The mesh further includes two front attachment strips 208, and two rear attachment strips 210 for attaching the mesh within the pelvic cavity as will be described in more detail below. The support sheet portion 202, when positioned within the body as shown in FIG. 14, is positioned beneath the bladder 58 and has a length L such that the distal end region 204 is under the distal end of the bladder and the proximal end region 206 is positioned below and distal of the bladder neck 249. In the illustrated embodiment, the mesh 200 has a first recess 212 in the distal end region to ensure clearance from the uterus 52 and/or vaginal apex 247 when a hysterectomy has been preformed, and a second recess 214 at the proximal end region to ensure clearance from the bladder neck 249.

In a preferred embodiment, the length L of the support sheet portion 202 is approximately 3 inches to 6 inches, preferable 3–4 inches, and the width W is approximately 1 inch to 2 inches, with the first and second recesses having depths d1, d2 of approximately ¾–1 ½ inches and ½ to 1 inch respectively. Each of the rear and front attachment strips project outwardly from the corners of the support sheet portion at angles A1 and A2 relative to the mid-line M—M of the mesh. In the embodiment of FIG. 9, angle A1 is approximately 40 degrees and A2 is approximately 60 degrees, however, angles of approximately 30–60 degrees are acceptable. The lengths 12 of the front and rear attachment strips 208, 210 are preferable about 16 inches and have a width w2 of approximately ½ to 1 inch.

The mesh may be of any suitable biocompatible natural and/or synthetic material having a pore size sufficient for tissue in growth. In a preferred embodiment, the mesh is a non-absorbable knitted polypropylene mesh, such as PROLENE®) and PROLENE Soft®, manufactured by Ethicon, Inc. of Somerville, N.J. In an alternate embodiment, the mesh is a partially absorbable polypropylene and polyglactin mesh such as Vypro™, which is also manufactured by Ethicon, Inc., or may be any combination of non-absorbable and absorbable biocompatible material.

The attachment strips may be covered by individual slideably removable sheaths 216 that are held in place by secure attachment either the to the ends of the strips, or to a coupling mechanism that is affixed at the distal end of the strip and will be described in more detail below. The sheath can be made from any suitable materials, such as a plastic (i.e., polyethylene, polyester, or polyacetates), cloth (i.e., woven fabrics or non-woven fabrics of polyester fibers, acetate or nylon), or rubber (i.e., natural rubber, silicone or Tygon™).

The function of the sheath is multi-purpose. It provides a protective barrier, which prevents contamination of the mesh as it is passed through the vaginal canal. It also provides for a reduced frictional surface as compared to the mesh to allow the attachment strip to be pulled through the tissue without significant drag, which could result in the distortion and stretching of the mesh. It also provides for a stabilization of the structural integrity of the mesh in the width and diagonal directions. Following insertion of the attachment strips, the sheaths can be removed as will be described further below.

The present invention further includes other surgical devices that enable the mesh described above to be implanted via an "outside in" approach (i.e., from an abdominal approach) rather than a vaginal or "inside out" approach. One or more surgical guide needles are provided to facilitate the outside in approach and to enable the surgeon to pass the mesh attachment strips through the body quickly and in a manner that will safely avoid vital organs and nerves within the pelvic cavity. The configuration of the guide needle(s) may vary according to the points of attachment of the mesh attachment strips, which will dictate the path through the body.

Figure 10:
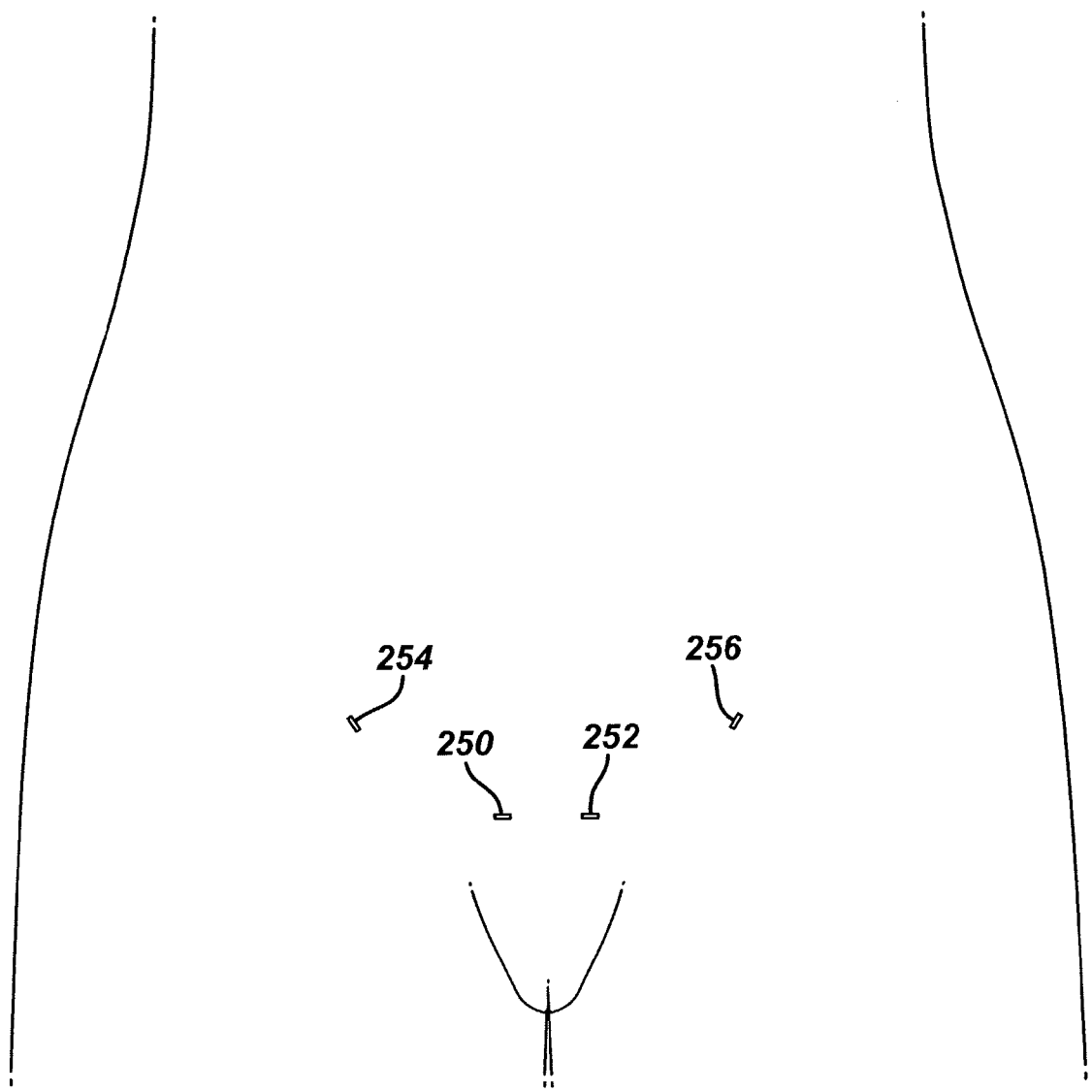
FIG. 10 is a frontal view of a female illustrating abdominal incision points according to one method for placing the mesh of FIG. 9.

According to a first embodiment of the invention, the mesh described above is used to repair a cystocele, and is placed to support the bladder with the front attachment strips 208 passing over the superior edge of the pubic bone and secured within the abdominal rectus muscle at first and second positions 250, 252, and the rear attachment strips 210 passing laterally on either side of the bladder and upwardly to the abdominal rectus muscle at third and fourth points 254, 256 that are lateral and caudal relative to that of the front attachment strips as shown in FIG. 10.

One method for placing this mesh includes using surgical guides that enter the body through the abdomen, pass through the abdominal rectus muscle, behind the pubic bone, and exit through a vaginal incision where they can be coupled with the front attachment strips to retract or pull the strips back through the channel created by the guide needles for securing the end of the front attachment strips in the abdominal rectus muscle. Initially, the patient is placed in the lithotomy position and a full-length anterior vaginal wall incision is made followed by dissection of the pubocervical fascial in a manner similar to traditional cystocele repair procedures. Next, two small puncture wounds are made that penetrate the abdominal wall, anterior to the pubic bone, one on each side of the midline, just above the synphysis, approximately 4 cm to 7 cm apart (see 250, 252 in FIG. 10). Subsequently, a surgical guide needle is passed from the first of the abdominal incisions 250 approximately following the curvature of the back of the pubic bone and exits from the anterior vaginal wall incision. See FIG. 12a. The pathway through the body is substantially similar to that shown in FIGS. 4a–4j above for placing a urethral sling.

Figure 11:
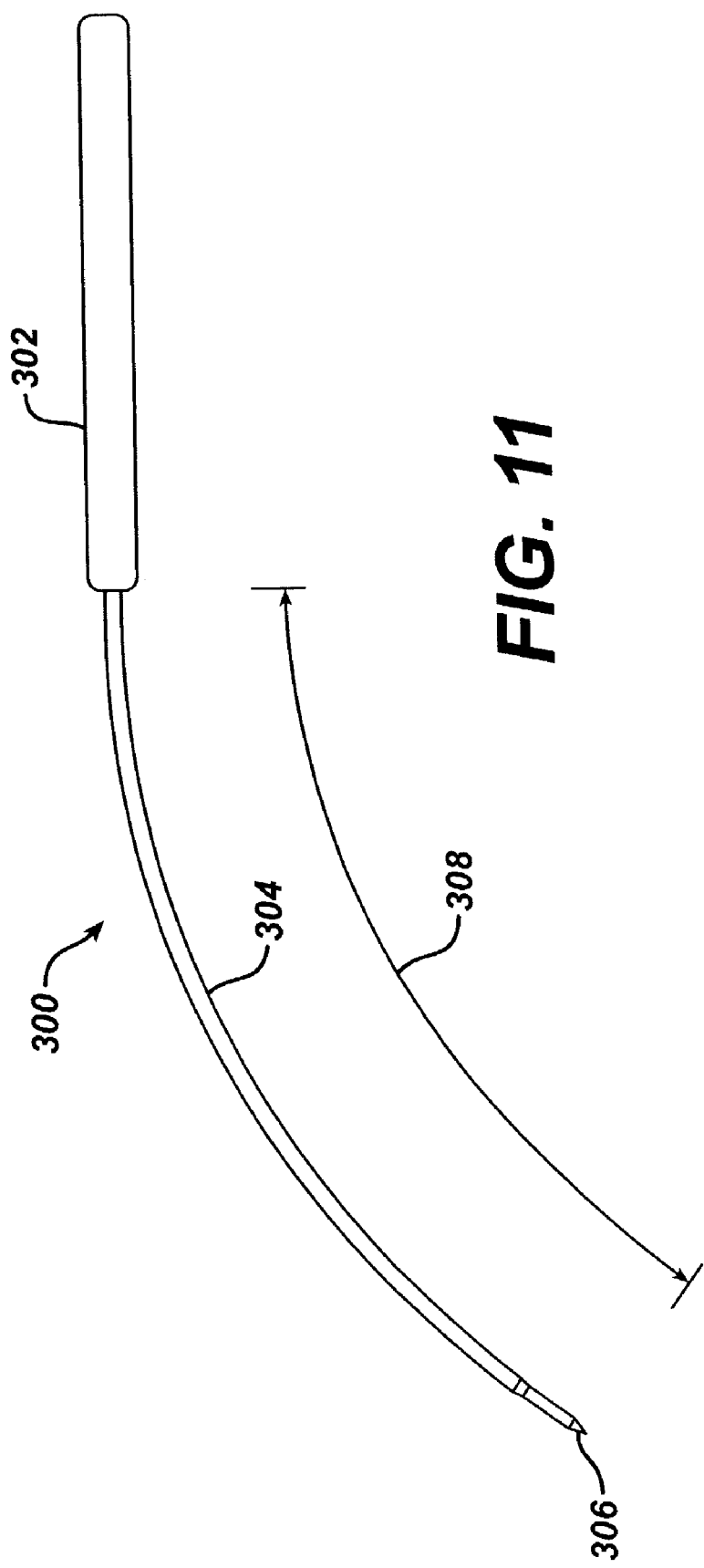
FIG. 11 is a side view of a one embodiment of a surgical guide needle for use in placing a mesh for treating pelvic floor prolapse.

One embodiment of a guide needle 300 that may be used to create this passage way is illustrated in detail in FIG. 11, and consists of two parts; a handle 302 and a shaft 304. The handle can have any suitable configuration that enables secured gripping of the device, and can be made of any suitable material such as plastic or stainless steel. The shaft 304 has a length 308 sufficient so that it will extend along the entire length of the path from the abdominal incision and out through the vaginal incision. The curvature of the needle is substantially identical to the path of the guide illustrated in FIG. 12a so that passage of the needle through the body creates the desired path. The guide needle has a blunt, non-cutting distal tip 306 that facilitates blunt dissection through the tissues.

Figure 12A:
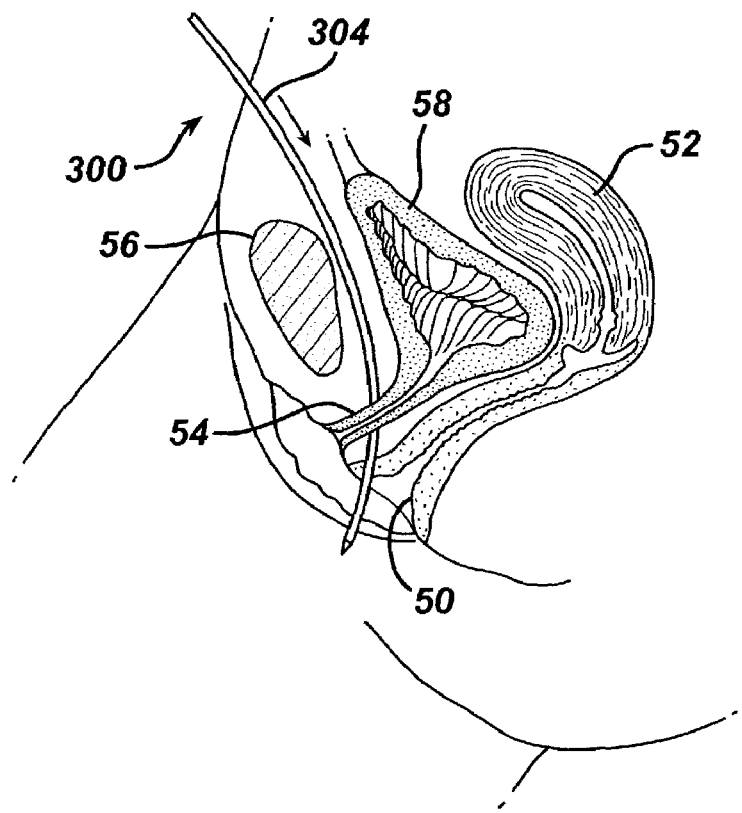
FIGS. 12a–12h diagrammatically illustrate several surgical steps in a method for placing a mesh for treating pelvic floor prolapse.
Figure 12B:
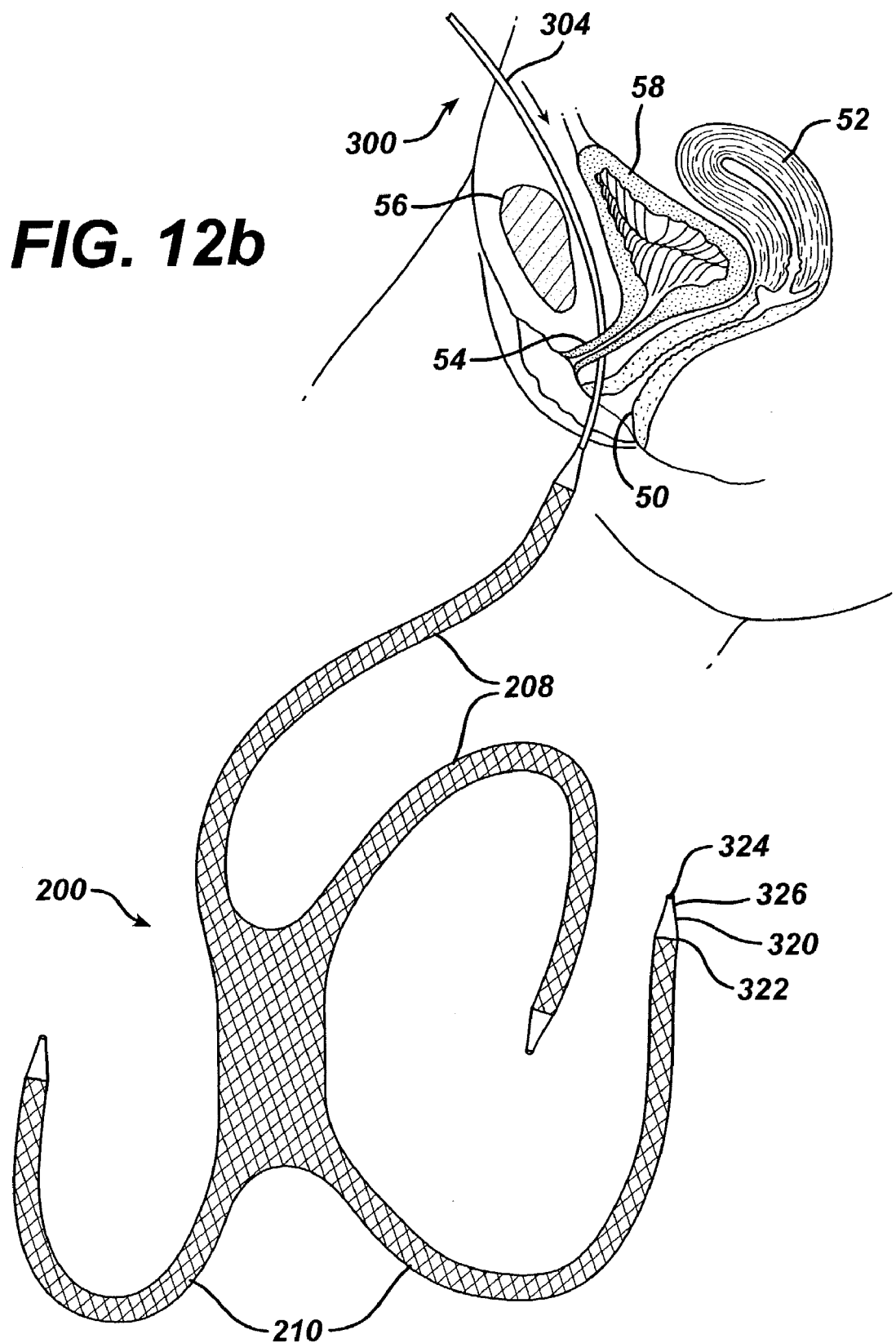
Figure 12C:
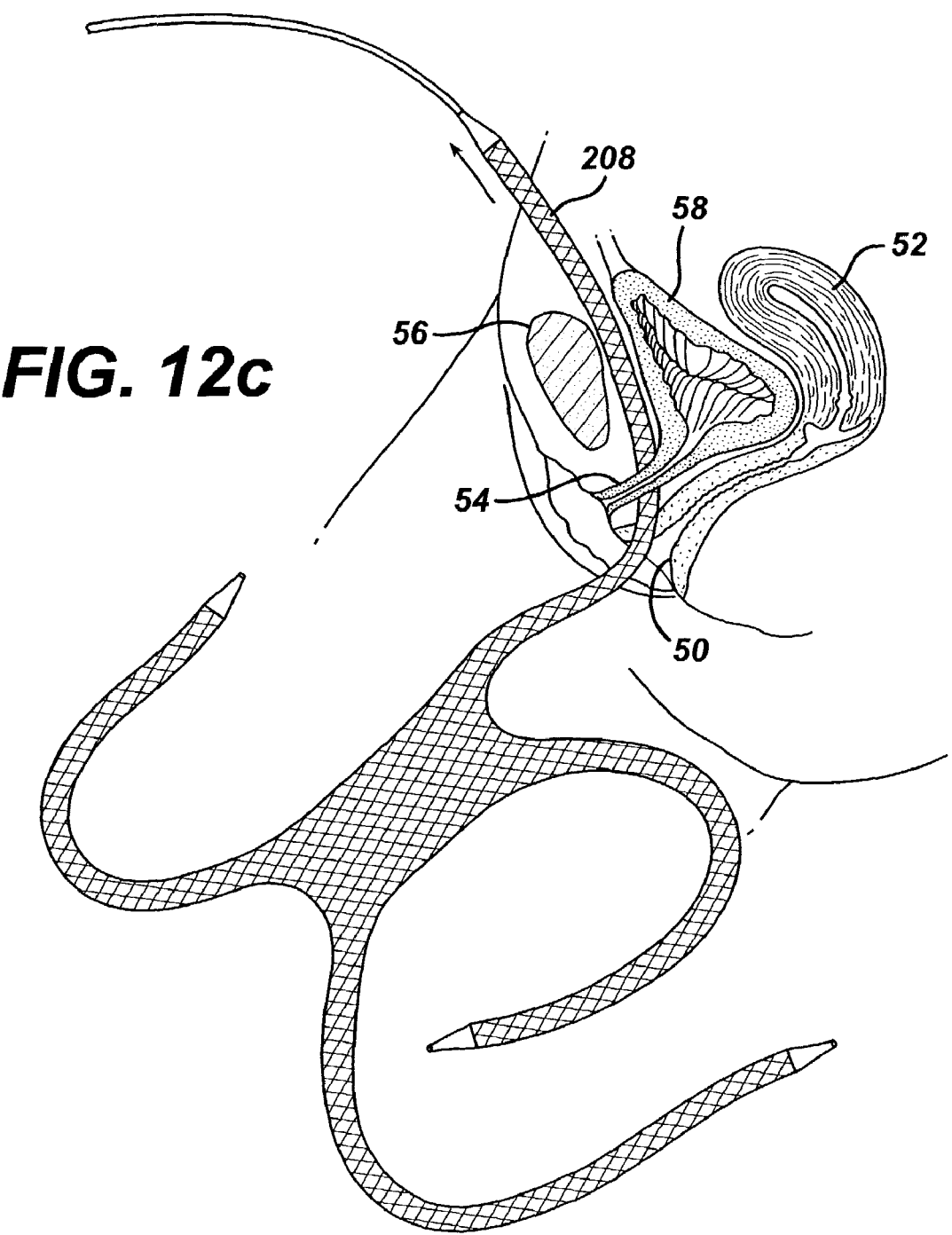
Figure 12D:
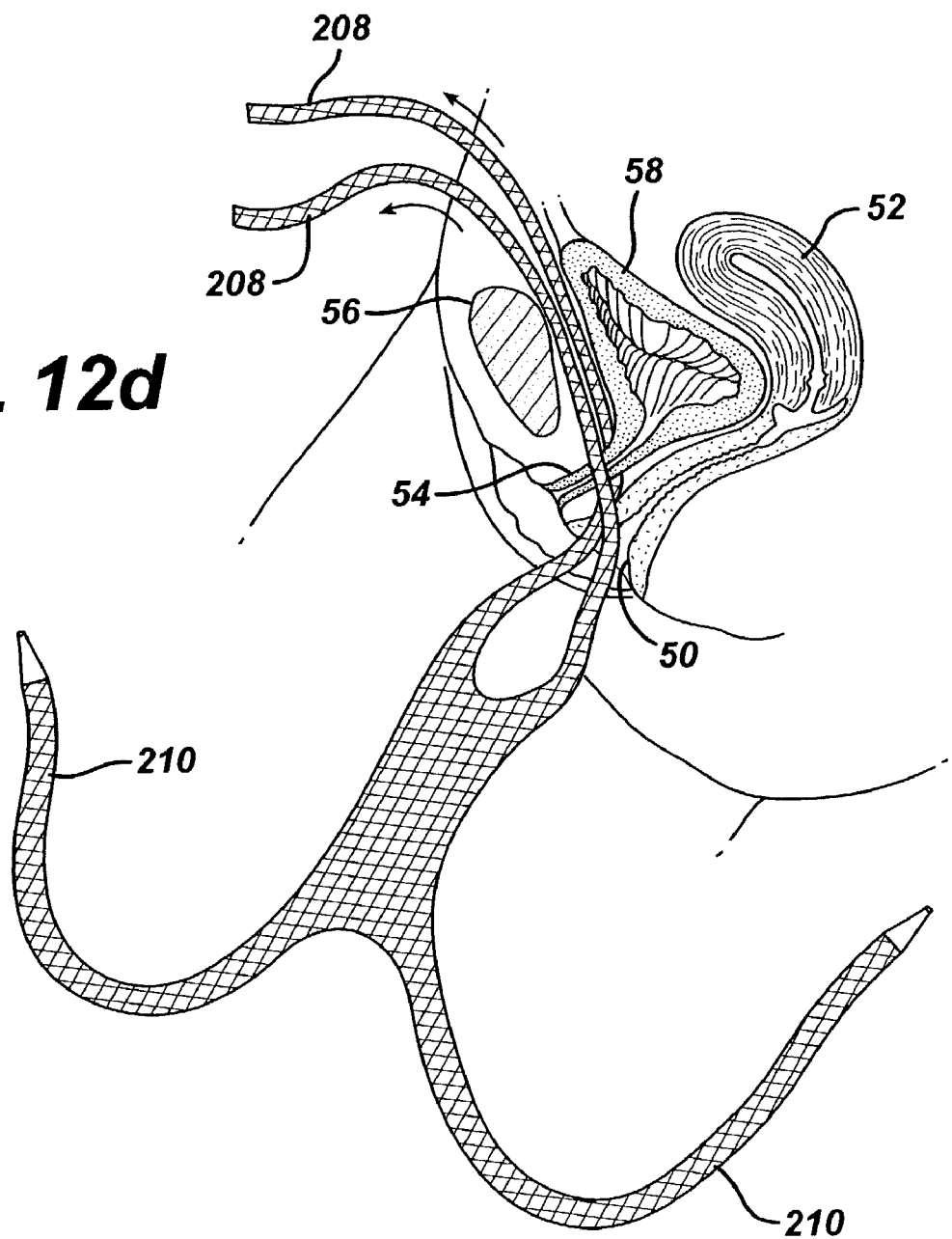
Figure 12E:
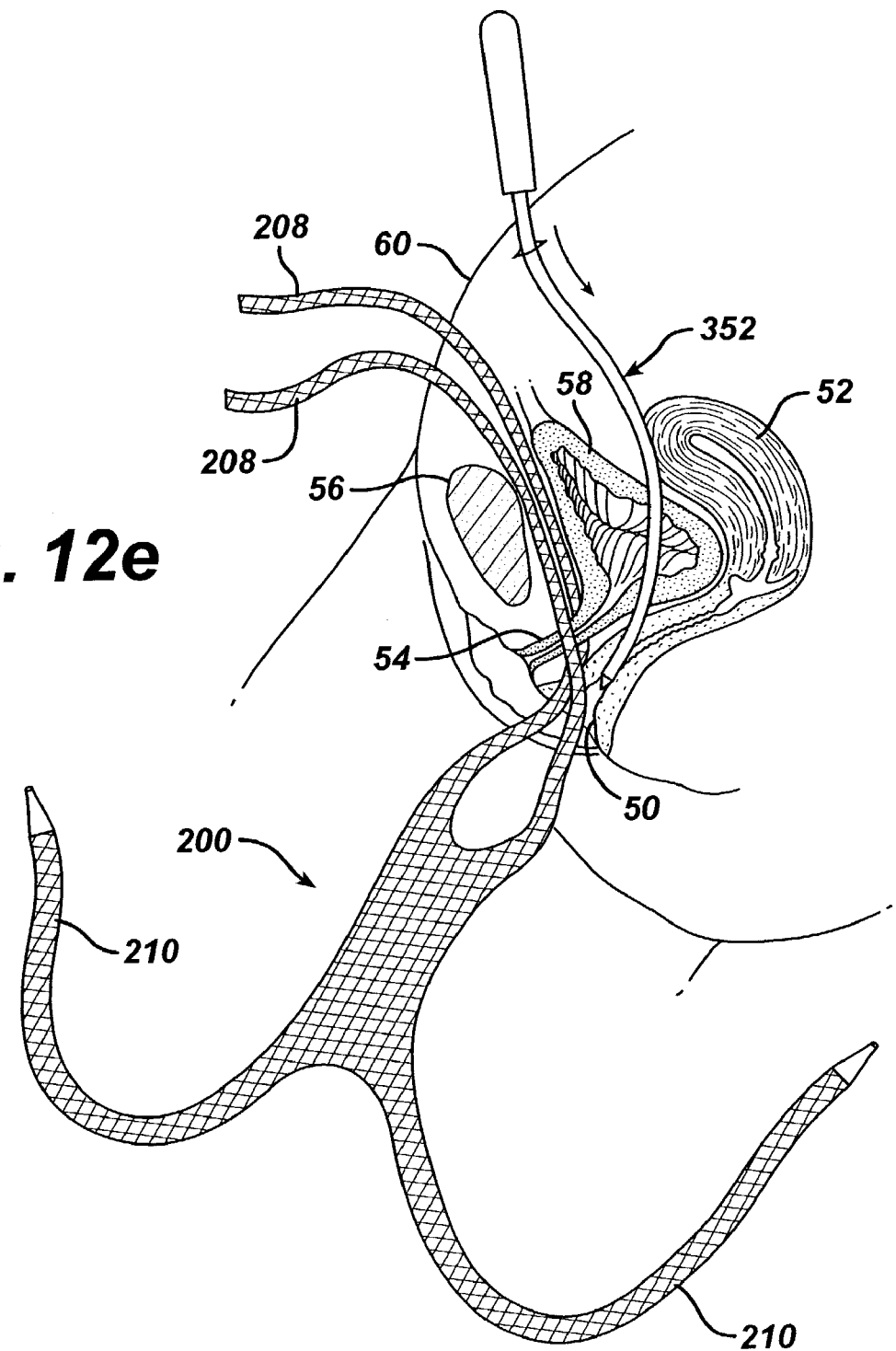
Figure 12F:
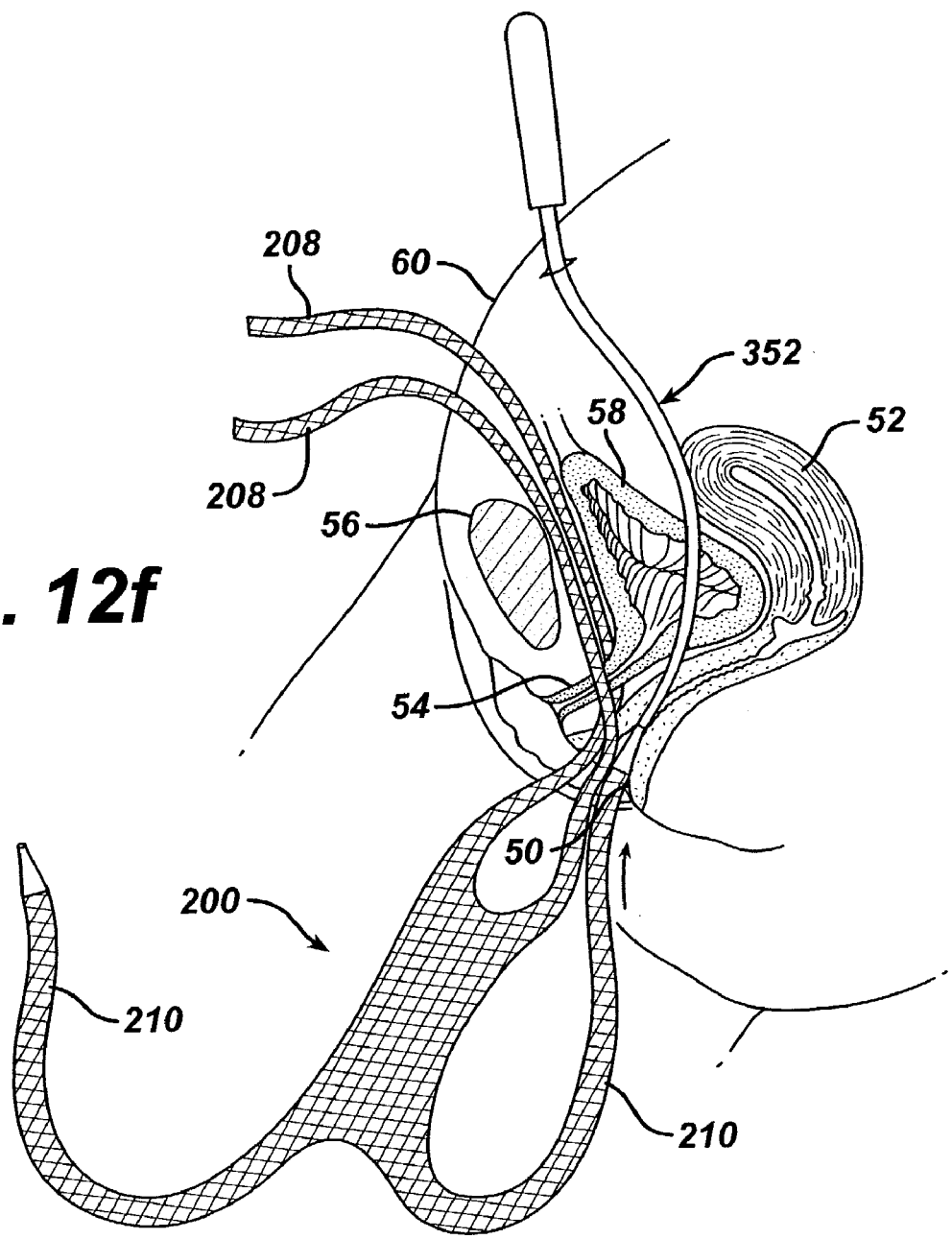
Figure 12G:
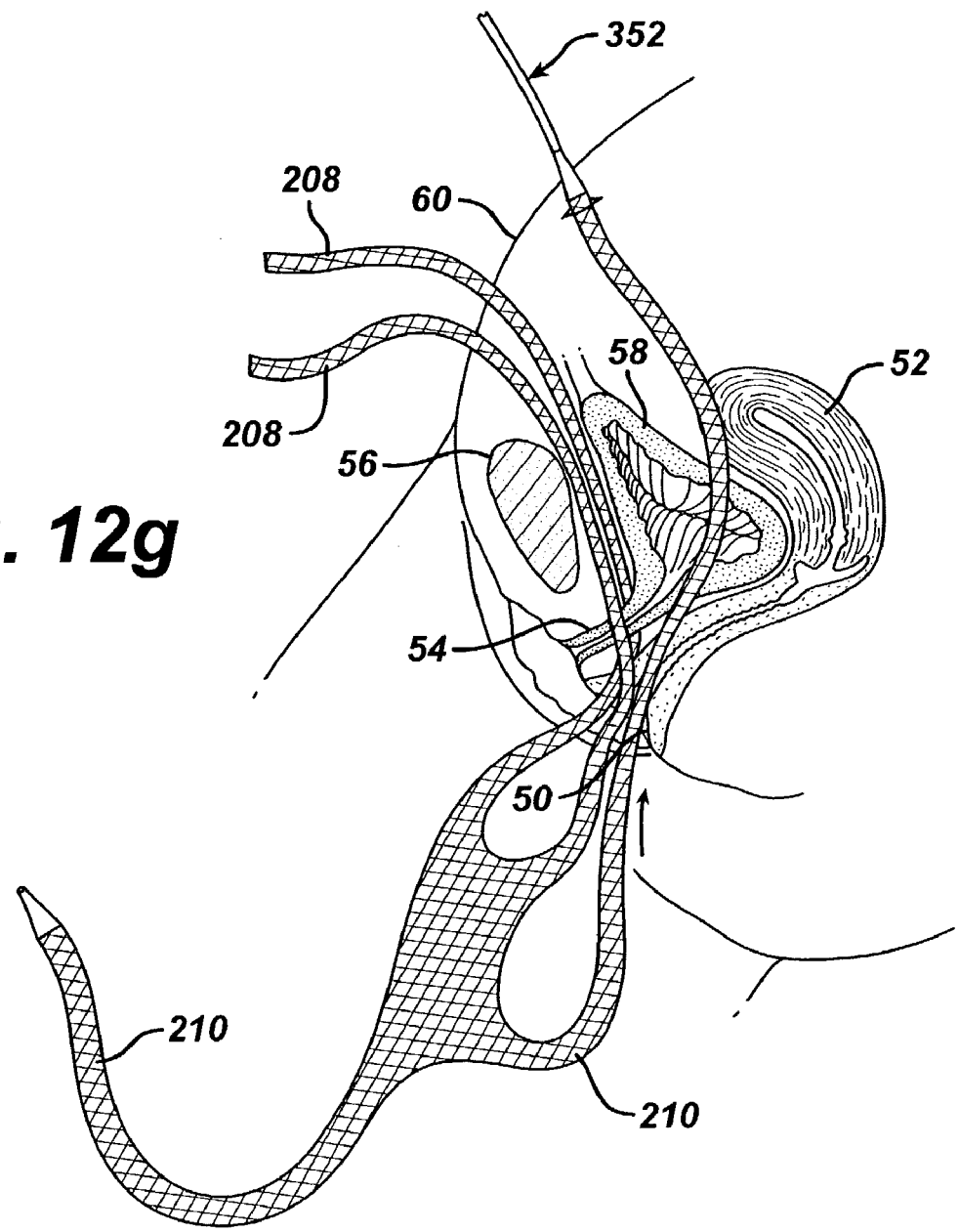

Once the guide needle tip extents through the vaginal incision (FIG. 12a), the guide needle is secured to the end of one of the front attachment strips (FIG. 12b) so that it may be pulled or retracted back through the path created by the guide needle (FIG. 12c). According to one embodiment, the mesh attachment strips each have a coupling mechanism attached to their distal ends. This coupling device may be similar to any of those shown in FIGS. 6a–6h and described above. In one particular embodiment, the coupling mechanism 320 is a polypropylene tube that is heat welded or otherwise adequately secured or bonded at a first end 322 to the distal end of the attachment strip. The tube has a recess or opening 324 in its second end 326 configured and dimensioned to receive therein the distal tip of the guide needle. Via the opening 324, the coupling device is press fit onto the distal end of the guide needle to secure it thereto.

Once the guide needle is secured to the first front attachment strip, the guide needle is retracted back through the body bringing the front attachment strip with it so that it now extends out through the abdominal incision (FIG. 12c). The same procedure is then repeated on the opposite side of the bladder and using the second abdominal incision 252 to pass the second front attachment strip out through the second abdominal incision (see FIG. 12d).

To place the rear attachment strips within the abdominal rectus muscle a similar procedure is used as in the placement of the front attachment strips. Third and fourth 254, 256 small incisions are made through the skin and fascial layer of the abdominal rectus muscle. These two incisions, as shown in FIG. 10, are located approximately 6 cm to 8 cm caudal to the superior ridge of the pubic synphysis, and 6 cm to 7 cm lateral on each side of the midline of the synphysis. For this passage of the rear attachment strips, it is useful to select a guide that contains a compound curve, similar to that illustrated in greater detail in FIG. 13. The shaft 350 of the guide needle 352 contains a first curved portion 354 at the distal end 356 with a radius R1 and a second curved portion 358 in the mid section of the shaft proximal of the first curved potion, which can be in a different plane than the first curve, with a radius R2. A third curved portion 360 is located at the proximal end 362 of the shaft with a radius R3. The length of each section, the plane of the curve and the radii of the curves can be the same or different creating various shaped shafts that may facilitate a given pathway through the body. The compound curve allows for a change of direction of the blunt, cutting tip 366 of the guide needle as is passes from the incision through the fascia and pelvic cavity and out of the anterior vaginal wall incision into the lumen of the vagina. The serpentine like route enables the guide to avoid vital organs and vessels within the pelvic cavity. In the illustrated embodiment, the length 370 of the first curved portion is approximately 8.9 inches and radius R1 is approximately 2.25 inches; the length 372 of the second curved portion is approximately 3.5 inches and radius R2 is approximately 2.0 inches; and the length 374 of the third curved portion is approximately 1.88 inches and radius R3 is approximately 2.0 inches.

To place the rear attachment strips, the surgeon inserts a finger into the distal portion of the anterior wall incision of the vagina. The bladder is located and palpated. A blunt dissection is made through the pubocervical fascia on one side of the bladder and the finger is directed up towards the abdominal incision on that side. The guide needle is then inserted into the incision on that side. The inside curvature of the distal portion of the guide needle is positioned to face the midline of the synphysis. The blunt tip of the guide needle is then advanced as the surgeon palpates the tip with the finger and aligns the guide needle to pass around any vital organs or vessels. At this point the tip of the guide needle is passed through the remaining fascial tissue between it and the surgeons finger, and subsequently advanced following the first curvature until the transition between the first and second curvatures is reached in the abdominal rectus muscle. The guide needle is then rotated to align the tip with the channel of the vaginal lumen, and advanced along the direction of the second curvature. Once the guide needle tip extents at or near the introitus of the vagina (see FIG. 12e), the guide needle is secured to the end of one of the rear attachment strips so that it may be pulled or retracted back through the path created by the guide needle and out through the first caudal abdominal incision (see FIGS. 12f–12g).

Figure 12H:
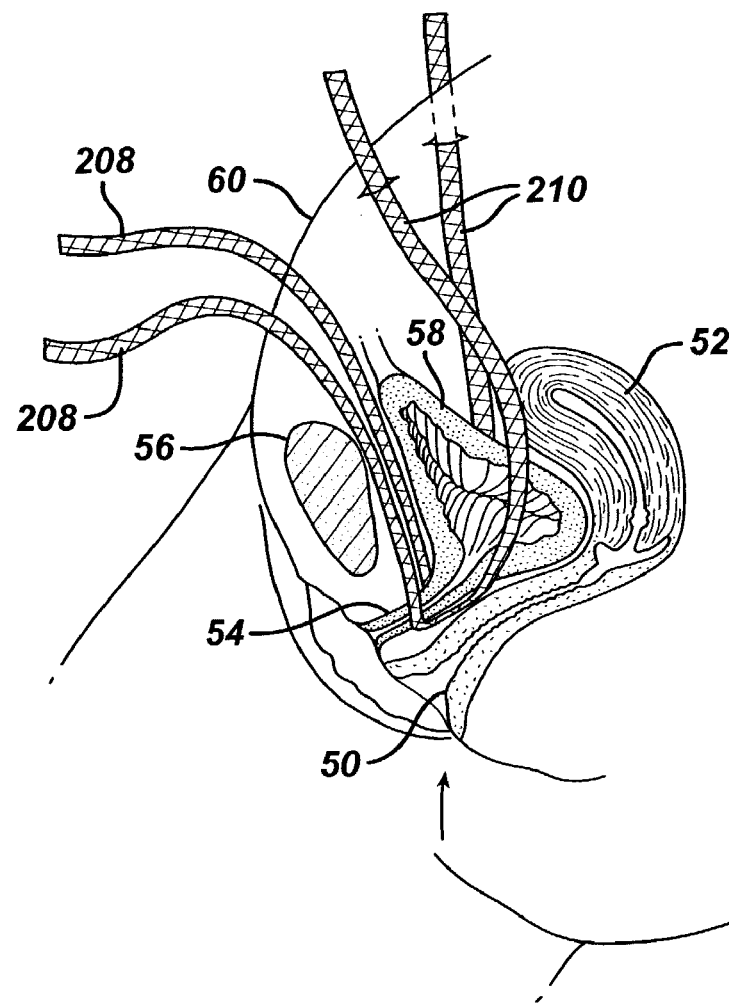

The same procedure is then repeated on the opposite side of the bladder and using the fourth abdominal incision 256 to pass the second rear attachment strip out through that incision (FIG. 12h).

This abdominal passage and attachment procedure can also be accomplished with the aid of a laparoscope. The laparoscope is inserted through an incision in the umbilical area and directed towards the caudal incision. With this technique the passage of the tip of the guide can be visualized as it passes through the pelvic cavity and into the anterior vaginal wall incision.

Once all four of the attachment strips have been placed, the coupling means are removed from the strips. The supporting mesh structure is adjusted under the bladder and final positioning is made by pulling on the attachment strips (see FIGS. 12h and 14). The protective sheaths covering the attachment strips are removed one at a time and the supporting mesh is held fast in place by the frictional forces between the surrounding tissue and the attachment strips. The excess material is cut from the abdominal ends of the attachment strips and the ends are left sub cutis. The abdominal incision can be sutured or closed with a skin closure adhesive such as DERMABOND™, by Ethicon, Inc. of Somerville, N.J. The vaginal incision is sutured closed using a typical technique.

Figure 15A:
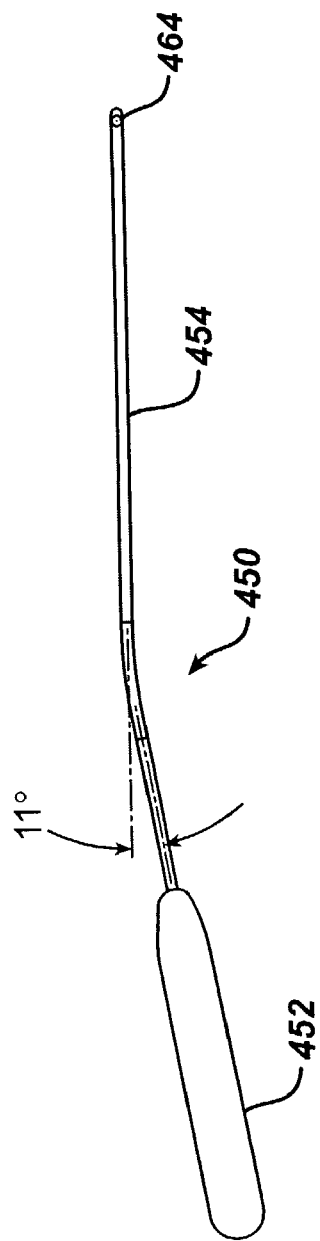
FIGS. 15a and 15b are top and side views of one embodiment of a surgical guide needle that can be used in placing strips of the mesh of FIG. 9 through the obturator fossa of a patient.
Figure 15B:
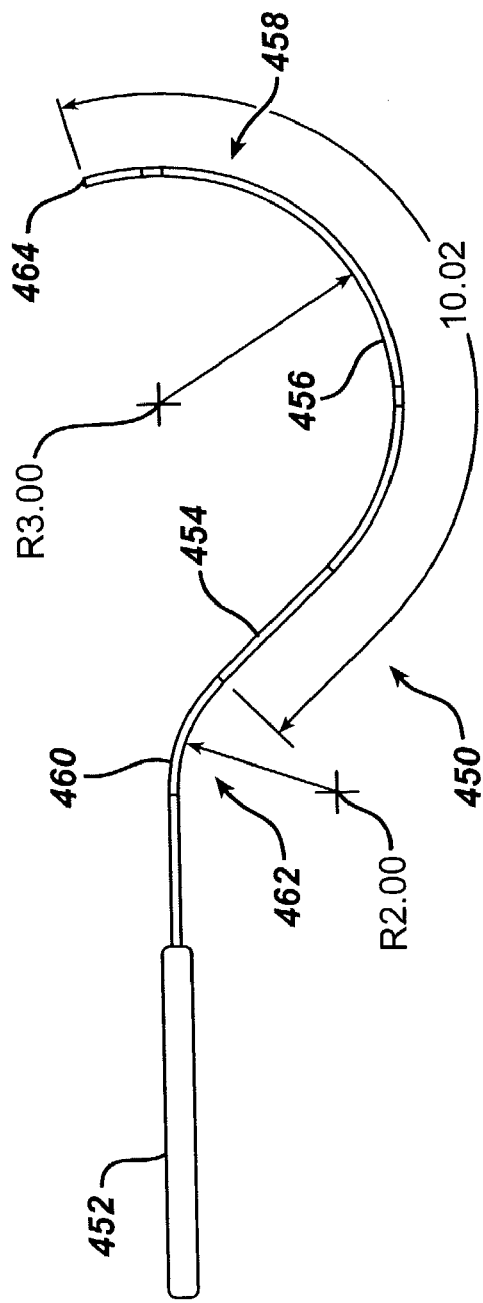
Figure 16:
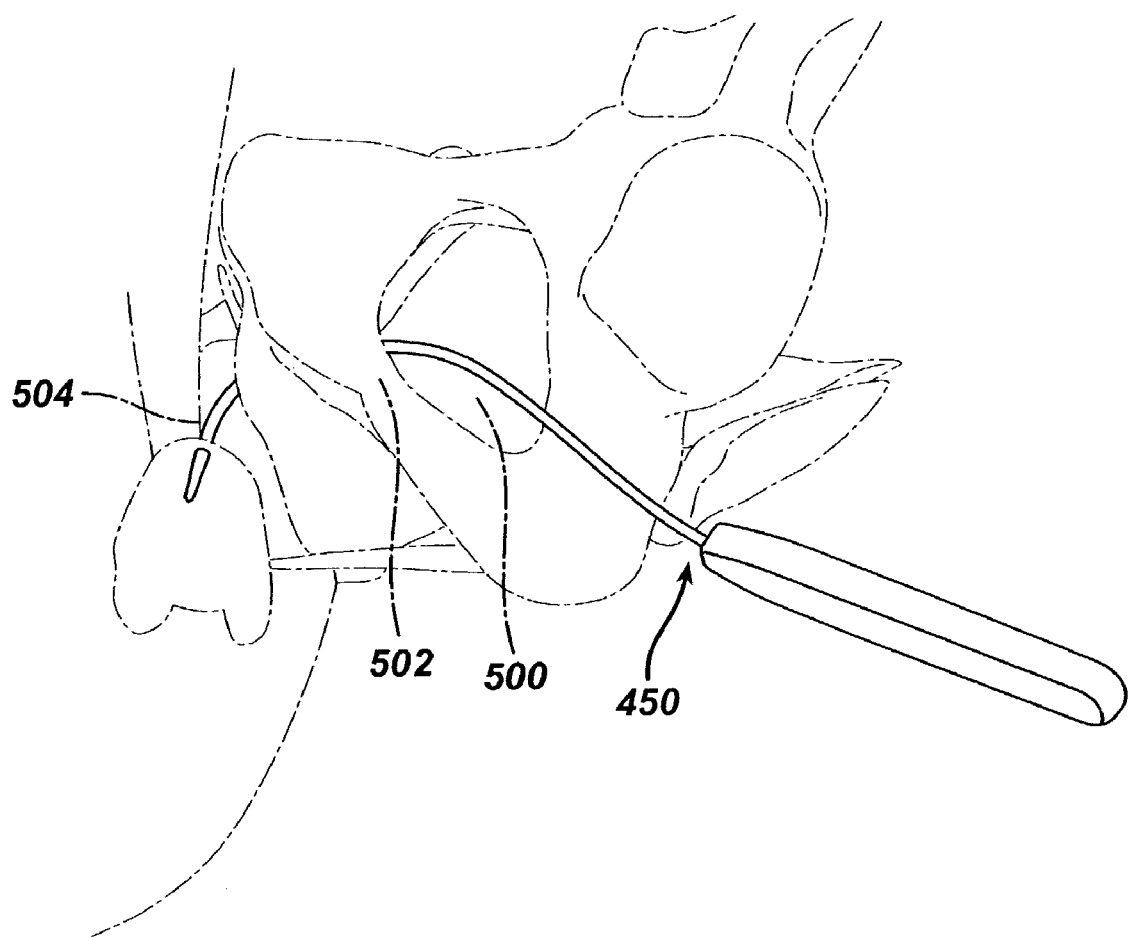
FIGS. 16 and 17 are a perspective views illustrating a steps in a method for placing strips of the mesh of FIG. 9 through the obturator fossa.
Figure 17:
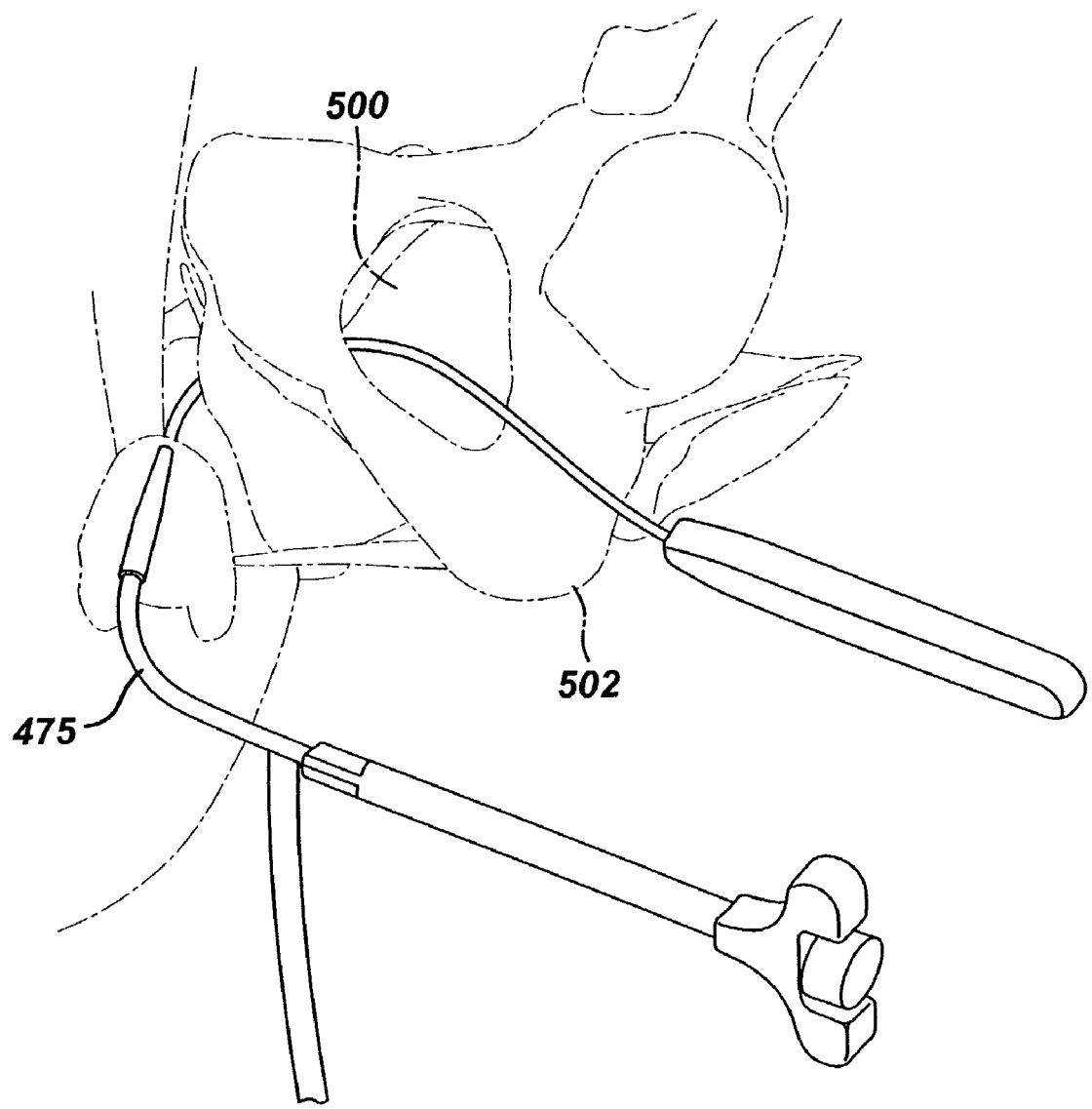

Repair of a prolapse can also include passage of the guides and mesh front attachment strips through the obturator fossa or any other fossa in the pelvic bone. The use of the guides is enhanced by incorporation of a compound curve in the shaft. An example of a guide needle with a compound curved shaft useful for placing a mesh attachment strip through the obturator fossa is shown in FIGS. 15a and 15b. The guide needle 450 has a handle 452 and a shaft 454. The shaft has a first curve 456 at the distal section, and a second curve 458 at a middle section 462 proximal of the distal section. The purpose of the first curve is to set the path of the tip 464 of the guide needle as it passes from the external surface of the obturator fossa 500 around the obturator bone 502, into the incision on the anterior vaginal wall 504 (FIG. 16). The tip of the guide then extends into and out of the vaginal introitus. FIG. 16 shows the position of the guide needle 450 within the body just prior to coupling of the attachment strip to the guide. The guide needle is then secured to the end of one of the front attachment strips as described above, or alternatively, as shown in FIG. 17, to the distal end of a second needle 475 that itself is coupled to the attachment strip. This alternate attachment method using a second needle is similar to that described above in conjunction with FIGS. 4a–4j, and could also be alternatively used when placing mesh attachment strips via any pathway described herein. The attachment strips can then be pulled or retracted back through the path created by the guide needle and out through the first obturator incision.

The purpose of the second curve is to allow the handle to be maneuvered close to the body without pressing against it or having portions of the body, particularly the pubic region, from limiting the path of the shaft. With the offset nature of the second curve, as illustrated in FIG. 15a, the section 462 becomes a pivot point so that a small lateral movement of the handle in one direction causes a large movement of the tip of the shaft (464) in the opposite direction. The offset nature of the handle further allows for a better fit against the patient's body.

Figure 18A:
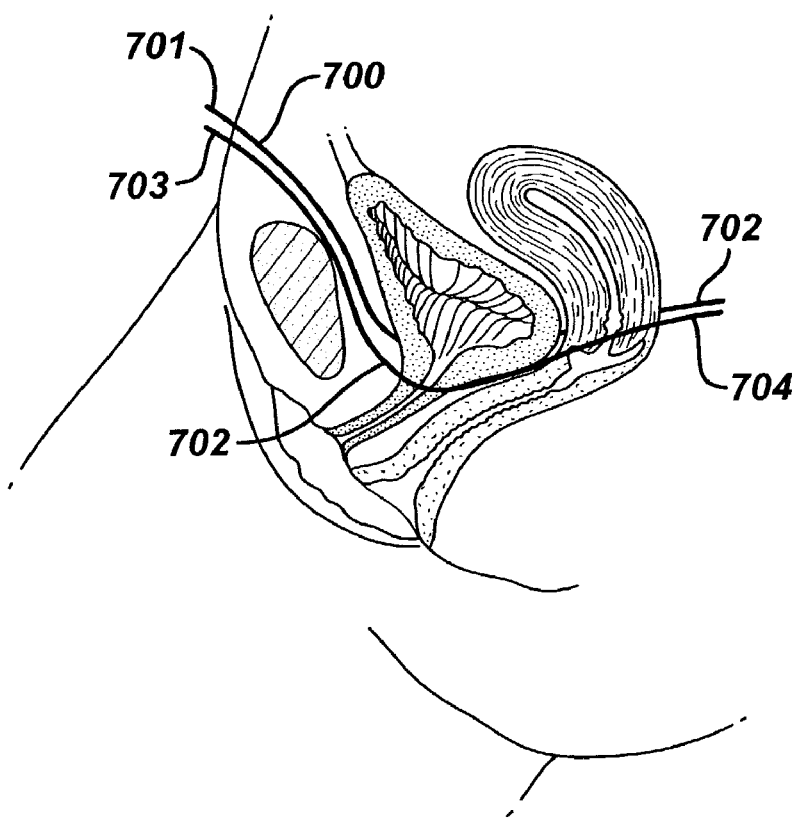
FIGS. 18a–18d are perspective views illustrating various mesh embodiments in place within the body.

The procedures and devices described in detail above can also be use to implant various other mesh configurations for pelvic prolapse repair, such as those illustrated in FIGS. 18a–18d. FIG. 18a illustrates a mesh consisting of a first mesh strip 700 having a front end 701 and a rear end 702, and a second mesh strip 703 having a front end 704 and a rear end 705. The front end and rear end of each strip may be placed as described above in conjunction with the front and rear attachment strips respectively of the mesh of FIG. 9. In the alternative, the rear ends could be attached within the pelvic cavity, such as to the sacrospinous ligament or the iliococcygeous muscle. Preferably, the strips are positioned under the lateral aspects of the bladder, as shown in FIG. 18a.

Figure 18B:
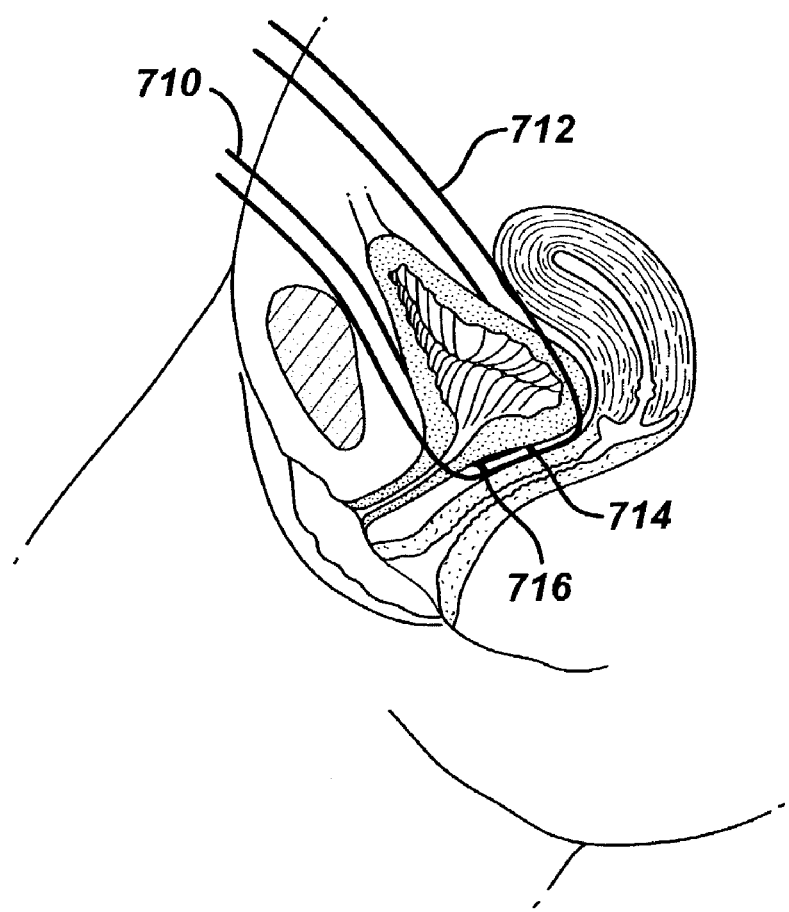
Figure 18C:
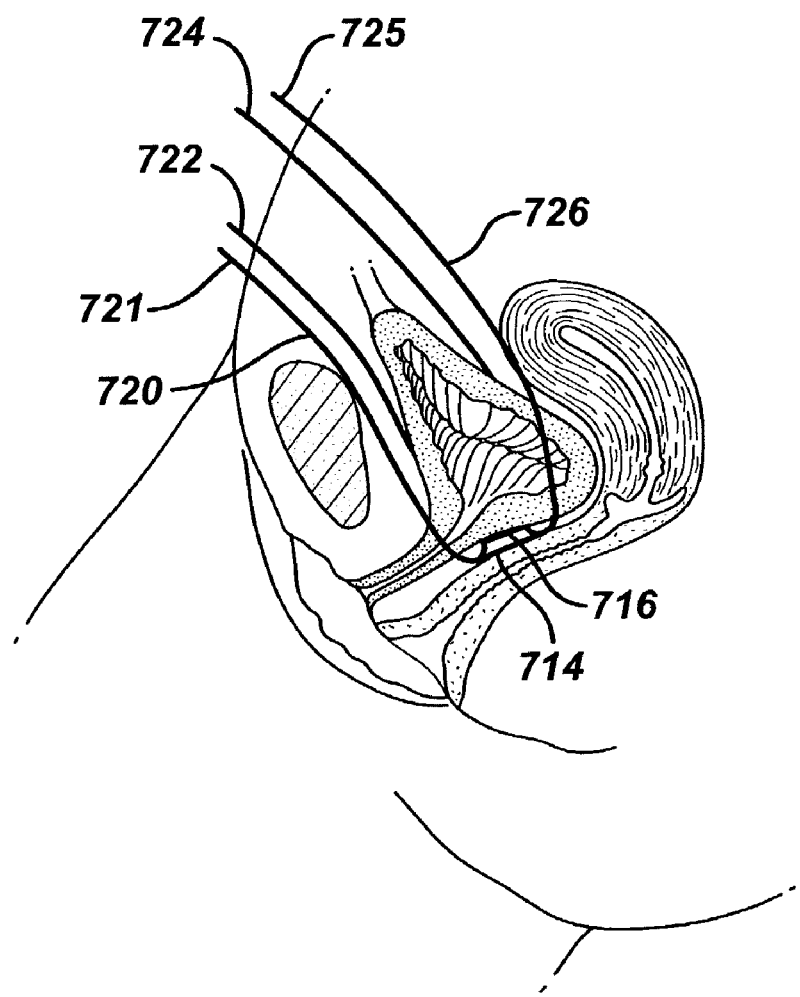
Figure 18D:
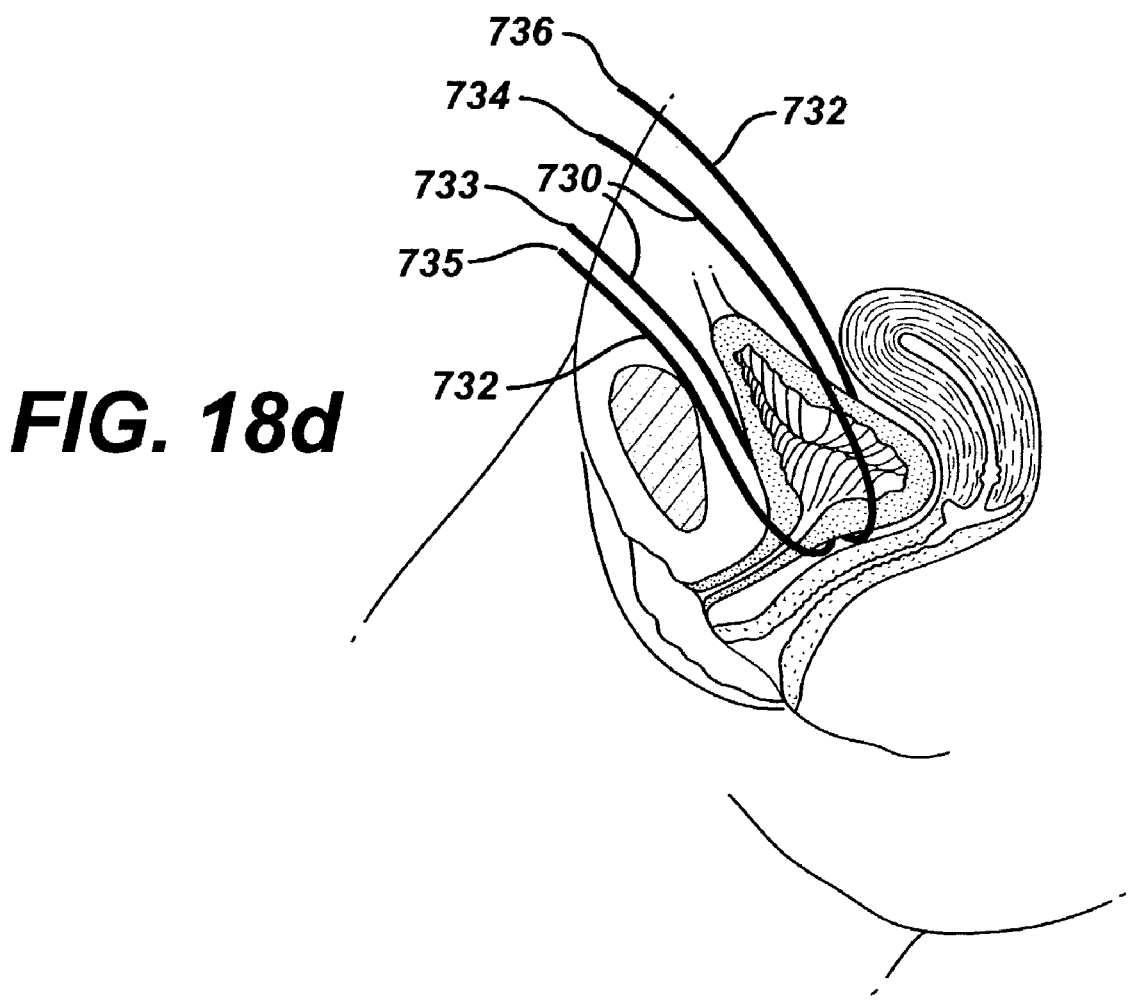

In another embodiment shown in FIG. 18b, the mesh similarly includes first and second primary mesh strips 710, 712, but also includes first and second mesh crossing strips 714, 716 extending between the first and second strips. The first mesh crossing strip 714 is preferably positioned just distal of the urethra at the bladder neck, and the second crossing strip 716 positioned just proximal of the posterior aspect of the bladder. In an alternate embodiment shown in FIG. 18c, first and second ends 721, 722 of the first primary mesh strip 720 are placed in a manner similar to the first and second front attachment strips of the mesh of FIG. 9, whereas first and second ends 724, 725 of the second primary mesh strip 726 are placed in a manner similar to the first and second rear attachment strips of that mesh. Thus, the first primary mesh strip will lie just distal of the urethra at the bladder neck, the second primary mesh strip will lie just proximal of the posterior aspect of the bladder, and the first and second cross strips 714, 716 will lie under the lateral aspects of the bladder. Finally, FIG. 18d illustrates yet another embodiment of a mesh including first and second strips 730, 732 that cross over one another under the mid-portion of the bladder. First ends 733, 735 of the first and second strips can be placed in the same manner as the front attachment strips of the mesh of FIG. 9, whereas the second ends 734, 736 can be placed in the same manner as the rear attachment strips of that mesh.

Although several embodiments of a mesh for pelvic floor prolapse repair have been described, those skilled in the art will recognize that various other mesh configurations can also be used in conjunction with the procedures and techniques described herein. It will be further apparent from the foregoing that other modifications of the inventions described herein can be made without departing from the spirit and scope of the invention. Accordingly, it is not intended that the invention be limited, except as by the appended claims.

What is claimed is:

1. A surgical kit for performing a surgical procedure on a patient to restore a prolapsed organ within a patient's pelvic region comprising:
   a mesh for supporting the organ, the mesh including a support sheet portion to be positioned substantially beneath the organ having a distal end region and a proximal end region, first and second front attachment strips extending from the proximal end region, and first and second rear attachment strips extending from the distal end region;
   a first guide needle for penetrating tissue within the patient's body to create a passageway through the patient's pelvic region through which the first or second front or rear attachment strips can be pulled, the guide needle having a proximal end and a tissue penetrating blunt tip at a distal end, and defining in part a curved shaft having a first curvature; and
   coupling means for coupling a distal end of each of the first and second front and rear attachment strips to the distal end of the guide needle,
   wherein, for each of the first and second front and rear attachment strips, the coupling means is a coupling element fixedly secured at a first end to a distal end of the attachment strips, and having an opening at a second end dimensioned to receive therein and securely engage the distal end of the guide needle.

2. A surgical kit for performing a surgical procedure on a patient to restore a prolapsed organ within a patient's pelvic region comprising:
   a mesh for supporting the organ, the mesh including a support sheet portion to be positioned substantially beneath the organ having a distal end region and a proximal end region, first and second front attachment strips extending from the proximal end region, and first and second rear attachment strips extending from the distal end region;
   a first guide needle for penetrating tissue within the patient's body to create a passageway through the patient's pelvic region through which the first or second front or rear attachment strips can be pulled, the guide needle having a proximal end and a tissue penetrating blunt tip at a distal end, and defining in part a curved shaft having a first curvature; and coupling means for coupling a distal end of each of the first and second front and rear attachment strips to the distal end of the guide needle, wherein, for each of the first and second front and rear attachment strips, the coupling means comprises a needle element fixedly coupled at a proximal end to a distal end of the attachment strip, and a coupling device for coupling a distal end of the needle element to the distal end of the guide needle.

3. The surgical kit according to claim 2, wherein the coupling device has a first opening at a first end dimensioned to receive therein and securely engage the distal end of the needle element and a second opening at a second end dimensioned to receive therein and securely engage the distal end of the guide needle.

4. A surgical kit for performing a surgical procedure on a patient to restore a prolapsed organ within a patient's pelvic region comprising:

a mesh for supporting the organ, the mesh including a support sheet portion to be positioned substantially beneath the organ having a distal end region and a proximal end region, first and second front attachment strips extending from the proximal end region, and first and second rear attachment strips extending from the distal end region;

a first guide needle for penetrating tissue within the patient's body to create a passageway through the patient's pelvic region through which the first or second front or rear attachment strips can be pulled, the first guide needle having a proximal end and a tissue penetrating blunt tip at a distal end, and defining in part a curved shaft having a first curvature;

a second guide needle for penetrating tissue within the patient's body to create a passageway through the patient's pelvic region through which the first or second front or rear attachment strips can be pulled, the second guide needle having a proximal end and a tissue penetrating blunt tip at a distal end and defining in part a curved shaft; and coupling means for coupling a distal end of each of the first and second front and rear attachment strips to the distal end of the first and second guide needles, wherein the curved shaft of the second guide needle has a curvature different than that of the first guide needle, and wherein the passageway created by the first guide needle is different than that of the second guide needle.

5. The surgical kit according to claim 4, wherein the organ is the patient's bladder, and wherein the curvature of the first guide needle is such it can extend from an exterior of the abdomen, around the pubic bone, and into the vagina.

6. The surgical kit according to claim 5, wherein the curvature of the second guide needle is such that it can extend from an exterior of the abdomen at a location caudal and lateral to that of the first guide needle, around the side of the bladder, and out into the vagina.

7. The surgical kit according to claim 6, wherein the curvature of the second guide needle forms a compound curve.

8. The surgical kit according to claim 4, further comprising, for each of the first and second front and rear attachment strips, a removable sheath substantially covering the attachment strip.

9. A method for restoring a prolapsed organ within a patient's pelvic cavity comprising the steps of:

providing a mesh for supporting the prolapsed organ, the mesh including a support sheet portion to be positioned substantially beneath the organ having a distal end region and a proximal end region, first and second front attachment strips extending from the proximal end region, and first and second rear attachment strips extending from the distal end region;

providing at least one guide needle;

for each of the first and second front attachment strips, using the guide needle to create first and second passageways, one at a time, through the patient's body from an exterior of the body and into the patient's vagina, coupling the guide needle to a distal end of the attachment strip using a coupling means, and retracting the guide needle and attached attachment strip through the body through the passageway;

for each of the first and second rear attachment strips, using the guide needle to create third and fourth passageways, one at a time, through the patient's body from the exterior of the body and into the patient's vagina, coupling the guide needle to a distal end of the attachment strip using a coupling means, and retracting the guide needle and attached attachment strip through the body through the passageway adjusting the mesh using ends of the attachment strips so as to restore the prolapsed organ closer to its proper anatomical position and support it there;

removing a portion of the attachments strips that are outside of the body; and leaving the mesh and remaining attachment strips within the body.

10. The method according to claim 9, wherein, for the first and second front attachment strips, the passageway through the patient's body extends from an exterior of the abdomen, around the pubic bone and out of the vagina, on first and second sides of the bladder respectively.

11. The method according to claim 10, wherein, for the first and second rear attachment strips, the passageway through the patient's body extends from an exterior of the abdomen at a location caudal and lateral to the location of the first and second front attachment strips, around the bladder and out through the vagina, on first and second sides of the bladder respectively.

12. The method according to claim 10, wherein, for the first and second front attachment strips, the passageway through the patient's body extends from an exterior of the medial side of the hip, through the obturator fossa, around the obturator bone, and out thought the vagina, on first and second sides of the bladder respectively.

13. The method according to claim 9, wherein a first guide needle is used to create the passageway for the first and second front attachment strips, and as second guide needle is used to create the passageway for the first and second rear attachment strips, and wherein the first guide needle has a curvature different than the second guide needle.

14. The method according to claim 9, wherein, for each of the first and second front and rear attachment strips, the coupling means is a coupling member fixedly secured at one end to a distal end of the attachment strip, and having an opening at a second end for receiving therein and securely engaging a distal end of the guide needle.

15. The method according to claim 9, wherein, for each of the first and second front and rear attachment strips, the coupling means comprises a needle element fixedly attached at a proximal end to a distal end of the attachment strip, and a coupling device for coupling the distal end of the needle element with the distal end of the guide needle.

16. The method according to claim 15, wherein the coupling device has an opening at a first end for receiving therein and securely engaging the distal end of the needle element, and an opening at a second end for receiving therein and securely engaging the distal end of the guide needle.

17. The surgical kit according to claim 5, wherein the curvature of the second guide needle is such that it can extend from an exterior of the medial side of the hip, through the obturator fossa, around the obturator bone, and out through the vagina.

* * * * *